United States Patent
Taniguchi et al.

(10) Patent No.: US 11,596,318 B2
(45) Date of Patent: Mar. 7, 2023

(54) BLOOD PRESSURE MEASUREMENT CUFF AND METHOD FOR MANUFACTURING BLOOD PRESSURE MEASUREMENT CUFF

(71) Applicant: OMRON HEALTHCARE CO., LTD., Muko (JP)

(72) Inventors: Minoru Taniguchi, Kyoto (JP); Tomonori Yuasa, Kyoto (JP); Masaki Harada, Kyoto (JP); Tameo Ashida, Kyoto (JP); Chisato Uesaka, Kyoto (JP); Wataru Tsunoda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 280 days.

(21) Appl. No.: 15/930,763

(22) Filed: May 13, 2020

(65) Prior Publication Data
US 2020/0268264 A1    Aug. 27, 2020

Related U.S. Application Data

(60) Division of application No. 14/818,961, filed on Aug. 5, 2015, which is a continuation of application No. PCT/JP2014/055567, filed on Mar. 5, 2014.

(30) Foreign Application Priority Data

Mar. 7, 2013   (JP) .................................. 2013-045788

(51) Int. Cl.
   *A61B 5/022*   (2006.01)
   *A61B 5/00*    (2006.01)

(52) U.S. Cl.
   CPC .......... *A61B 5/02233* (2013.01); *A61B 5/022* (2013.01); *A61B 5/683* (2013.01); *A61B 2562/12* (2013.01)

(58) Field of Classification Search
   None
   See application file for complete search history.

(56) References Cited

U.S. PATENT DOCUMENTS

| 3,670,735 A | 6/1972 | Hazlewood |
| 4,549,550 A | 10/1985 | Kami |

(Continued)

FOREIGN PATENT DOCUMENTS

| CN | 1748637 A | 3/2006 |
| JP | 2006-081667 A | 3/2006 |

(Continued)

OTHER PUBLICATIONS

Jan. 6, 2021 U.S. Office Action issued U.S. Appl. No. 14/818,961.

(Continued)

*Primary Examiner* — Alex M Valvis
*Assistant Examiner* — Aurelie H Tu
(74) *Attorney, Agent, or Firm* — Oliff PLC

(57) ABSTRACT

A method for manufacturing a blood pressure measurement cuff includes preparing an outer cloth, preparing an inner cloth, and forming a bag-shaped portion. The bag-shaped portion has an opening on a peripheral edge of the bag-shaped portion. A curler is inserted into the bag-shaped portion through the opening, the curler being flexible and configured to curve and conform to the measurement site. An air bladder is formed by welding the opening of the bag-shaped portion such that the air bladder surrounds an inner side and an outer side of the curler thereby containing the curler. The outer cloth is attached to an outer surface on a first side of the air bladder configured to be opposite to the measurement site, and the inner cloth is attached to an outer surface on a second side of the air bladder configured to be towards the measurement site.

3 Claims, 54 Drawing Sheets

(56) References Cited

U.S. PATENT DOCUMENTS

| | | | |
|---|---|---|---|
| 5,411,518 | A | 5/1995 | Goldstein et al. |
| 7,374,543 | B2 | 5/2008 | Kato |
| 2002/0099299 | A1 | 7/2002 | Inagaki |
| 2004/0034308 | A1 | 2/2004 | Inoue et al. |
| 2005/0182331 | A1* | 8/2005 | Millay ............... A61B 5/02233 600/499 |
| 2006/0012491 | A1 | 1/2006 | Mahowald |
| 2006/0135872 | A1 | 6/2006 | Karo et al. |
| 2007/0135836 | A1 | 6/2007 | McEwen et al. |
| 2009/0124913 | A1 | 5/2009 | Yamashita et al. |
| 2011/0282222 | A1 | 11/2011 | Tseng et al. |
| 2012/0231649 | A1 | 9/2012 | Sun |
| 2012/0302901 | A1* | 11/2012 | Kobayashi ............. A61B 5/022 600/494 |
| 2012/0316449 | A1 | 12/2012 | Uesaka et al. |

FOREIGN PATENT DOCUMENTS

| | | |
|---|---|---|
| JP | 2006-081668 A | 3/2006 |
| WO | 2011/081029 A1 | 7/2011 |
| WO | 2011105197 A1 | 9/2011 |

OTHER PUBLICATIONS

Apr. 22, 2022 Office Action issued in U.S. Appl. No. 14/818,961.
Jul. 9, 2020 Preliminary Office Action issued in Brazilian Patent Application No. 112015021361-8.
Aug. 17, 2020 Examination Report issued in Indian Patent Application No. 7061/DELNP/2015.
Apr. 1, 2014 Search Report issued in International Patent Application No. PCT/JP2014/055567.
Sep. 28, 2016 Office Action issued in Chinese Patent Application No. 201480010800.X.
Oct. 19, 2017 Office Action issued in U.S. Appl. No. 14/818,961.
Mar. 9, 2018 Office Action issued in U.S. Appl. No. 14/818,961.
Jun. 21, 2019 Office Action issued for U.S. Appl. No. 14/818,961.
Jan. 3, 2020 Office Action issued in U.S. Appl. No. 14/818,961.
U.S. Appl. No. 14/818,961, filed Aug. 5, 2015 in the name of Taniguchi et al.
Oct. 1, 2021 U.S. Office Action issued U.S. Appl. No. 14/818,961.

* cited by examiner

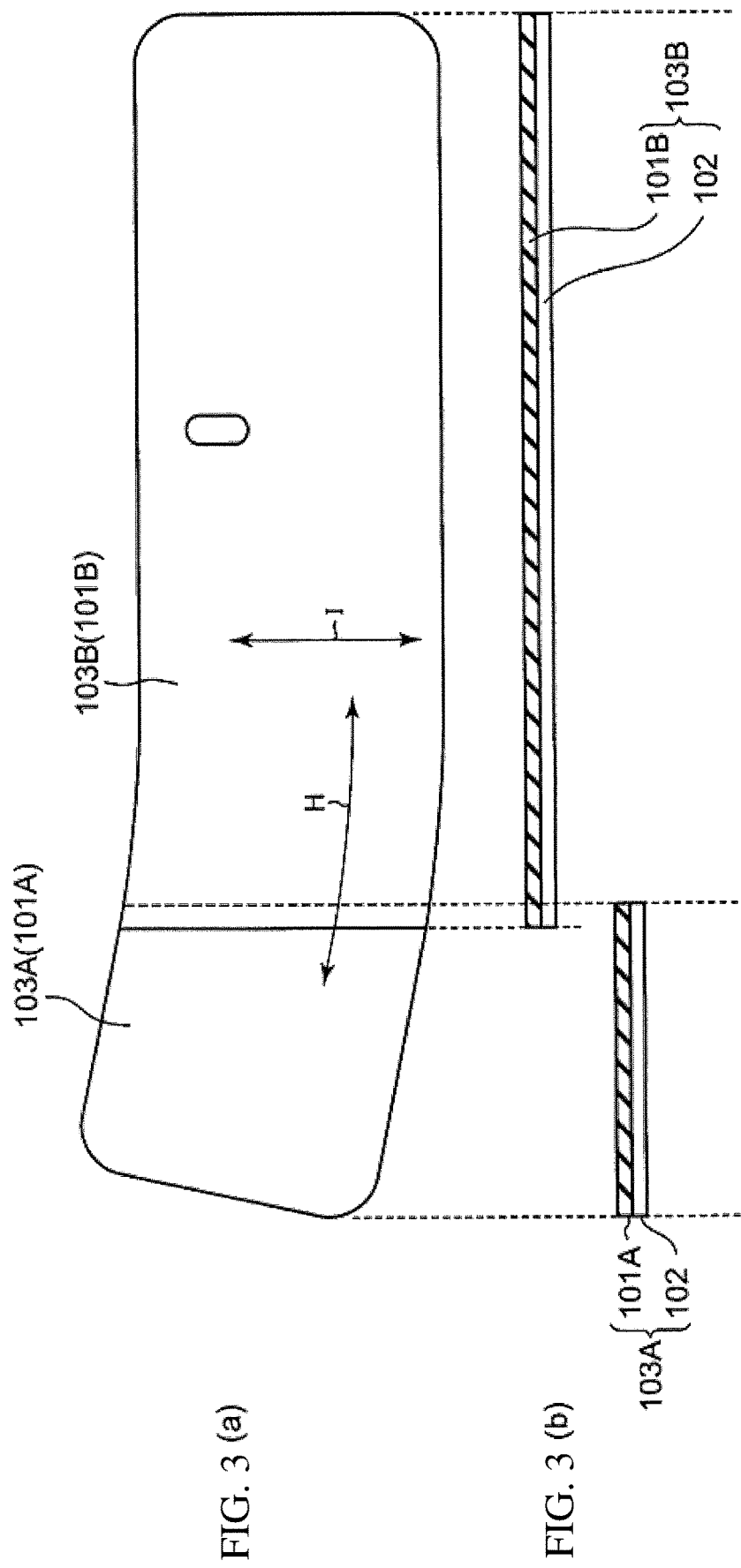

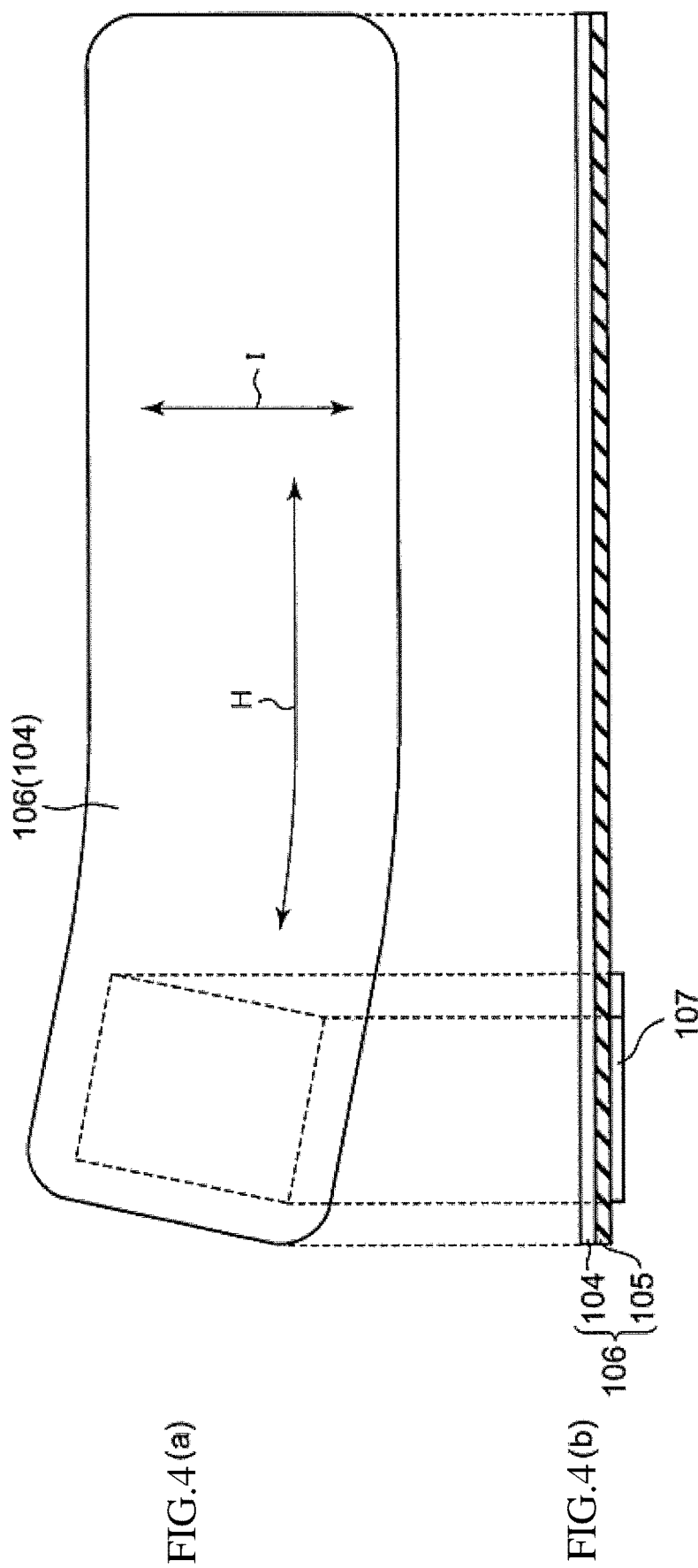

209p

209p1

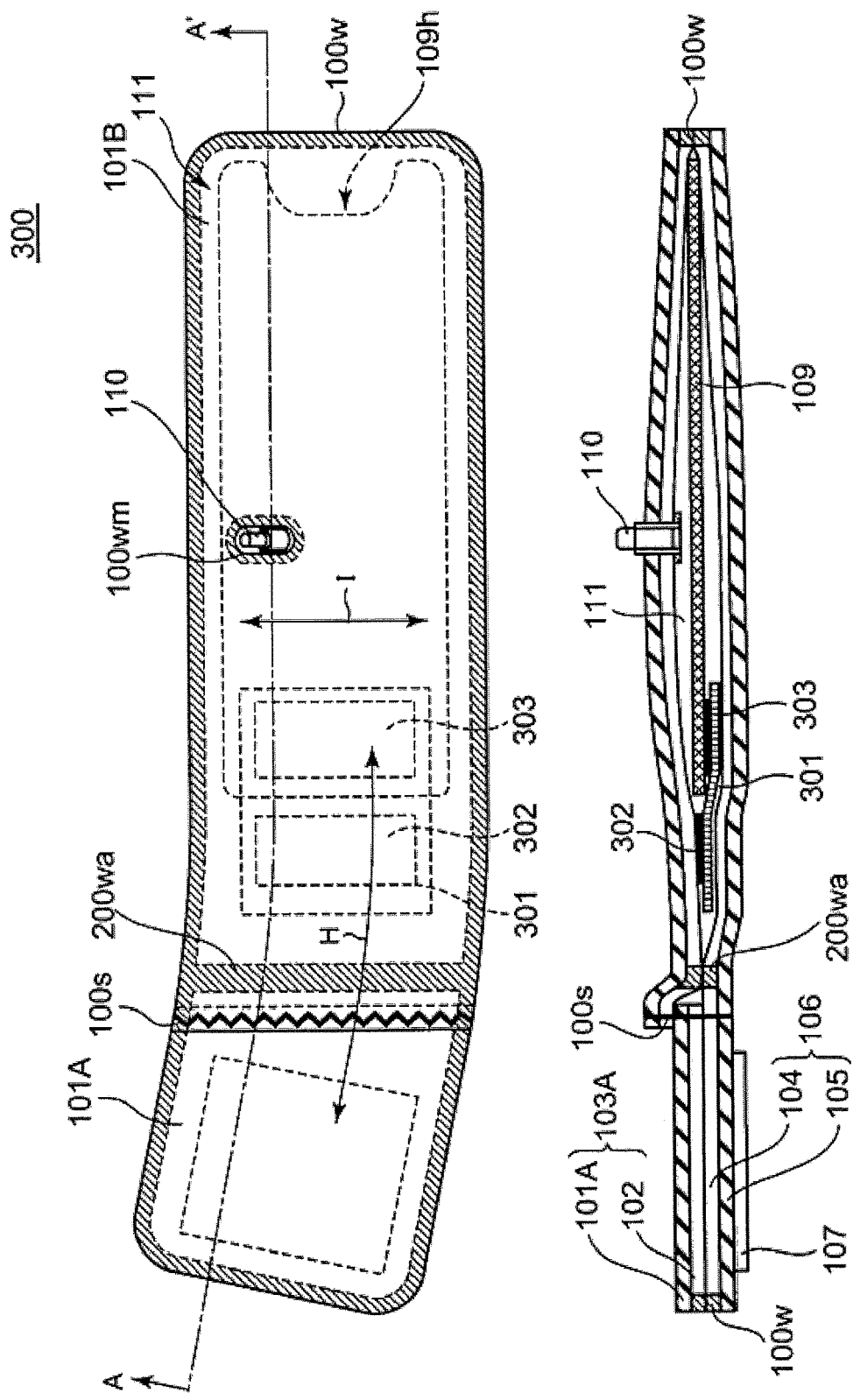

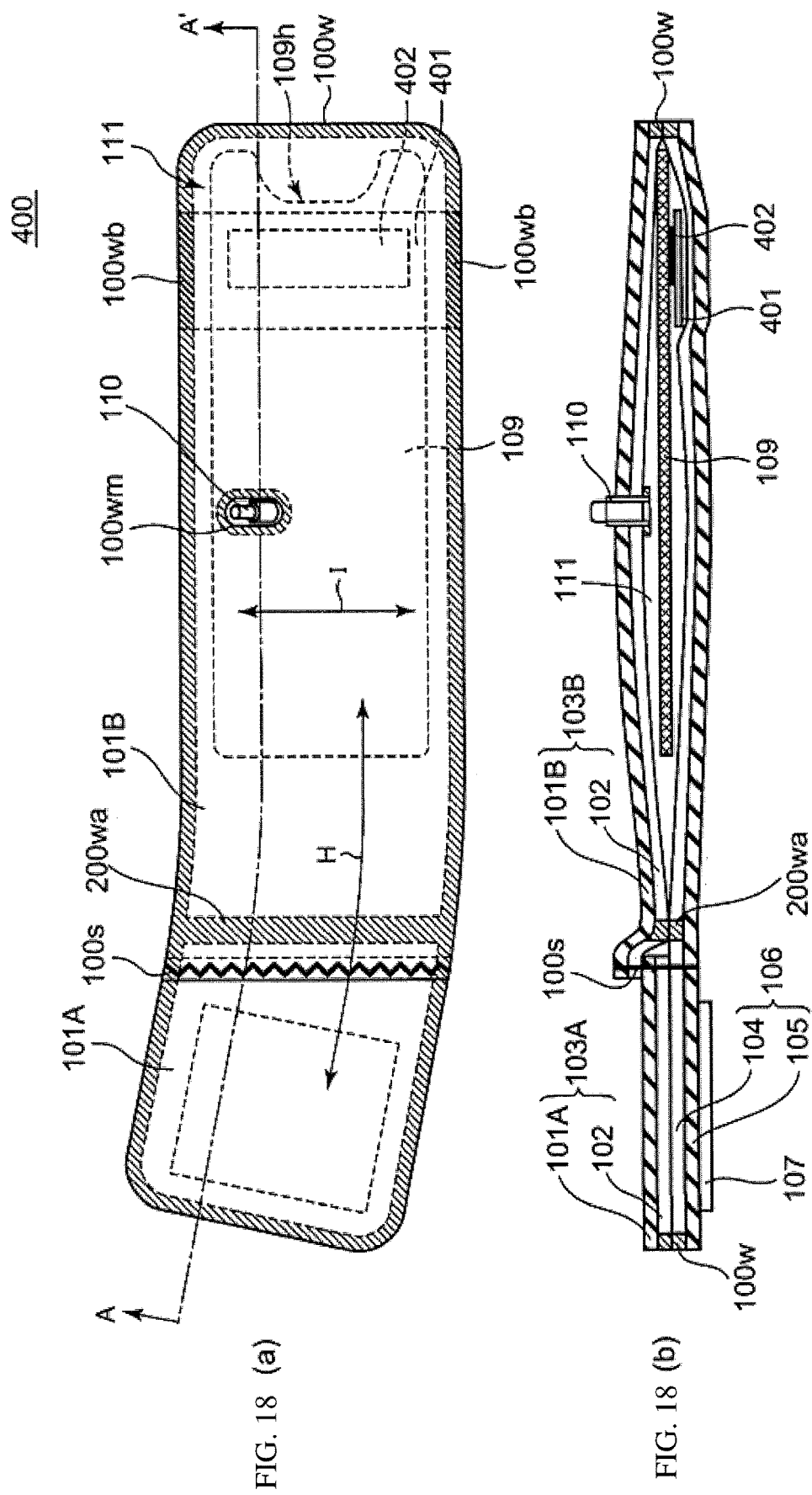

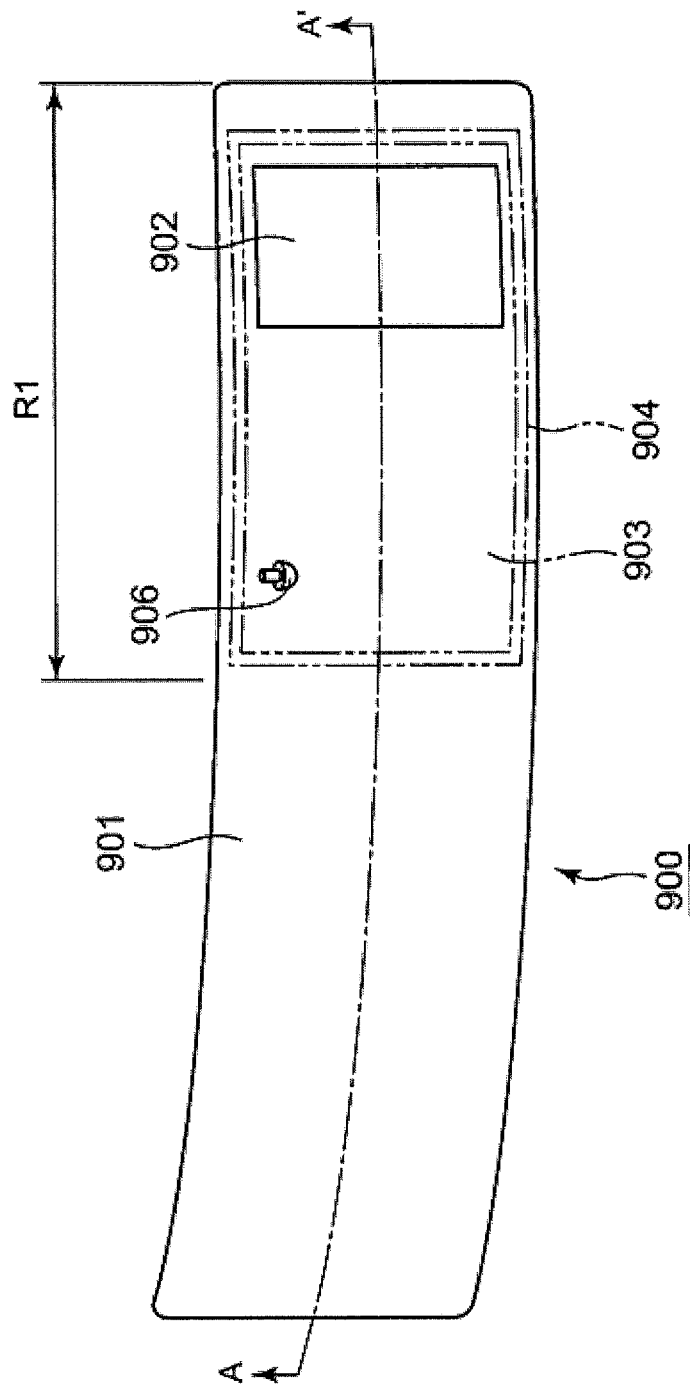
FIG. 29 (Prior technology)

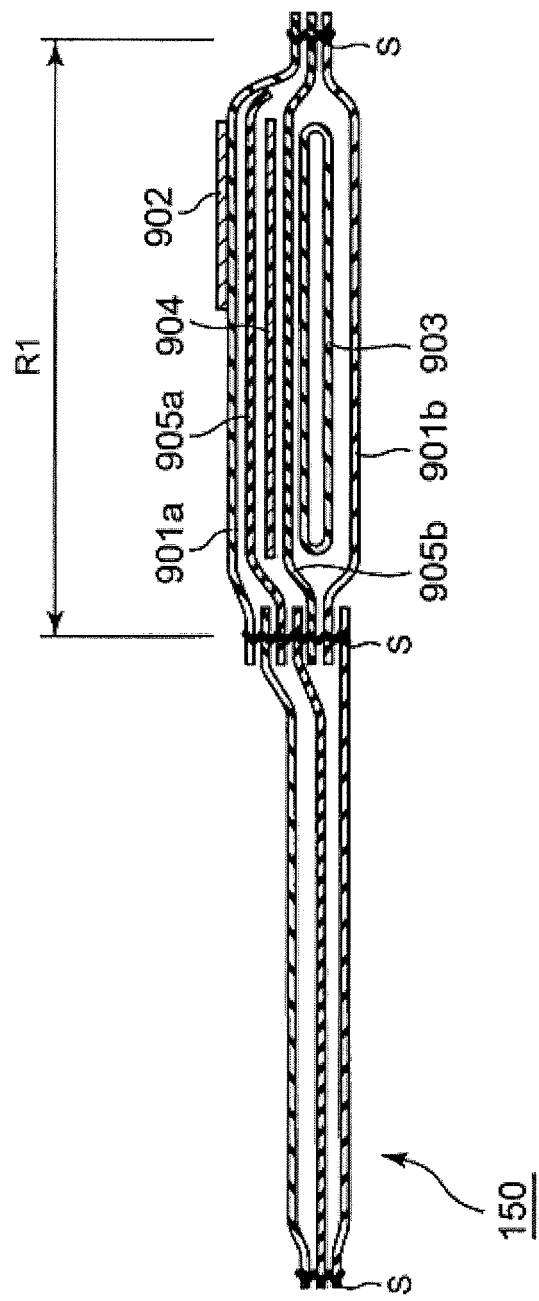
FIG. 30 (Prior technology)

BLOOD PRESSURE MEASUREMENT CUFF AND METHOD FOR MANUFACTURING BLOOD PRESSURE MEASUREMENT CUFF

This is a Division of application Ser. No. 14/818,961 filed Aug. 5, 2015, which is a Continuation of International Application No. PCT/JP2014/055567 filed Mar. 5, 2014, which claims priority to Japanese Patent Application No. 2013-045788 filed Mar. 7, 2013. The disclosures of the prior applications are hereby incorporated by reference herein in their entireties.

TECHNICAL FIELD

The present invention relates to a blood pressure measurement cuff, and more specifically relates to a blood pressure measurement cuff including a curler with a shape that conforms to a measurement site.

Also, the present invention relates to a method for manufacturing a blood pressure measurement cuff, and more specifically relates to a method for manufacturing a blood pressure measurement cuff including a curler with a shape that conforms to a measurement site.

BACKGROUND ART

Conventionally as this type of device, there have been blood pressure measurement cuffs that include a curler between an outer cloth (outer cover) and an air bladder, as shown in Patent Document 1 (WO 2011/081029A1), for example. This curler has a shape that naturally conforms to a measurement site such as an arm. Accordingly, it is easy to attach the cuff to the measurement site.

FIG. 29 is a plan view of an expanded state of the cuff indicated in Patent Document 1, and FIG. 30 shows a cross-sectional view taken along line A-A' in FIG. 29.

With reference to FIGS. 29 and 30, a cuff 900 is such that at a region R1 at which a fluid bladder (air bladder) is formed, an air bladder 903 and a curler 904 are contained in a bag-shaped outer cover formed by a first outer cloth 901*a* and a first inner cloth 901*b*.

In the cuff 900, low-friction inner sheets 905*a* and 905*b* are added respectively between the first outer cloth 901*a* and the curler 904 and between the curler 904 and the air bladder 903.

The two inner sheets 905*a* and 905*b* are added in the cuff 900 for the following reason. Accompanying supply of air to or discharge of air from the air bladder 903, the air bladder 903 begins to deform. However, this deformation is sometimes hindered due to friction generated at the point of contact between the air bladder 903 and another member.

Then, the deformation is obstructed until the friction becomes equal to the maximum static friction at the point of contact, that is, until the size of the shearing stress becomes equal to the size of the maximum static friction. Then, as soon as the amount of the shearing stress acting at the point of contact exceeds the amount of the maximum static friction, sudden deformation occurs in the air bladder 903, which causes a relatively loud noise to be generated. This relatively loud noise sometimes adversely affects blood pressure measurement.

For this reason, in the cuff 900, in order to prevent noise that adversely affects blood pressure measurement from being generated, the two inner sheets 905*a* and 905*b* are provided between members that are thought to generate noise.

CITATION LIST

Patent Literature

Patent Document 1: WO 2011/081029A1

SUMMARY OF INVENTION

Technical Problem

However, in the prior technology, additional members, namely the inner sheets 905*a* and 905*b* (FIG. 30), are needed in order to suppress the generation of noise. For this reason, with the prior technology, a state of affairs has been incurred in which the manufacturing step is more complicated and costly and the cost of materials is increased.

In view of this, it is an object of the present invention to provide a blood pressure measurement cuff that can, with a more simple configuration, suppress generation of noise during inflation/deflation.

Also, it is an object of the present invention to provide a method for manufacturing a blood pressure measurement cuff that can, with a more simple configuration, suppress generation of noise during inflation/deflation.

Solution to Problem

In order to resolve the above-described problems, a blood pressure measurement cuff according to an aspect of the present invention is a blood pressure measurement cuff to be attached such that it wraps around a measurement site, the blood pressure measurement cuff including: a curler that is flexible and curves so as to naturally conform to a measurement site; an air bladder surrounding the inner side and outer side of the curler so as to contain the curler; an inner cloth attached to an outer surface on the measurement site side of the air bladder; and an outer cloth attached to an outer surface on the side opposite to the measurement site of the air bladder.

With the blood pressure measurement cuff according to an aspect of the present invention, the curler has a shape that naturally conforms to a measurement site such as an arm. Accordingly, it is easy to attach the cuff to the measurement site. Also, with this cuff, the air bladder is attached to the inner cloth and the outer cloth, and the curler is contained in the air bladder. Accordingly, as long as the air bladder contains air (pressurized air) with an air pressure higher than that of the surrounding environment, a force that causes the air bladder to deform and move away from the curler acts on the air bladder. Accordingly, when the cuff inflates/deflates during blood pressure measurement, the curler is never held down with a large amount of force so as to be compressed by the air bladder. Accordingly, at the point of contact between the curler and the air bladder, static friction of an amount large enough to oppose a large amount of shearing stress is never generated. For this reason, at the point of contact, a case never occurs in which a sudden shearing deformation occurs and a noise loud enough to interfere with blood pressure measurement is generated. Also, since the air bladder, the inner cloth, and the outer cloth are attached, the three deform integrally during inflation/deflation. Accordingly, when the cuff inflates/deflates, the relative positional relationship between the air bladder and the inner cloth and outer cloth never shifts. Accordingly, with the present blood pressure measurement cuff, generation of noise during inflating/deflation which may hinder blood pressure measurement is suppressed.

With a blood pressure measurement cuff according to an embodiment, at at least one circumferential end of the curler in a circumferential direction in which the curler is wrapped around the measurement site, a central portion in a width direction, which is approximately perpendicular to the circumferential direction, recedes in the circumferential direction with respect to corner portions on both sides in the width direction.

With the blood pressure measurement cuff according to the embodiment, at the circumferential end of the curler, the central portion in the width direction recedes with respect to the corner portions. Accordingly, at the peripheral edge of the air bladder located near the central portion, the air bladder can move and deform such that it enters the central portion of the curler. For this reason, when the air bladder is inflated/deflated, the portion of the air bladder near the peripheral edge can deform significantly toward the measurement site such that the peripheral edge of the air bladder approaches the central portion. Therefore, the cuff can compress the measurement site well at locations near the peripheral edge of the air bladder as well.

With a blood pressure measurement cuff according to an embodiment, the air bladder is formed by the peripheral edges of two airtight sheet members being welded together.

With the blood pressure measurement cuff according to the embodiment, the air bladder is formed using a welding step, and the inner cloth and outer cloth are originally attached to the air bladder. For this reason, the blood pressure measurement cuff can be manufactured using only a welding step, and for example, a step of sewing the inner cloth and outer cloth together can be eliminated, thus reducing the cost of manufacturing.

A blood pressure measurement cuff according to an embodiment further includes a positioning portion configured to fix a relative positional relationship between the curler and the air bladder.

With the blood pressure measurement cuff according to the embodiment, it is possible to prevent the curler from moving inside of the air bladder.

A blood pressure measurement cuff according to an embodiment further includes a nipple for supplying/discharging air, wherein the positioning portion is a protrusion that is formed on the outer surface of the curler and is fitted into the interior of the nipple.

With the blood pressure measurement cuff according to the embodiment, it is possible to prevent the curler from moving inside of the air bladder with an extremely simple configuration.

With a blood pressure measurement cuff according to an embodiment, the positioning portion is a sheet member attached to the inner surface of the air bladder, and the curler is attached to the sheet member such that the relative positional relationship with the air bladder is fixed.

With the blood pressure measurement cuff according to the embodiment, it is possible to prevent the curler from moving inside of the air bladder with an extremely simple configuration.

With a blood pressure measurement cuff according to an embodiment, the positioning portion is a sheet member that is fixed by being welded to the air bladder while being sandwiched between the two airtight sheet members forming the air bladder, and the curler is attached to the sheet member such that the relative positional relationship with the air bladder is fixed.

With the blood pressure measurement cuff according to the embodiment, it is possible to prevent the curler from moving inside of the air bladder with an extremely simple configuration.

With a blood pressure measurement cuff according to an embodiment, the sheet member is fixed by being welded to the air bladder at a portion on the peripheral edge in a length direction, which is parallel to the circumferential direction in which the air bladder is wrapped around the measurement site.

With the blood pressure measurement cuff according to the embodiment, it is possible to prevent the curler from moving inside of the air bladder with an extremely simple configuration.

With a blood pressure measurement cuff according to an embodiment, the sheet member is fixed by being welded to the air bladder at a portion on the peripheral edge in the width direction, which is approximately perpendicular to the circumferential direction in which the air bladder is wrapped around the measurement site.

With the blood pressure measurement cuff according to the embodiment, it is possible to prevent the curler from moving inside of the air bladder with an extremely simple configuration.

In order to resolve the above-described problems, a method for manufacturing a blood pressure measurement cuff according to another aspect of the present invention is a method for manufacturing a blood pressure measurement cuff to be attached such that it wraps around a measurement site, the method including: a step of preparing an outer cloth to which a first airtight sheet member for air bladder formation is attached, and an inner cloth to which a second airtight sheet member for air bladder formation is attached; a step of forming a bag-shaped portion by welding the first airtight sheet member and the second airtight sheet member together, the bag-shaped portion having an opening at at least a portion of a peripheral edge thereof; a step of inserting a curler into the bag-shaped portion through the opening; and a step of forming an air bladder by welding the opening of the bag-shaped portion.

With the method for manufacturing a blood pressure measurement cuff, which is another aspect of the present embodiment, a blood pressure measurement cuff can be manufactured easily and at a lower cost.

With a method for manufacturing a blood pressure measurement cuff according to an embodiment, the step of inserting the curler into the bag-shaped portion includes: a sub-step of first inserting a flat plate-shaped curler insertion auxiliary plate into the bag-shaped portion through the opening; a sub-step of next pressing the curler to the curler insertion auxiliary plate so as to elastically deform the curler into an approximate plate shape, and sliding the curler over the plate and through the opening so as to insert the curler into the bag-shaped portion; and a sub-step of taking the curler insertion auxiliary plate out of the bag-shaped portion through the opening.

With the method for manufacturing a blood pressure measurement cuff according to the embodiment, the curler can be inserted into the bag-shaped portion extremely easily.

With a method for manufacturing a blood pressure measurement cuff according to an embodiment, the step of inserting the curler into the bag-shaped portion includes: a sub-step of first inserting two plate-shaped curler insertion auxiliary plates and the curler into the bag-shaped portion through the opening while sandwiching the curler between the two curler insertion auxiliary plates by elastically deforming the curler into an approximate plate shape; and a sub-step of taking the two curler insertion auxiliary plates out of the bag-shaped portion through the opening.

With the method for manufacturing a blood pressure measurement cuff according to the embodiment, the curler can be inserted into the bag-shaped portion extremely easily.

A method for manufacturing a blood pressure measurement cuff according to an embodiment further includes a step of fitting a protrusion formed on the outer surface of the curler into the interior of a nipple arranged on the outer cloth, after the step of inserting the curler into the bag-shaped portion, and before the step of forming the air bladder.

With the method for manufacturing a blood pressure measurement cuff according to the embodiment, a blood pressure measurement cuff in which a curler is prevented from moving inside an air bladder can be manufactured with simple steps.

In a method for manufacturing a blood pressure measurement cuff according to an embodiment, the step of forming the bag-shaped portion is such that a third sheet member is sandwiched between the first sheet member and the second sheet member at a portion of the peripheral edge in the length direction, which is parallel to the circumferential direction in which the bag-shaped portion is wrapped around the measurement site; and the method further includes a step of attaching the curler to the third sheet member after the step of inserting the curler into the bag-shaped portion, and before the step of forming the air bladder.

With the method for manufacturing a blood pressure measurement cuff according to the embodiment, a blood pressure measurement cuff in which a curler is prevented from moving inside an air bladder can be manufactured with simple steps.

A method for manufacturing a blood pressure measurement cuff according to an embodiment further includes a step of attaching a third sheet member to the curler before the step of inserting the curler into the bag-shaped portion; and a step of attaching the third sheet member to the inner surface of the bag-shaped portion after the step of inserting the curler into the bag-shaped portion, and before the step of forming the bag-shaped portion.

With the method for manufacturing a blood pressure measurement cuff according to the embodiment, a blood pressure measurement cuff in which a curler is prevented from moving inside an air bladder can be manufactured with simple steps.

A method for manufacturing a blood pressure measurement cuff according to an embodiment further includes a step of attaching a third sheet member to the curler before the step of inserting the curler into the bag-shaped portion, wherein the step of forming the air bladder is such that the third sheet member is sandwiched between the first sheet member and the second sheet member and is welded to a portion in the width direction, which is approximately perpendicular to the circumferential direction in which the air bladder is wrapped around the measurement site.

With the method for manufacturing a blood pressure measurement cuff according to the embodiment, a blood pressure measurement cuff in which a curler is prevented from moving inside an air bladder can be manufactured with simple steps.

Advantageous Effects of Invention

According to the blood pressure measurement cuff of the present embodiment, it is possible to suppress generation of noise that can hinder blood pressure measurement during inflation/deflation.

According to the method for manufacturing the blood pressure measurement cuff of the present embodiment, a blood pressure measurement cuff that can suppress the generation of noise that can hinder blood pressure measurement during inflation/deflation can be manufactured more easily and at a lower cost.

BRIEF DESCRIPTION OF DRAWINGS

FIG. 3(a) is a plan view of an outer cloth of a blood pressure measurement cuff, and FIG. 3(b) is an elevational view of the same outer cloth.

FIG. 4(a) is a plan view of an inner cloth of a blood pressure measurement cuff, and FIG. 4(b) is an elevational view of the same inner cloth.

FIG. 14(a) is a plan view of an expanded state of a blood pressure measurement cuff according to a third embodiment, and FIG. 14(b) is a cross-sectional view taken along line A-A' in FIG. 14(a).

FIG. 18(a) is a plan view of an expanded state of a blood pressure measurement cuff according to a fourth embodiment, and FIG. 18(b) is a cross-sectional view taken along line A-A' in FIG. 18(a).

FIG. 29 is a plan view of a blood pressure measurement cuff with a conventional shape.

FIG. 30 is a cross-sectional view of the blood pressure measurement cuff with the conventional shape, taken along line A-A' in FIG. 29.

DESCRIPTION OF EMBODIMENTS

Hereinafter, embodiments of the present invention will be described in detail with reference to the drawings.

With a blood pressure measurement cuff according to an embodiment of the present invention, a curler has a shape that naturally conforms to a measurement site such as an arm. Accordingly, it is easy to attach the cuff to the measurement site. Also, with this cuff, an outer cloth and an inner cloth, which are outer cover members, and an air bladder are in an integrated configuration, and the curler is contained inside of the air bladder. Thus, when the cuff inflates/deflates, the outer cloth and inner cloth and the air bladder deform/move in an integrated manner. Accordingly, the relative positional relationship between the outer cloth and inner cloth, and the air bladder never shifts. For this reason, noise that may hinder blood pressure measurement is never generated between the inner cloth and outer cloth and the air bladder during inflation/deflation. Also, since a configuration is used in which the curler is contained in the air bladder, the force of deformation/movement in the direction away from the curler acts in the air bladder as long as pressurized air exists in the air bladder. In particular, when the cuff inflates/deflates for blood pressure measurement, the curler is never held down with a large amount of force so as to be compressed by the air bladder. Accordingly, at the point of contact between the curler and the air bladder, static friction of an amount large enough to oppose a large amount of shearing stress is never generated. For this reason, at the point of contact, a case never occurs in which a sudden shearing deformation occurs, generating a noise loud enough to interfere with blood pressure measurement.

Also, with the blood pressure measurement cuff according to an embodiment of the present invention, a conventionally needed step of sewing together the inner cloth and the outer cloth, which are outer cover portions (a step of forming a bag-shaped outer cover from two sheet-shaped outer cover members), can be eliminated. Accordingly, the blood pressure measurement cuff is advantageous for the manufacturing cost as well.

Figure 1:
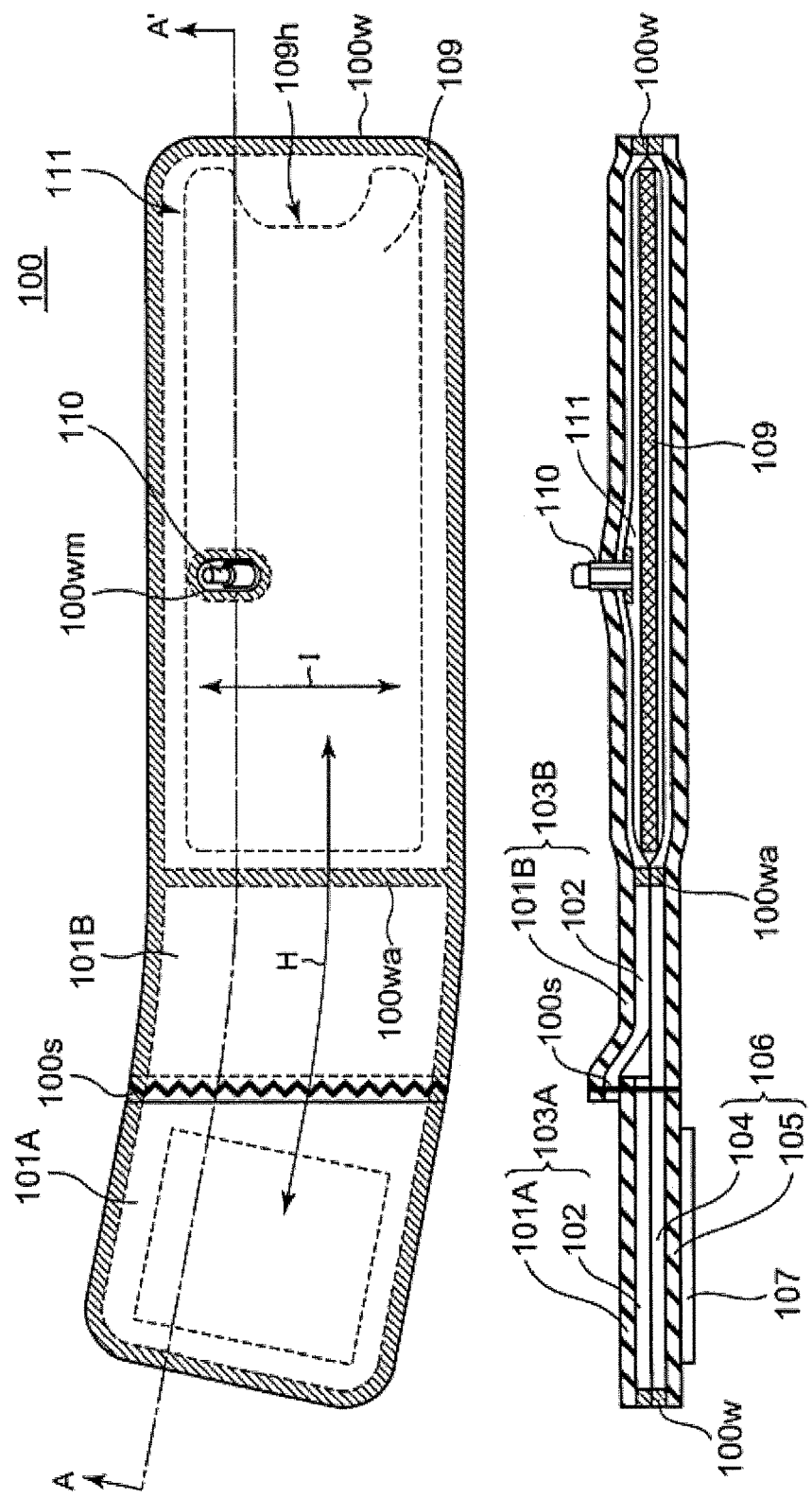
FIG. 1(a) is a plan view of an expanded state of a blood pressure measurement cuff according to a first embodiment.
FIG. 1(b) is a cross-sectional view taken along line A-A' in FIG. 1(a).

FIG. 1(a) is a plan view of an expanded state of a blood pressure measurement cuff (hereinafter abbreviated as "cuff") according to a first embodiment of the present invention, and FIG. 1(b) is a cross-sectional view taken along line A-A' in FIG. 1(a).

A cuff 100 has a narrow, flat band shape. The cuff 100 is wrapped around the measurement site in the length direction and is attached to the measurement site by engagement between a hook-and-loop fastener 107 and an outer cloth 101B. Here, the measurement site is a person's upper arm, for example, but the measurement site is not limited thereto.

The outer cloths 101A and 101B form an outer cover member that is located on the outer side when the cuff 100 is wrapped around the measurement site. The outer cover member, which is on the outside, is composed of two members, namely the outer cloth 101A and the outer cloth 101B, and is made into one member by a suture 100s. Note that in the present embodiment, the above-described outer cover member that is on the outside may originally be a single member with a shape that is formed when the outer cloth 101A and the outer cloth 101B are sewn together. In this case, the suture 100s can be omitted. Also, a nipple 110 is arranged on the outer cloth 101B as a means for supplying/discharging air.

With reference to the cross-sectional view in FIG. 1(b), an airtight sheet member 102 is attached to the surfaces of the outer cloths 101A and 101B so as to be integrated. Here, the members obtained by attaching the airtight sheet 102 to the outer cloths 101A and 101B are referred to as outer members 103A and 103B.

The inner cloth 105 is an outer cover member that is located on the inner side (measurement site side) when wrapped around the measurement site. A hook-and-loop fastener 107 that engages with the outer cloths 101A and 101B is attached to the inner cloth 105. The airtight sheet member 104 is attached to and integrated with the surface of the inner cloth 105 opposite to the hook-and-loop fastener 107. Here, the member obtained by attaching the airtight sheet 104 to the inner cloth 105 will be referred to as an inner member 106.

The airtight sheet 102 of the outer member 103B and the airtight sheet 104 of the inner member 106 are joined by being welded together at a peripheral edge welded portion 100w and a intermediate welded portion 100wa, thus forming the air bladder 111.

A flexible curler 109 that curves so as to naturally conform to the measurement site is contained in the air bladder 111. With the cuff 100 according to the present embodiment, the length in the circumferential direction H (direction of wrapping around the measurement site) of the curler 109 is a dimension that is almost the same as the length in the circumferential direction H of the air bladder 111. This is favorable in terms of preventing the curler 109 from moving around in the air bladder 111 when the user wraps the cuff 100, for example. Also, on an end portion in the circumferential direction H (circumferential end (right end of the curler 109 in FIG. 1(a))), the curler 109 has a recess 109h whose central portion in a width direction I, which is approximately perpendicular to the circumferential direction H, recedes in the circumferential direction with respect to the corner portions located on both sides in the width direction. Effects of the recess 109h will be described in detail later.

Figure 2:
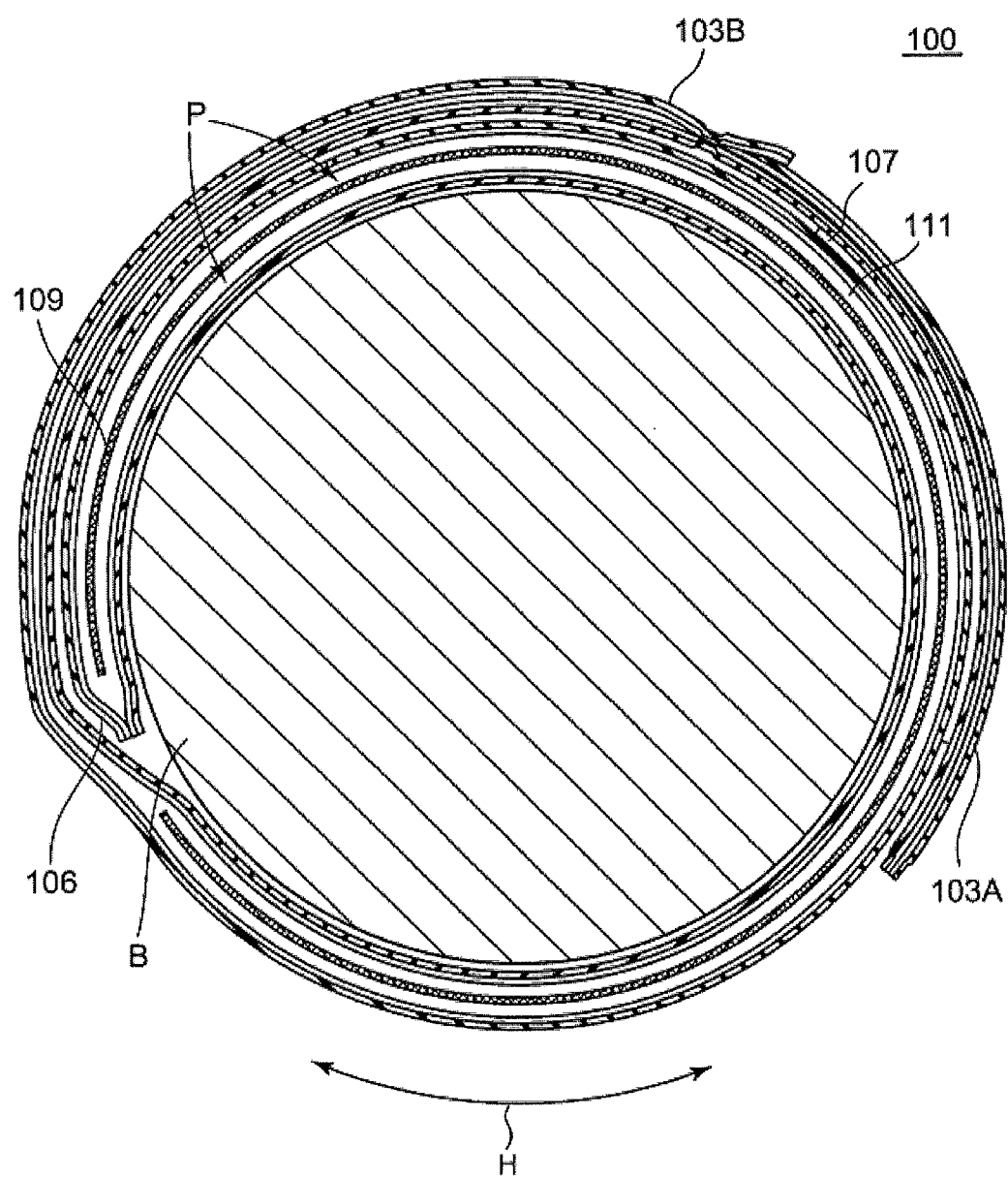
FIG. 2 is a cross-sectional view of a blood pressure measurement cuff in a state of being wrapped around a measurement site.

FIG. 2 is a cross-sectional view of the cuff 100 in a state in which the cuff 100 is fixed by being wrapped around a measurement site B and air has been inserted into the air bladder 111. Thus, with the cuff 100, when air is supplied to the air bladder 111, the air bladder 111 deforms/moves in the direction away from the curler 109. For this reason, as indicated by the arrows P, the curler 109 is never held down with a large amount of force by the air bladder 111 when the cuff 100 inflates/deflates. Accordingly, even if the two come into contact accompanying inflation/deflation of the air bladder 111, the force applied at the point of contact is kept extremely small. Accordingly, a case never occurs in which a large shearing force is generated between the curler 109 and the air bladder 111 and change in the relative positional relationship between the two and deformation of the two are hampered for a certain period until the stress exceeds the maximum static friction between the two, whereafter a large shearing movement occurs. Also, the airtight sheets 102 and 104 that constitute the air bladder 111 deform/move integrally with the outer cloths 101A and 101B and the inner cloth 105, and therefore the positional relationship between the three never shifts during inflation/deflation. Accordingly, with the present blood pressure measurement cuff, generation of noise which may hinder blood pressure measurement during inflating/deflation is suppressed.

FIG. 3(a) is a plan view of the outer members 103A and 103B, and FIG. 3(b) is an elevational view thereof. The outer members 103A and 103B are formed by attaching the airtight sheet 102 to the outer cloths 101A and 101B. The outer cloths 101A and 101B are raised cloth made of polyester or nylon. Also, the outer cloths 101A and 101B can be formed using other materials as well.

The airtight sheet 102 is a sheet member made of polyvinyl chloride (PVC). Also, the airtight sheet 102 can be formed using other materials as well. In order to attach the airtight sheet 102 to the outer cloths 101A and 101B, it is sufficient to laminate PVC on the outer cloths 101A and 101B or to appropriately coat the outer cloths 101A and 101B with melted PVC. Alternatively, PVC in the form of a sheet, or in other words, the airtight sheet 102 itself, may be adhered to the outer cloths 101A and 101B using an adhesive. In the present invention, there is absolutely no limitation to the method for attaching the airtight sheet 102 to the outer cloths 101A and 101B.

FIG. 4(a) is a plan view of the inner member 106, and FIG. 4(b) is an elevational view thereof. The inner member 106 is formed by attaching the airtight sheet 104 to the inner cloth 105. The inner cloth 105 is cloth made of polyester or nylon, similarly to the outer cloths 101A and 101B. Also, the inner cloth 105 can be formed using other materials as well. It is desired that the inner cloth 105 has greater elasticity than the outer cloths 101A and 101B. Regardless of the material that is selected, the elasticity of the outer cloths 101A and 101B and the inner cloth 105 can be adjusted by selecting how they are woven.

With the inner member 106 as well, the airtight sheet 104 is a sheet member made of polyvinyl chloride (PVC), similarly to the outer members 103A and 103B. Also, the airtight sheet 104 can be formed using other materials as well. In order to attach the airtight sheet 104 to the inner cloth 105, it is sufficient to laminate PVC on the inner cloth 105 or to coat the inner cloth 105 with melted PVC. Alternatively, PVC in the form of a sheet, or in other words, the airtight sheet 104 itself, may be adhered to the inner cloth 105 using an adhesive. In the present invention, there is absolutely no limitation to the method for attaching the airtight sheet 104 to the inner cloth 105.

Figure 5A:
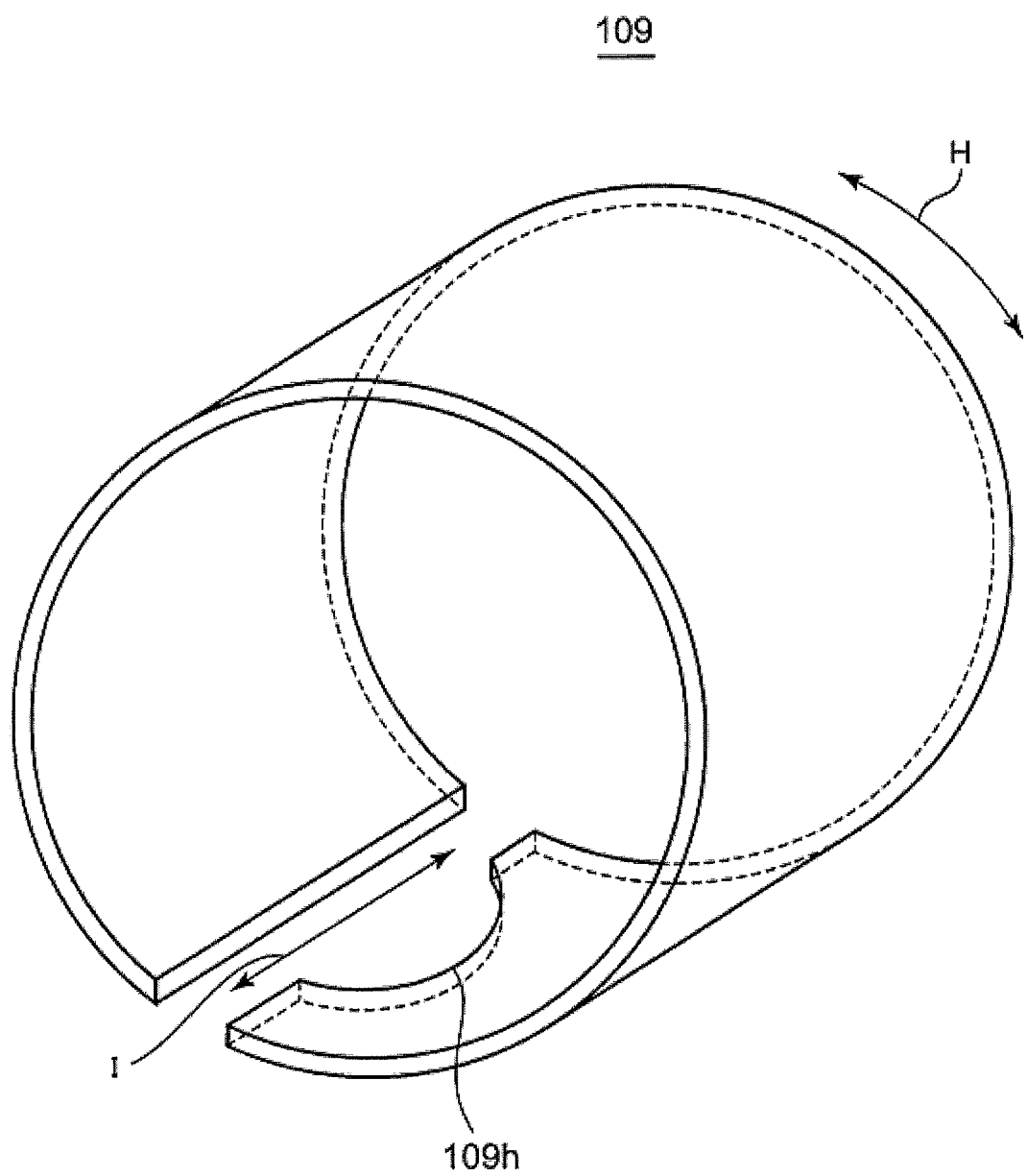
FIG. 5A is a perspective view of a curler for the blood pressure measurement cuff according to the first embodiment.

FIG. 5A is a perspective view of the curler 109. In its natural state, the curler 109 is a flexible member with a shape that is curved along the direction of wrapping around the measurement site (along the circumferential direction H). Also, at the end in the circumferential direction H (circumferential end), the curler 109 has a recess 109h that recedes in the central portion in the circumferential direction H with respect to the corner portions.

Figure 5B:
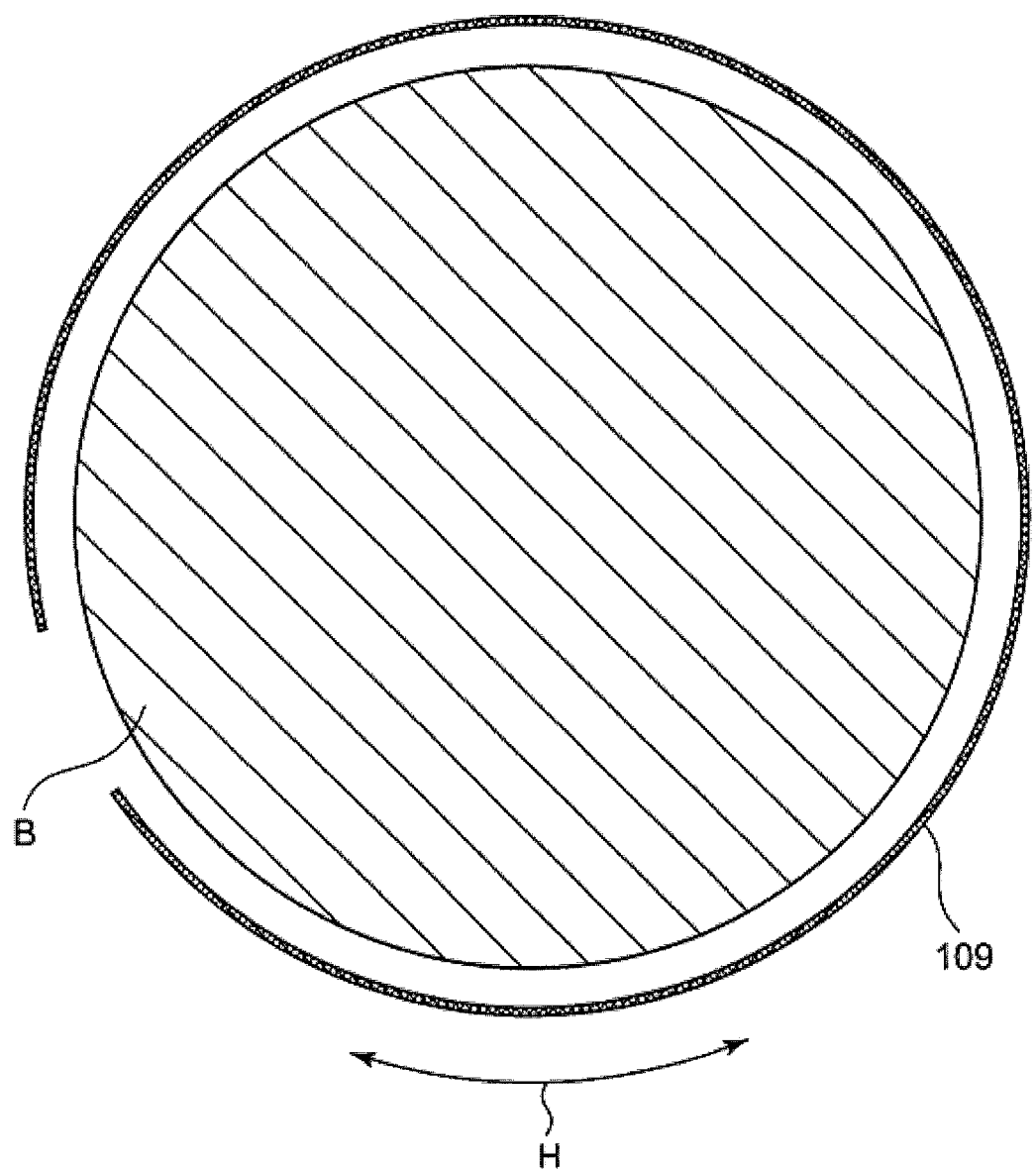
FIG. 5B is a schematic diagram showing a relationship between the length in the circumferential direction of the curler and the circumference of the measurement site.
Figure 5C:
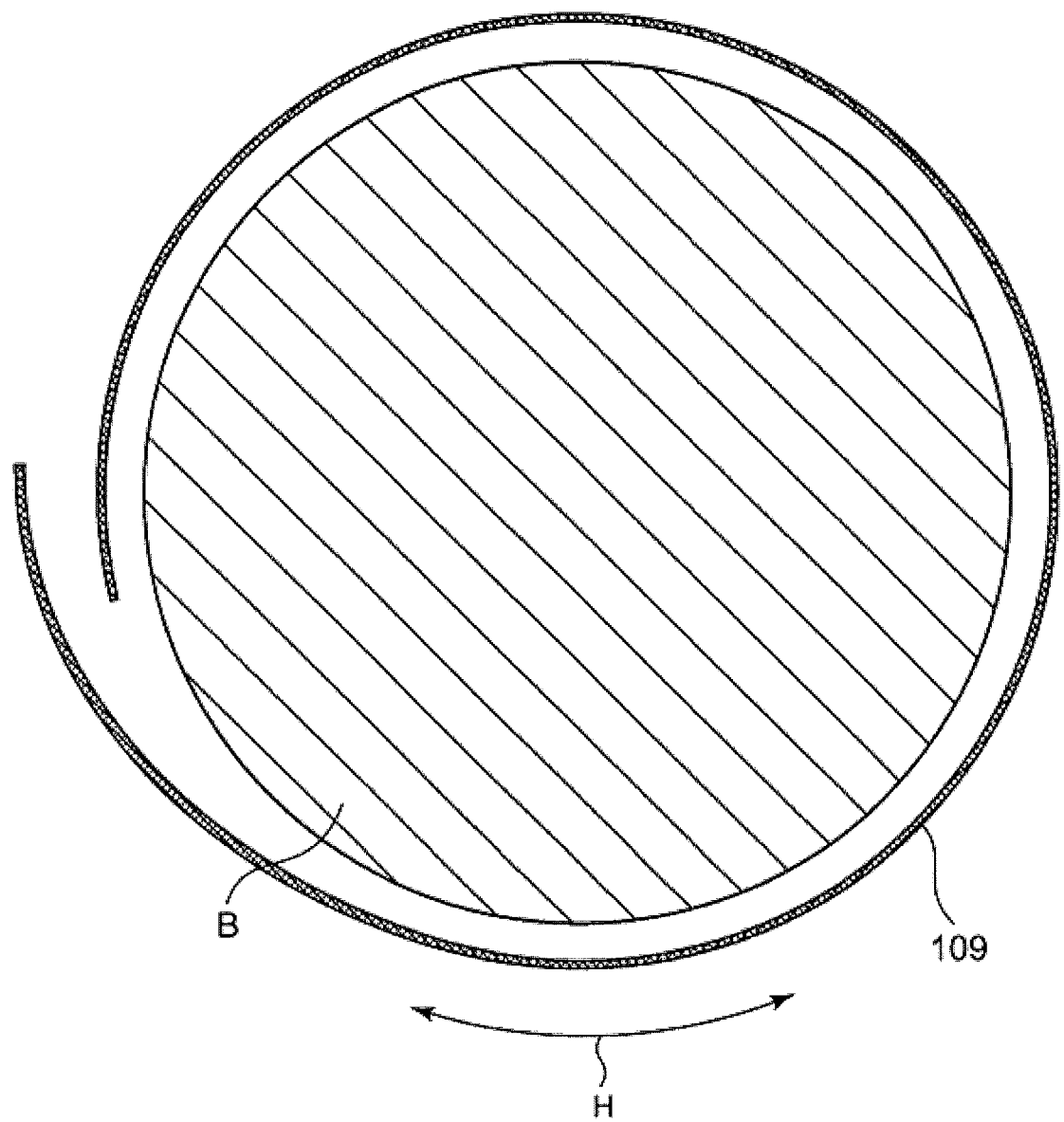
FIG. 5C is a schematic diagram showing a relationship between the length in the circumferential direction of the curler and the circumference of the measurement site.

FIGS. 5B and 5C are diagrams showing the relationship between the length in the circumference direction H of the curler 109 and an envisioned measurement site B. The curler 109 may be shorter than the circumference of the measurement site B, as shown in FIG. 5B. However, it is desired that the curler 109 has a length in the circumferential direction H that is longer than half of the circumference of the measurement site B. Also, the curler 109 may be longer than the circumference of the envisioned measurement site B, as shown in FIG. 5C.

Figure 6A:
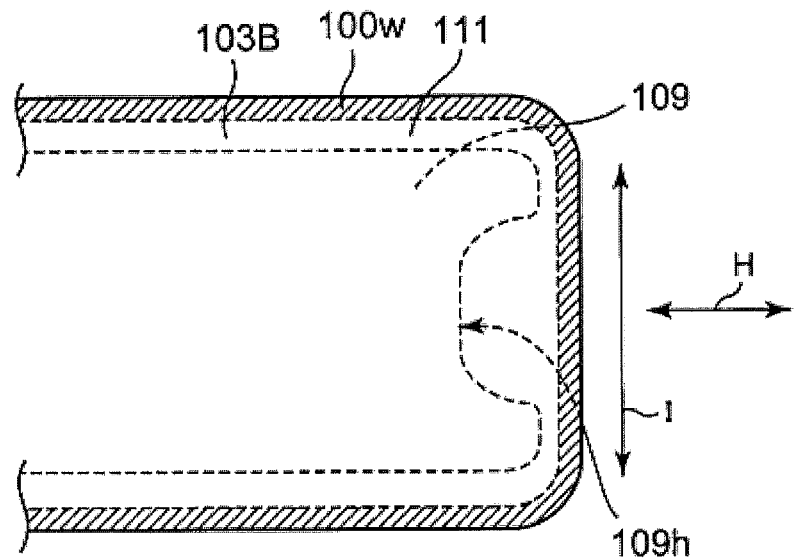
FIG. 6(a) is a schematic diagram showing an effect of a depression at the central portion of the circumferential end of the curler (deflated state)
Figure 6B:
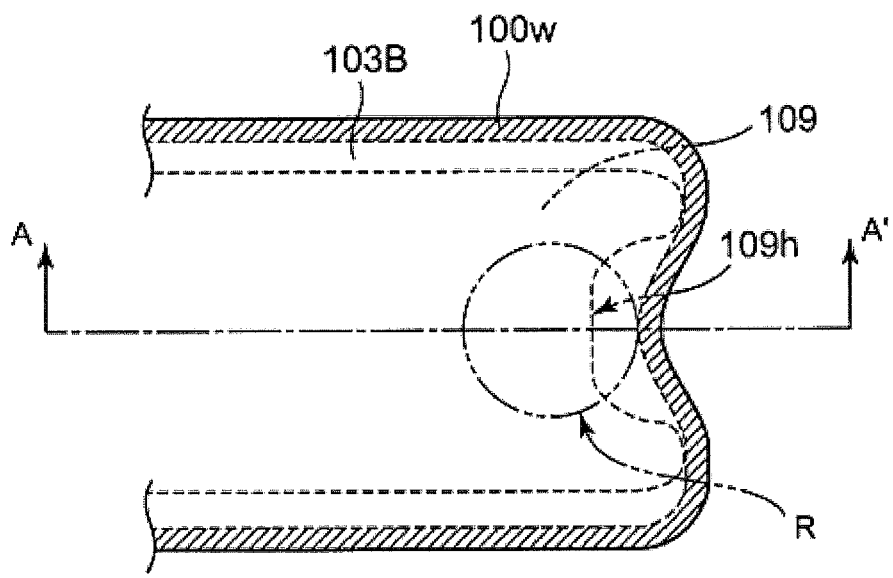
FIG. 6(b) is a schematic diagram showing an effect of the depression at the central portion of the circumferential end of the curler (inflated state)
Figure 6C:
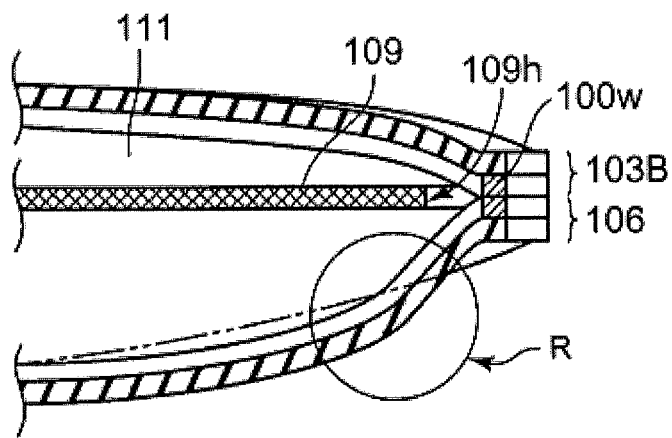
FIG. 6(c) is a cross-sectional view taken along line A-A' in FIG. 6(b).

FIG. 6 is a diagram for describing an effect of the recess 109h of the curler 109. FIG. 6(a) is a plan view showing the vicinity of the circumferential end when no air exists in the air bladder 111. FIG. 6(b) is a plan view showing the vicinity of the circumferential end when air has been supplied to the air bladder 111, and FIG. 6(c) is a cross-sectional view taken along line A-A' in FIG. 6(b).

When air is supplied to the air bladder 111, the air bladder 111 starts to inflate. At this time, in the vicinity of the recess 109h, the air bladder 111 can freely deform toward the recess 109h. For this reason, in region R, the air bladder 111 can inflate significantly toward the measurement site.

Thus, by proving the recess 109h at least one circumferential end of the curler 109, it is possible to sufficiently ensure a force of compressing the measurement site near the circumferential end of the air bladder 111.

Figure 7:
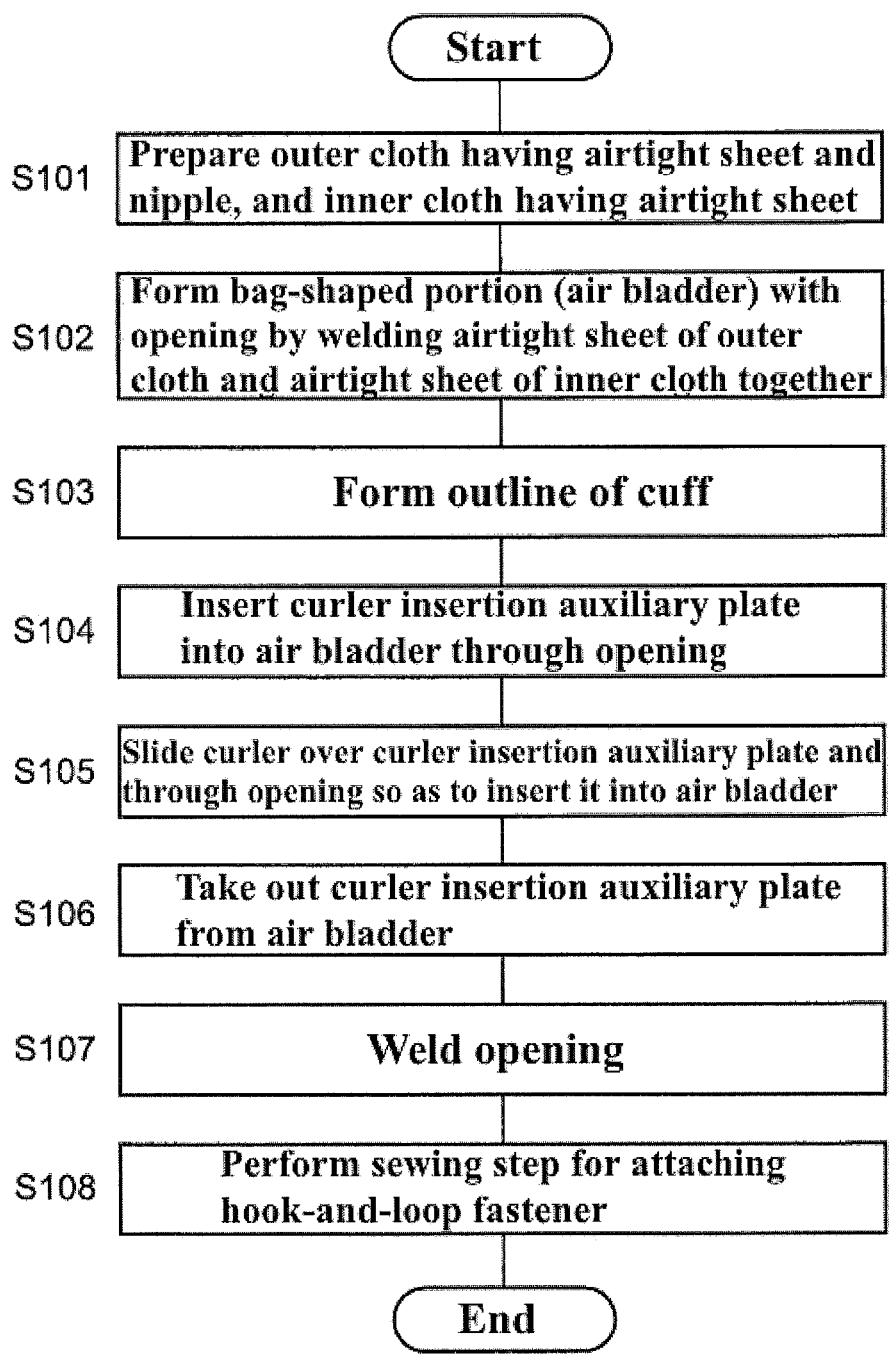
FIG. 7 is a flowchart showing steps for manufacturing the blood pressure measurement cuff according to the first embodiment.

Next, with reference to FIG. 7 and FIGS. 8A to 8H, a method for manufacturing the cuff 100 will be described. FIG. 7 is a flowchart showing steps for manufacturing the cuff 100, and FIGS. 8A to 8H are schematic diagrams showing states of members in the steps of the manufacturing process.

Figure 8A:
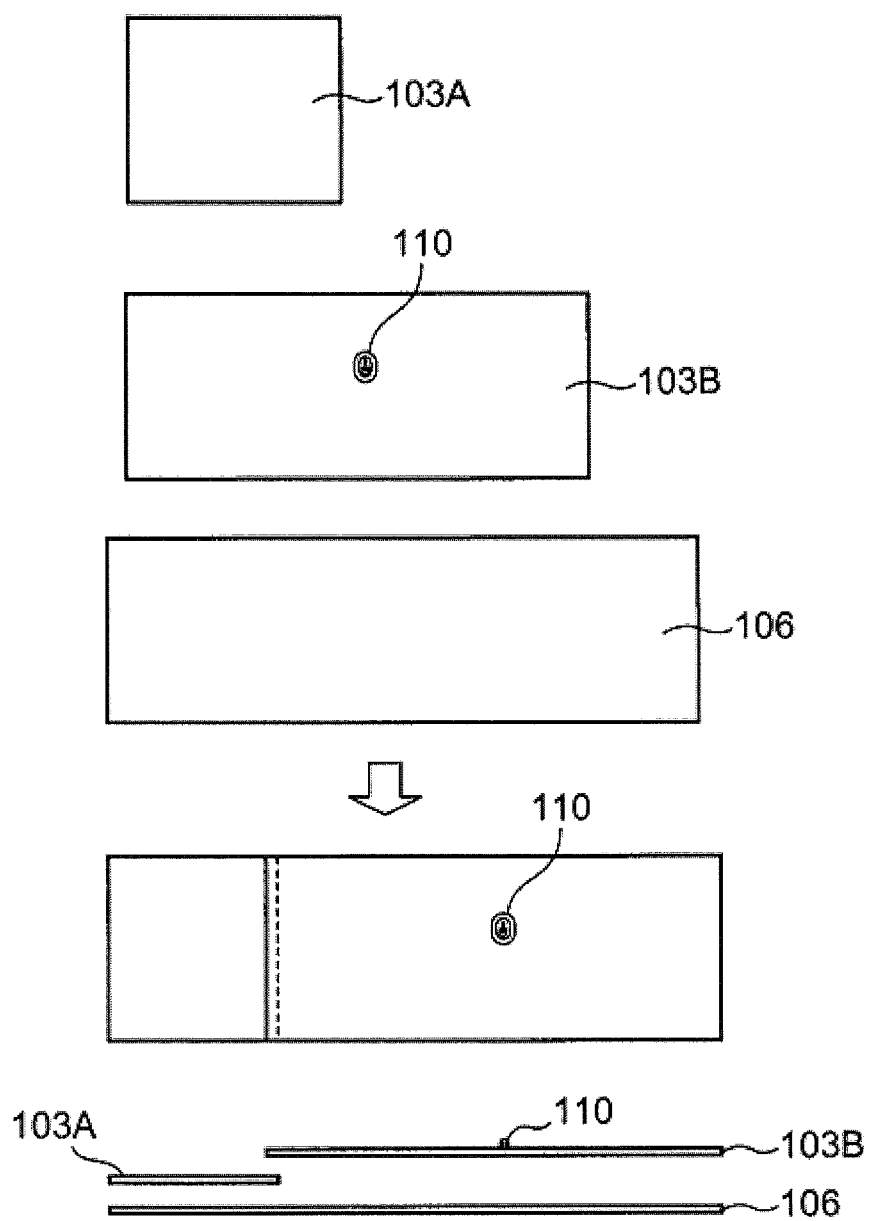
FIG. 8A is a schematic diagram showing a step for manufacturing the blood pressure measurement cuff according to the first embodiment.

First, in step S101, the outer cloth 101A to which the airtight sheet member 102 is attached, or in other words, the outer member 103A, the outer member 103B to which the airtight sheet member 102 and the nipple 110 are attached, and the inner cloth 105 to which the airtight sheet member 104 is attached, or in other words, the inner member 106, are prepared (FIG. 8A).

Figure 8B:
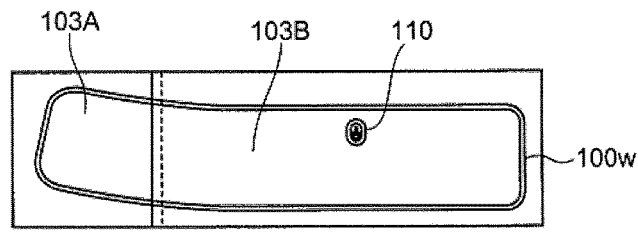
FIG. 8B is a schematic diagram showing a step for manufacturing the blood pressure measurement cuff according to the first embodiment.

Next, in step S102, the airtight sheet member 102 of the outer members 103A and 103B and the airtight sheet member 104 of the inner member 106 are welded together (peripheral edge welded portion 100w (FIG. 8B)) so as to form a bag-shaped portion (air bladder) having an opening (FIG. 8B).

Figure 8C:
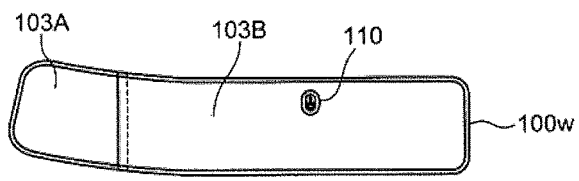
FIG. 8C is a schematic diagram showing a step for manufacturing the blood pressure measurement cuff according to the first embodiment.

Next, in step S103, extraneous members are cut with a die, thus shaping the cuff (FIG. 8C).

Figure 8D:
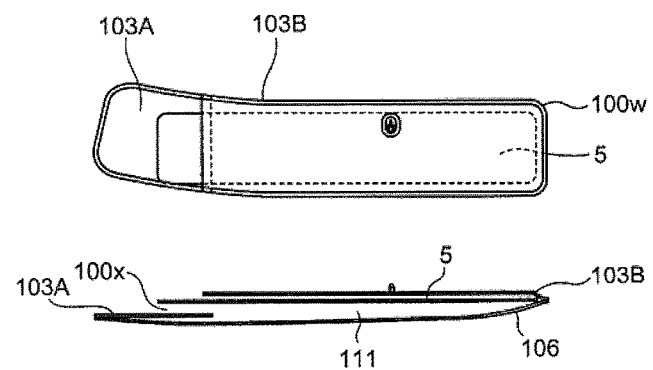
FIG. 8D is a schematic diagram showing a step for manufacturing the blood pressure measurement cuff according to the first embodiment.

Next, in step S104, a plate-shaped curler insertion auxiliary plate 5 is inserted into the air bladder 111 through an unwelded portion (opening 100x (FIG. 8D)) (FIG. 8D).

Figure 8E:
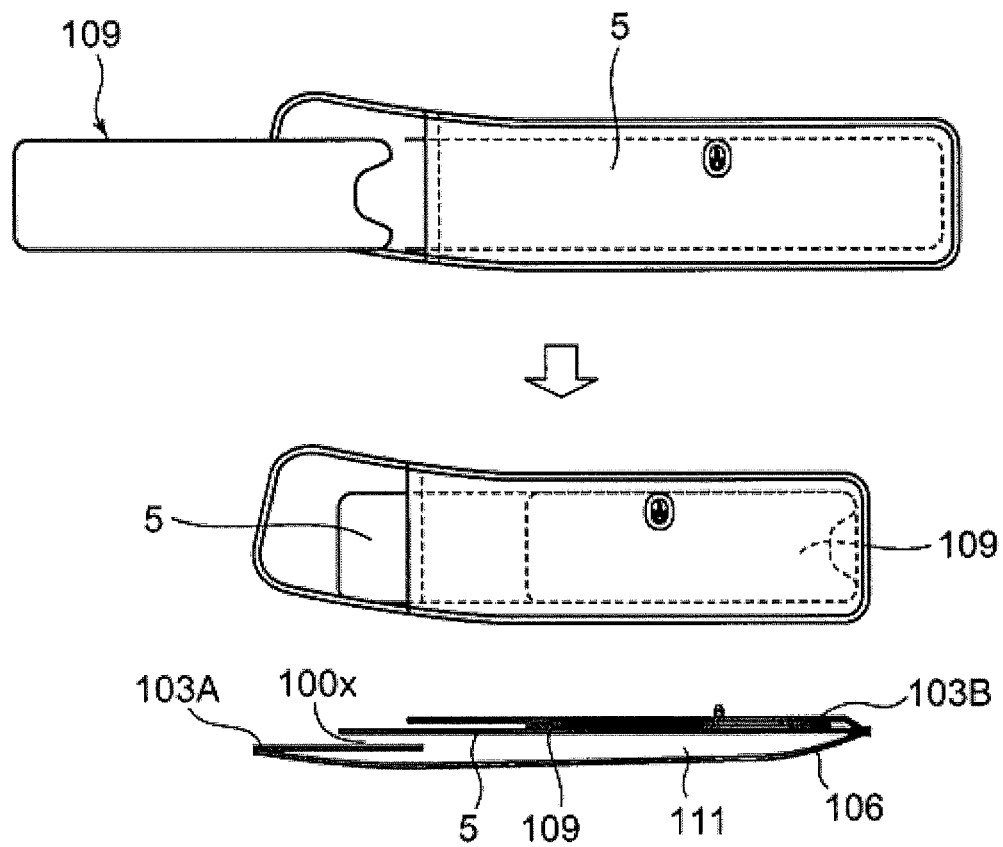
FIG. 8E is a schematic diagram showing a step for manufacturing the blood pressure measurement cuff according to the first embodiment.

Next, in step S105, the curler 109 is pressed to the curler insertion auxiliary plate 5 so as to be elastically deformed into an approximate plate shape, and is slid over the plate 5 so as to be inserted into the air bladder 111 through the opening 100x (FIG. 8E).

Figure 8F:
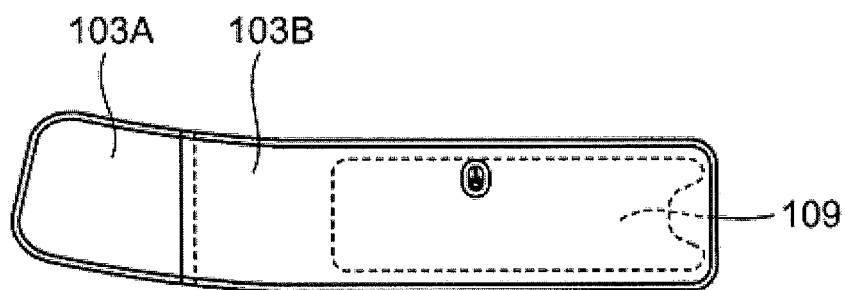
FIG. 8F is a schematic diagram showing a step for manufacturing the blood pressure measurement cuff according to the first embodiment.

Next, in step S106, the curler insertion auxiliary plate 5 is taken out of the air bladder 111 (FIG. 8F).

Note that instead of performing steps S104, S105, and S106, it is possible to prepare two curler insertion auxiliary plates, elastically deform the curler 109 into an approximate plate shape and sandwich it between the two plates, and in that state, insert them into the air bladder 111 through the opening 100x, thereafter removing only the two plates from the air bladder 111.

Figure 8G:
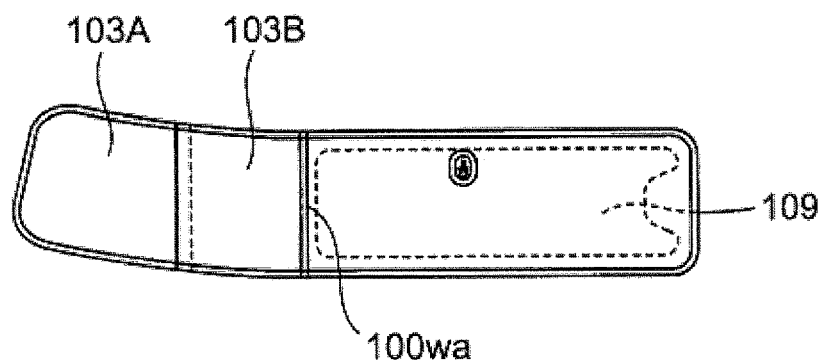
FIG. 8G is a schematic diagram showing a step for manufacturing the blood pressure measurement cuff according to the first embodiment.

Next, in step S107, at the portion that was not welded in step S102 (opening 100x), the airtight sheet member 102 of the outer members 103A and 103B and the airtight sheet member 104 of the inner member 106 are welded together (intermediate welded portion 100wa (FIG. 8G)) so as to close the opening 100x and form the complete air bladder 111 (FIG. 8G).

Figure 8H:
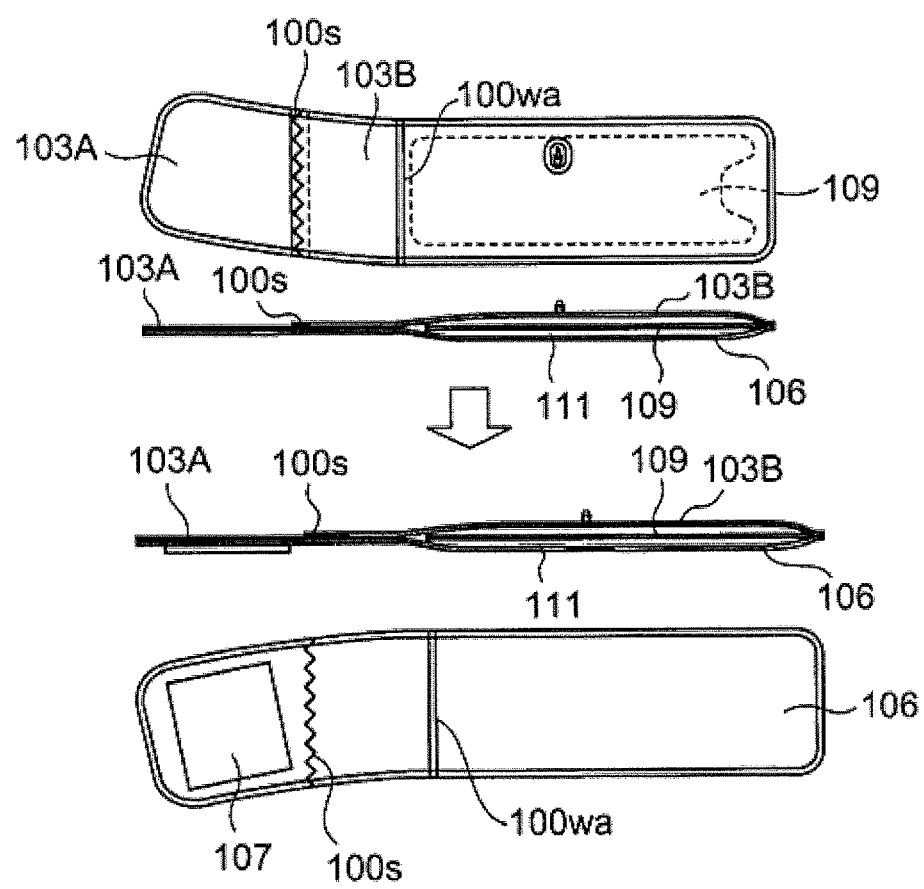
FIG. 8H is a schematic diagram showing a step for manufacturing the blood pressure measurement cuff according to the first embodiment.

Finally, in step S108, a sewing process for attaching the hook-and-loop fastener 107 or the like is performed (FIG. 8H).

As described above, according to the present method for manufacturing, it is possible to manufacture the cuff 100 in an extremely simple manner. In the present method, since the outer cloths 101A and 101B and the inner cloth 105 do not need to be sewn together at the outer perimeter portion of the cuff 100 to form the bag-shaped outer cover, the manufacturing cost can be reduced.

Figures 9A, 9B:
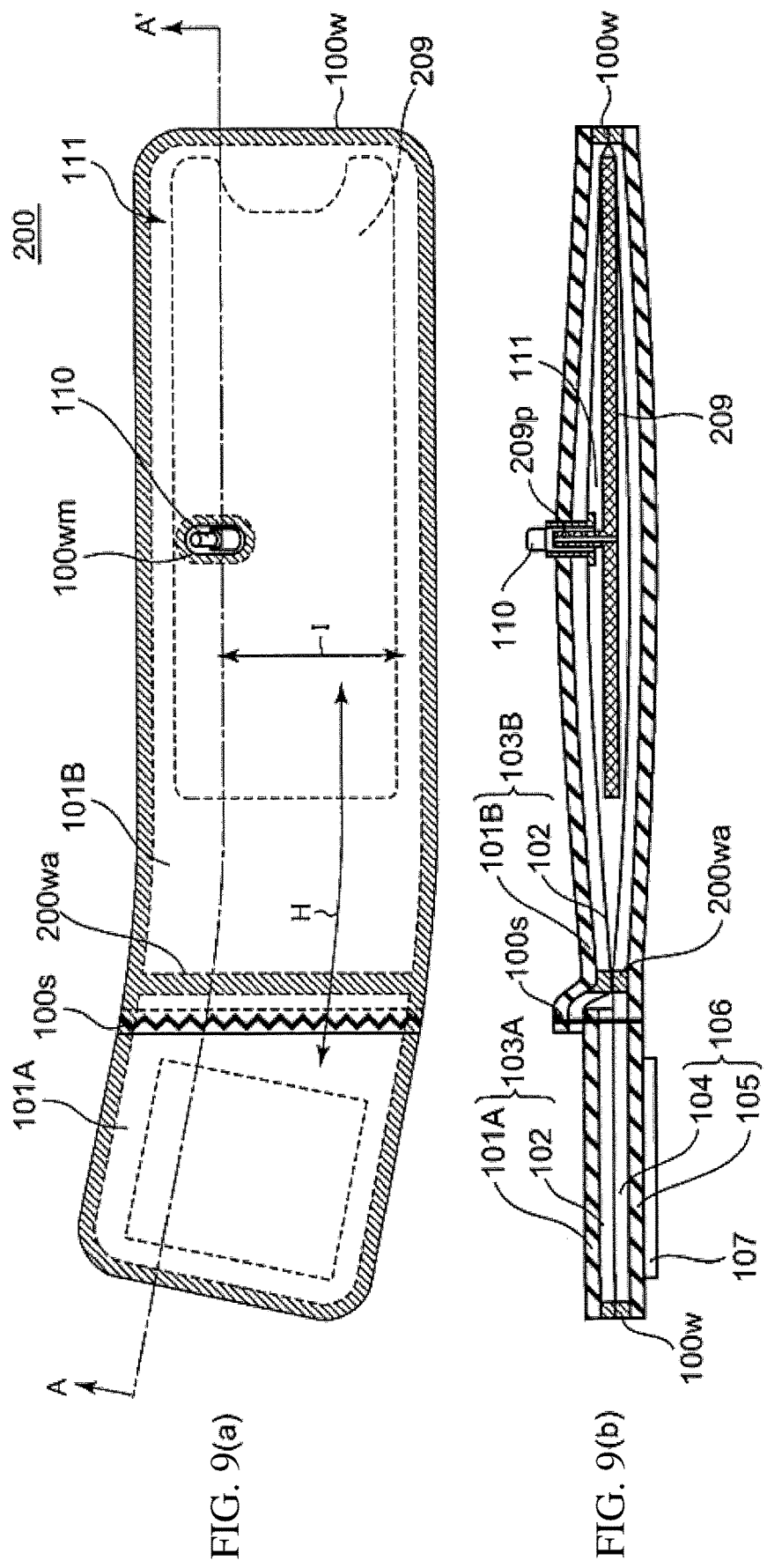
FIG. 9(a) is a plan view of an expanded state of a blood pressure measurement cuff according to a second embodiment.
FIG. 9(b) is a cross-sectional view taken along line A-A' in FIG. 9(a).

Next, a cuff 200 according to a second embodiment of the present invention will be described. FIG. 9(a) is a plan view of an expanded state of the cuff 200 according to the second embodiment of the present invention, and FIG. 9(b) is a cross-sectional view taken along line A-A' in FIG. 9(a). In the description below, description of configurations that are the same as in the preceding embodiment are omitted as appropriate.

In the cuff 200 according to the present embodiment, the airtight sheet member 102 and the airtight sheet member 104 are welded together at the intermediate welded portion 200wa and the peripheral edge welded portion 100w to form the air bladder 111. With the cuff 200, the length in the circumferential direction H of the air bladder 111 (length in the circumferential direction H from the intermediate welded portion 200w to the peripheral edge welded portion 100w on the right end of the diagram) is longer than the length in the circumferential direction H of the curler 109. In other words, this means that the length in the circumferential direction H of the air bladder 111 can be designed independently of the length in the circumferential direction H of the curler 209. Accompanying this, with the cuff 200 according to the present embodiment, for example, a positioning portion is included which fixes the relative positional relationship between the curler 209 and the air bladder 111 in order to prevent the curler 209 from moving around in the air bladder 111 when the user wraps the cuff 200.

As the positioning portion that fixes the relative positional relationship between the curler 209 and the air bladder 111, the cuff 200 includes a protrusion 209p that is formed on the outer surface of the curler 209 and fits into the interior of a nipple 110.

Figure 10:
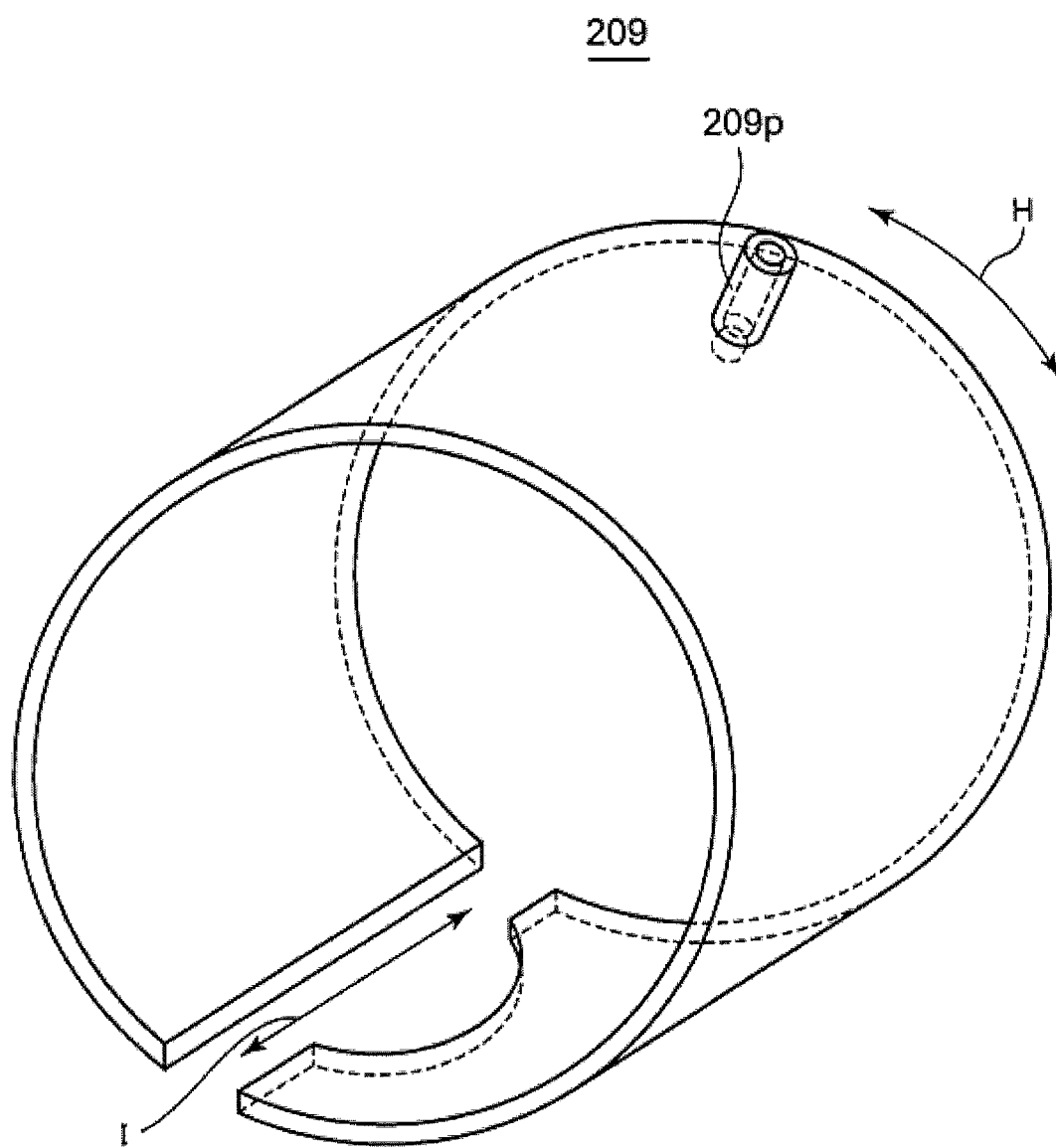
FIG. 10 is a perspective view of a curler for the blood pressure measurement cuff according to the second embodiment.

FIG. 10 is a perspective view of the curler 209. The protrusion 209p that fits into the interior of the nipple 110 is included at a position, on the outer surface of the curler 209, that corresponds to the nipple 110 when arranged inside of the air bladder 111. The position of the curler 209 is fixed in the air bladder 111 due to the effect of the protrusion 209p.

Figure 11:
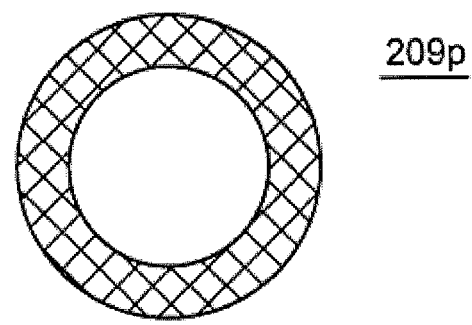
FIG. 11(a) is a diagram showing an example of a cross-sectional shape of a protrusion (positioning portion) of the curler.
FIG. 11(b) is a diagram showing another example of the cross-sectional shape of the protrusion of the curler.
Figure 11:
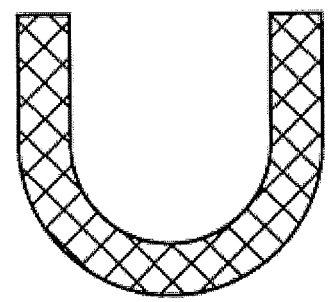

FIG. 11 is a diagram showing the cross-sectional shape of the protrusion 209p. In the example shown in FIG. 11A, the cross-sectional shape of the protrusion 209p is O-shaped, and the interior of the O shape is hollow, which allows air to flow through. In the example shown in FIG. 11B, the cross-sectional shape of a protrusion 209p1 is U-shaped. The cross-sectional shape of the protrusion 209p is not limited thereto, and may be another shape.

Thus, in the cuff 200 according to the second embodiment, a means for positioning the curler 209 in the air bladder 111 is provided. Accordingly, the length in the circumferential direction H of the air bladder 111 can be designed freely, regardless of the length in the circumferential direction H of the curler 209, and the curler 209 is prevented from moving around needlessly in the air bladder 111.

Figure 12:
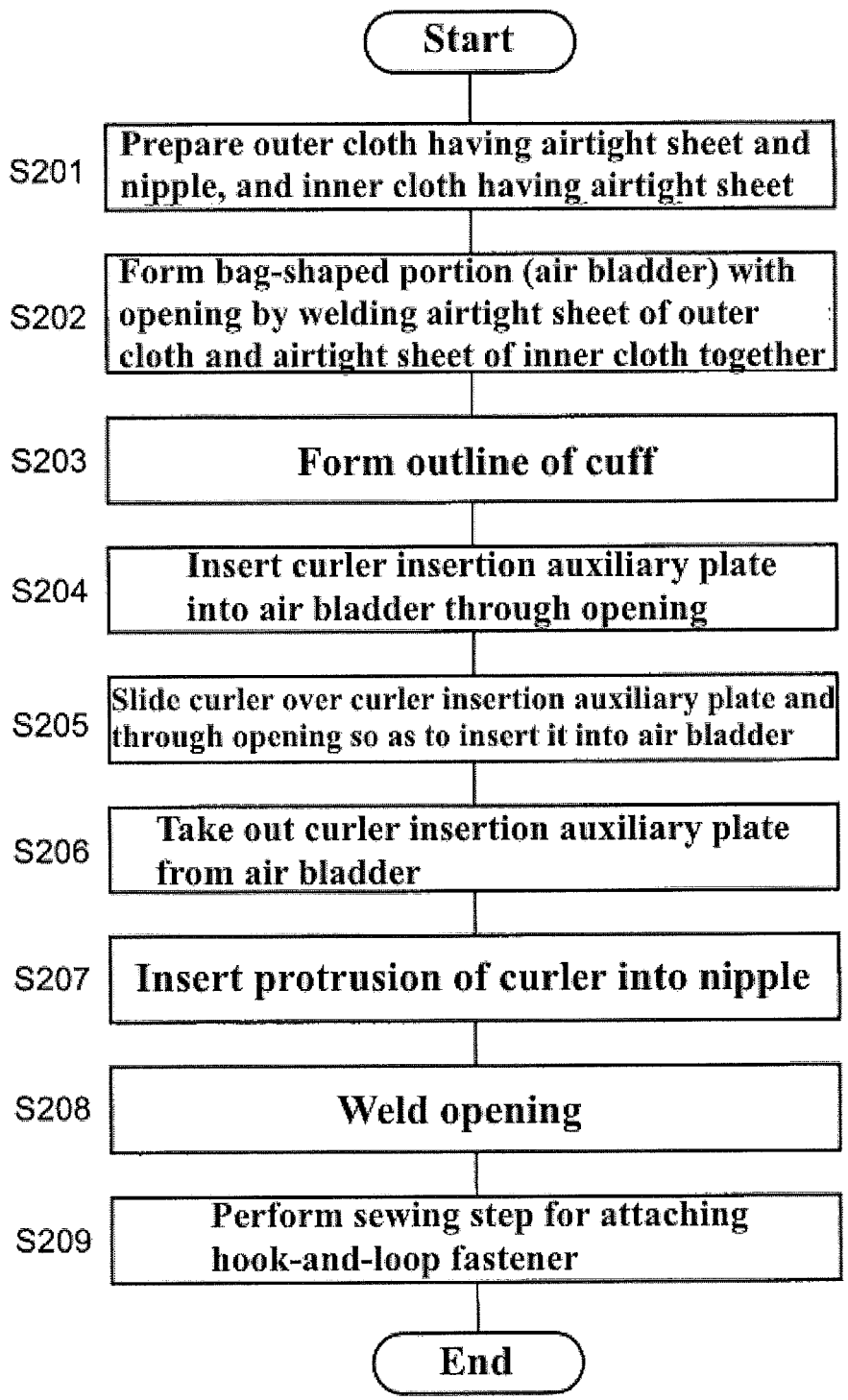
FIG. 12 is a flowchart showing steps for manufacturing the blood pressure measurement cuff according to the second embodiment.

Next, with reference to FIG. 12 and FIGS. 13A to 13H, a method for manufacturing the cuff 200 will be described. FIG. 12 is a flowchart showing steps for manufacturing the cuff 200, and FIGS. 13A to 13H are schematic diagrams showing states of members in the steps of the manufacturing process.

Figure 13A:
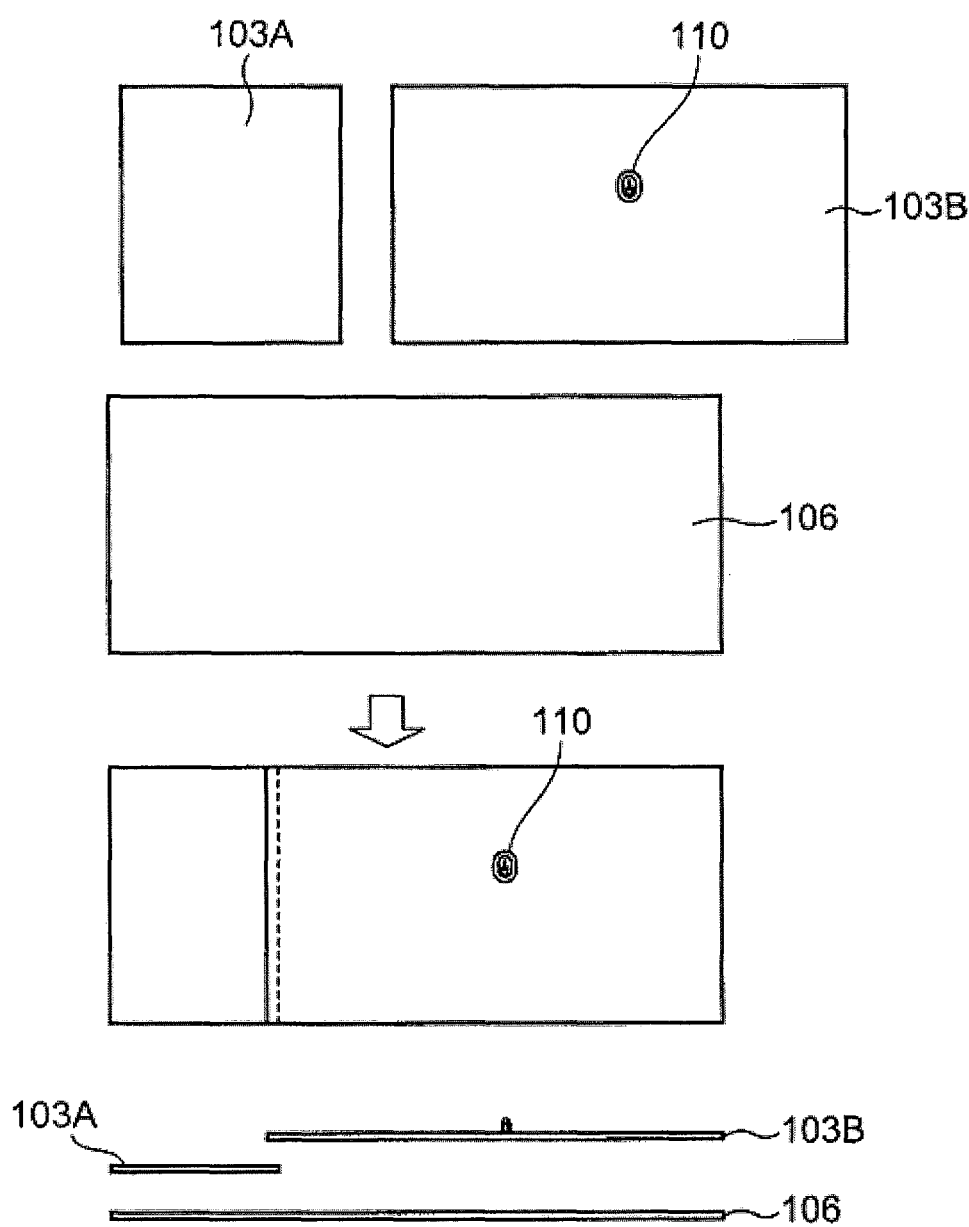
FIG. 13A is a schematic diagram illustrating a step for manufacturing the blood pressure measurement cuff according to the second embodiment.

First, in step S201, the outer cloth 101A to which the airtight sheet member 102 is attached, or in other words, the outer member 103A, the outer member 103B to which the airtight sheet member 102 and the nipple 110 are attached, and the inner cloth 105 to which the airtight sheet member 104 is attached, or in other words, the inner member 106, are prepared (FIG. 13A).

Figure 13B:
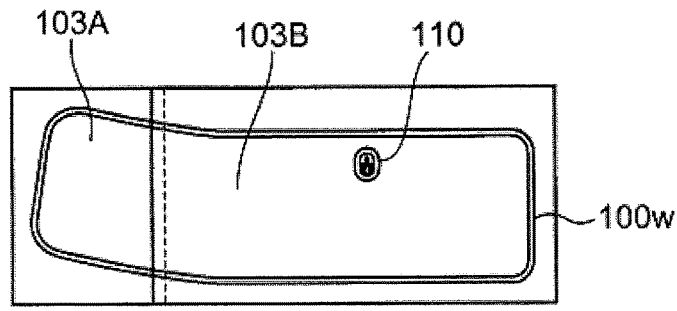
FIG. 13B is a schematic diagram illustrating a step for manufacturing the blood pressure measurement cuff according to the second embodiment.

Next, in step S202, the airtight sheet member 102 of the outer members 103A and 103B and the airtight sheet member 104 of the inner member 106 are welded together (peripheral edge welded portion 100w (FIG. 13B)) so as to form a bag-shaped portion (air bladder) having an opening (FIG. 13B).

Figure 13C:
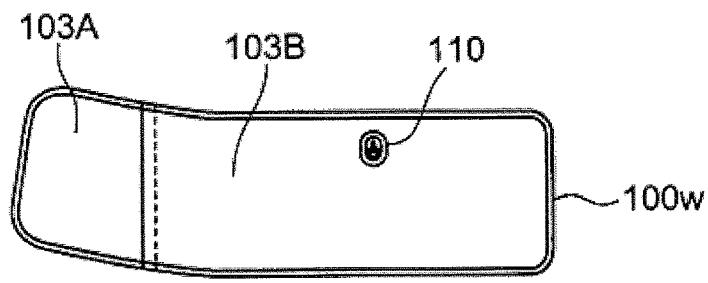
FIG. 13C is a schematic diagram illustrating a step for manufacturing the blood pressure measurement cuff according to the second embodiment.

Next, in step S203, extraneous members are cut with a die, thus forming a cuff (FIG. 13C).

Figure 13D:
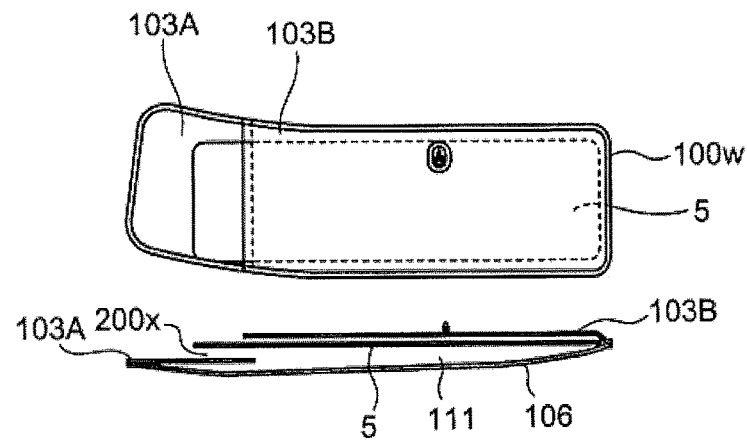
FIG. 13D is a schematic diagram illustrating a step for manufacturing the blood pressure measurement cuff according to the second embodiment.

Next, in step S204, a plate-shaped curler insertion auxiliary plate 5 is inserted into the air bladder 111 through an unwelded portion (opening 200x (FIG. 13D)) (FIG. 13D).

Figure 13E:
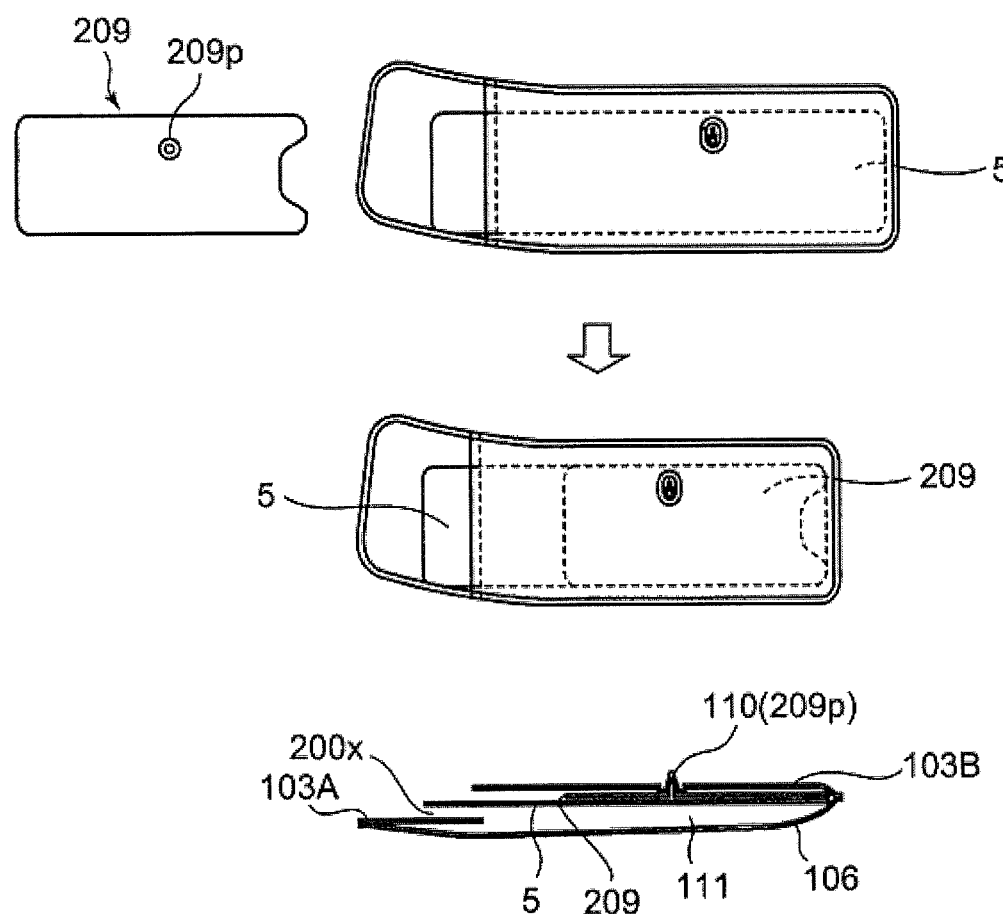
FIG. 13E is a schematic diagram illustrating a step for manufacturing the blood pressure measurement cuff according to the second embodiment.

Next, in step S205, the curler 209, which includes the protrusion 209p on its outer surface, is pressed to the curler insertion auxiliary plate 5 so as to be elastically deformed into an approximate plate shape, and is slid over the plate 5 so as to be inserted into the air bladder 111 through the opening 200x (FIG. 13E).

Figure 13F:
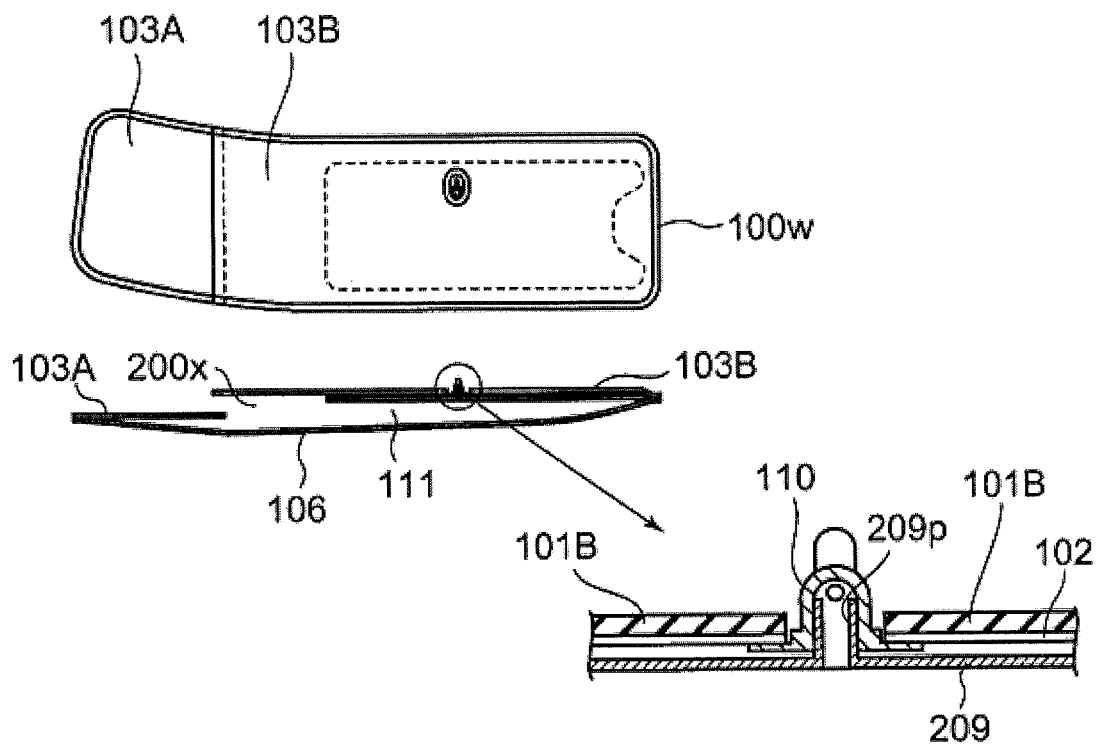
FIG. 13F is a schematic diagram illustrating a step for manufacturing the blood pressure measurement cuff according to the second embodiment.

Next, in step S206, the curler insertion auxiliary plate 5 is taken out of the air bladder 111 (FIG. 13F).

Note that instead of performing steps S204, S205, and S206, it is possible to prepare two curler insertion auxiliary plates, elastically deform the curler 209 into an approximate plate shape and sandwich it between the two plates, and in that state, insert them into the air bladder 111 through the opening 200x, thereafter removing only the two plates from the air bladder 111.

Next, in step S207, the protrusion 209p of the curler 209 is fitted into the interior of the nipple 110 (FIG. 13F).

Figure 13G:
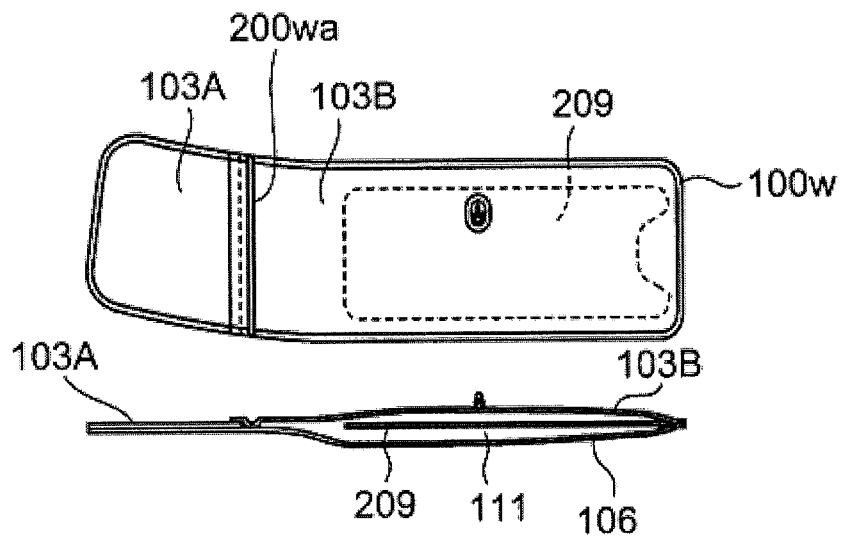
FIG. 13G is a schematic diagram illustrating a step for manufacturing the blood pressure measurement cuff according to the second embodiment.

Next, in step S208, at the portion that was not welded in step S202 (opening 200x), the airtight sheet member 102 of the outer members 103A and 103B and the airtight sheet member 104 of the inner member 106 are welded together (intermediate welded portion 200wa (FIG. 13G)) so as to close the opening 200x and form the complete air bladder 111 (FIG. 13G).

Figure 13H:
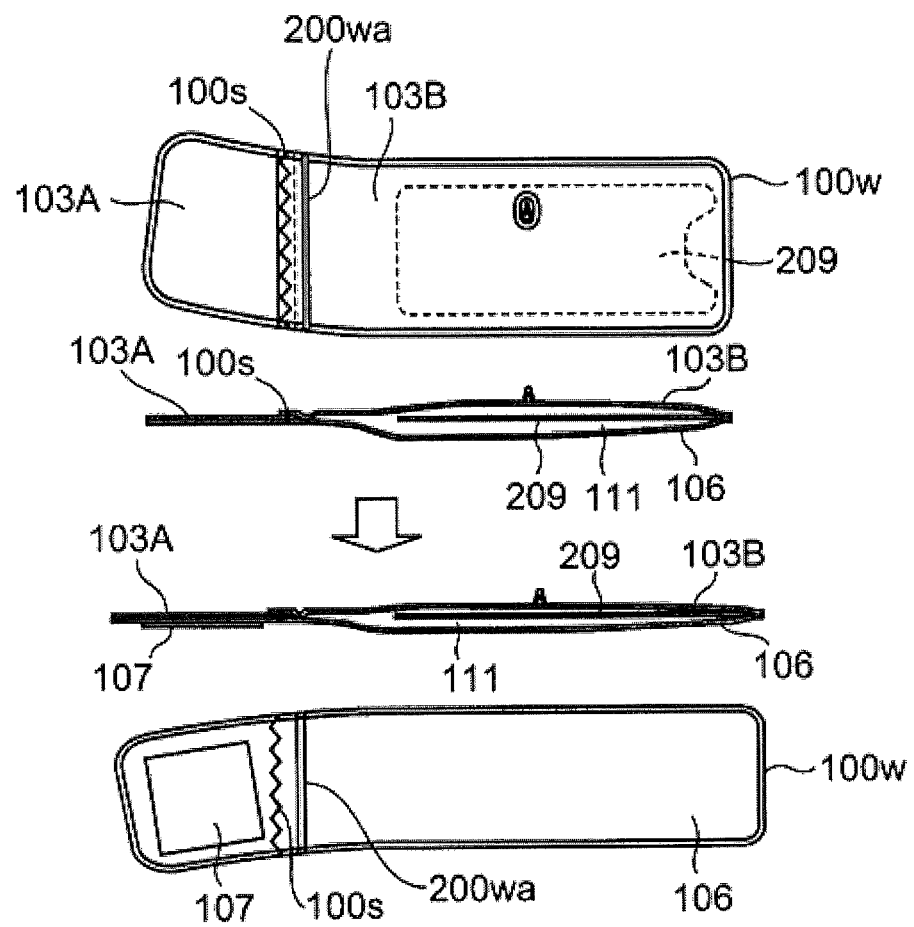
FIG. 13H is a schematic diagram illustrating a step for manufacturing the blood pressure measurement cuff according to the second embodiment.

Finally, in step S209, a sewing process for attaching the hook-and-loop fastener 107 or the like is performed (FIG. 13H).

As described above, according to the present method for manufacturing, it is possible to manufacture the cuff 200 in an extremely simple manner. In the present method, since the outer cloths 101A and 101B and the inner cloth 105 do not need to be sewn together at the outer perimeter portion of the cuff 200 to form the bag-shaped outer cover, the manufacturing cost can be reduced.

Next, a cuff 300 according to a third embodiment of the present invention will be described. FIG. 14(a) is a plan view of an expanded state of the cuff 300 according to the third embodiment of the present invention, and FIG. 14(b) is a cross-section taken along line A-A' in FIG. 14(a). In the description below, description of configurations that are the same as in the preceding embodiment are omitted as appropriate.

In the cuff 300 according to the present embodiment, similarly to the cuff according to the preceding embodiment, the airtight sheet member 102 and the airtight sheet member 104 are welded together at the intermediate welded portion 200wa and the circumferential edge welded portion 100w to form the air bladder 111. With the cuff 300, similarly to the cuff 200, the length in the circumferential direction H of the air bladder 111 can be designed independently of the length in the circumferential direction H of the curler 109. Accompanying this, the cuff 300 according to the present embodiment includes, as a positioning portion, a curler fixing sheet member 301. The curler fixing sheet member 301 is attached to the inner surface of the air bladder 111 and the curler 109 and positions the curler 109 with respect to the air bladder 111. The fixing of the curler fixing sheet member 301 and the inner surface of the air bladder 111 is performed using double-sided adhesive tape 302. The fixing of the curler fixing sheet member 301 and the curler 109 is also performed using double-sided adhesive tape 303. Note that with the cuff 300, there is no need to include a protrusion on the outer surface of the curler 109 as with the curler 209 in the second embodiment.

Figure 15:
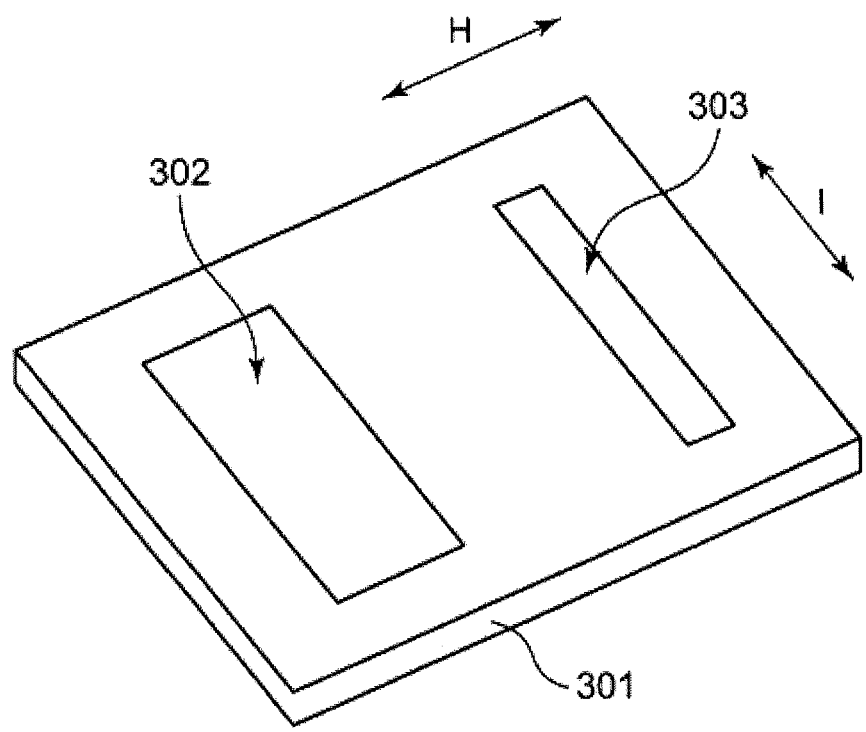
FIG. 15 is a perspective view of a positioning portion according to the third embodiment.

FIG. 15 is a perspective view of the curler fixing sheet member 301. The curler fixing sheet member 301 is a PVC sheet, for example. The double-sided adhesive tape 302 and 303 is adhered to the upper surface of the curler fixing sheet member 301.

Thus, in the cuff 300 according to the third embodiment, a means for positioning the curler 109 in the air bladder 111 is provided. Accordingly, the length in the circumferential direction H of the air bladder 111 can be designed freely, regardless of the length in the circumferential direction H of the curler 109, and the curler 109 is prevented from moving around needlessly in the air bladder 111.

Figure 16:
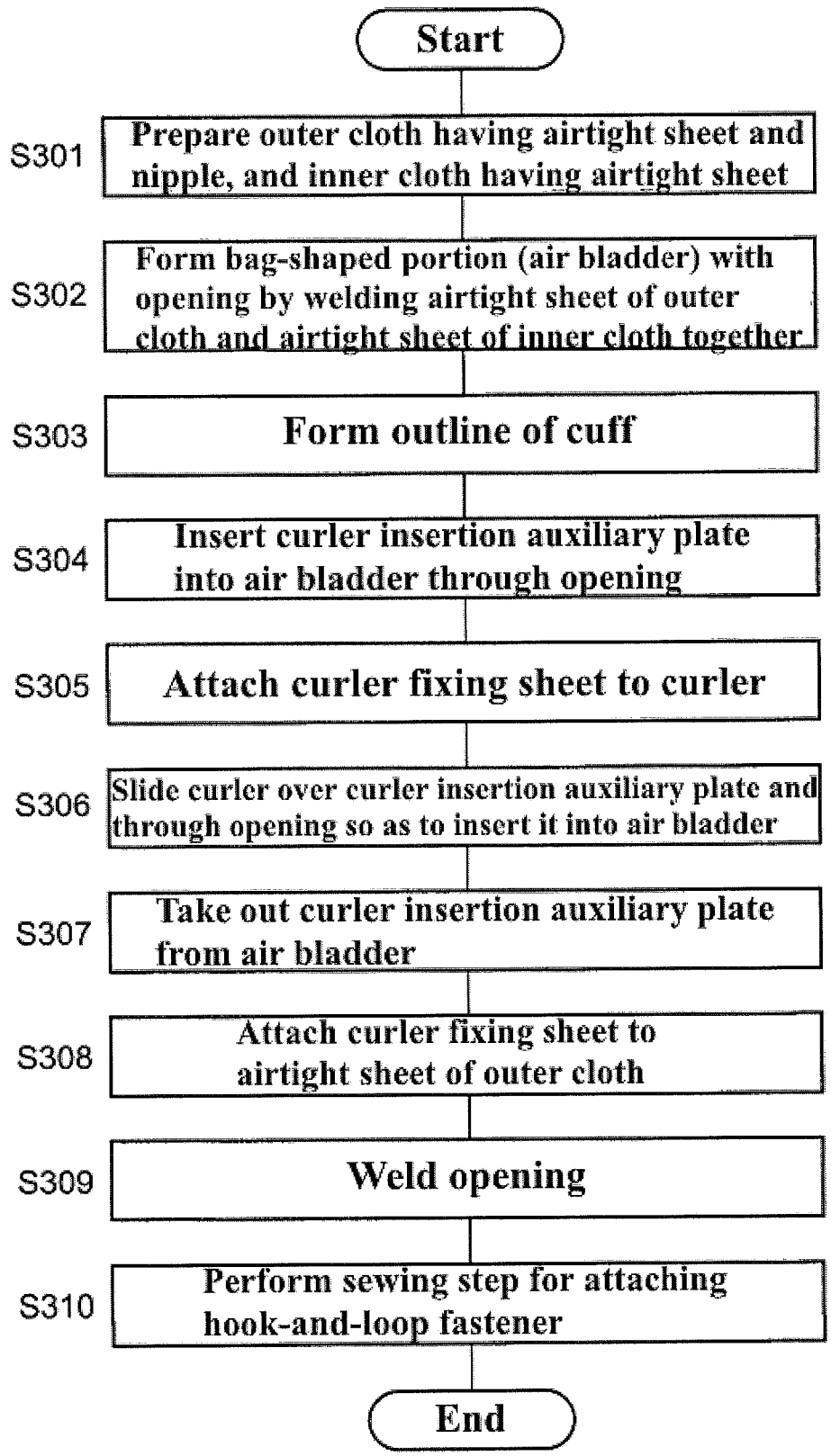
FIG. 16 is a flowchart showing steps for manufacturing the blood pressure measurement cuff according to the third embodiment.

Next, with reference to FIG. 16 and FIGS. 17A to 17I, a method for manufacturing the cuff 300 will be described. FIG. 16 is a flowchart showing steps for manufacturing the cuff 300, and FIGS. 17A to 17I are schematic diagrams showing states of members in the steps of the manufacturing process.

Figure 17A:
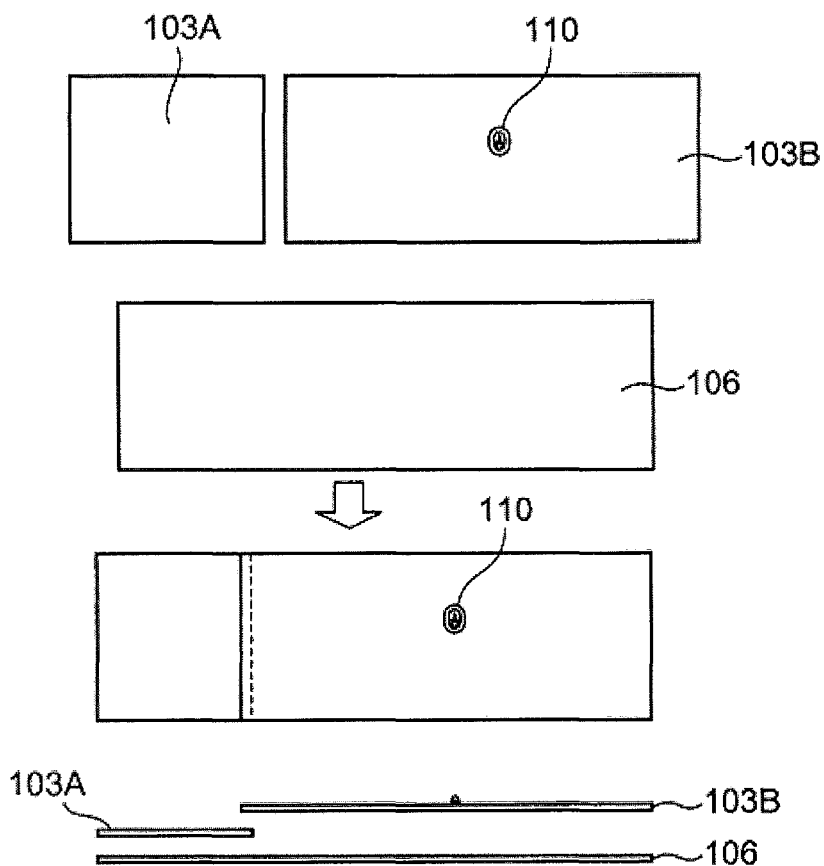
FIG. 17A is a schematic diagram illustrating a step for manufacturing the blood pressure measurement cuff according to the third embodiment.

First, in step S301, the outer cloth 101A to which the airtight sheet member 102 is attached, or in other words, the outer member 103A, the outer member 103B to which the airtight sheet member 102 and the nipple 110 are attached, and the inner cloth 105 to which the airtight sheet member 104 is attached, or in other words, the inner member 106, are prepared (FIG. 17A).

Figure 17B:
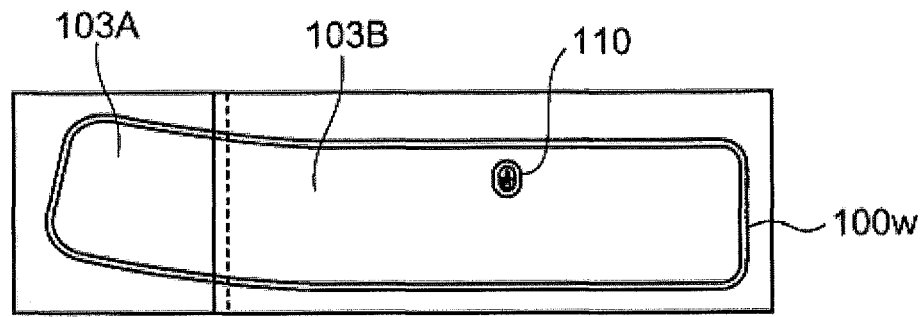
FIG. 17B is a schematic diagram illustrating a step for manufacturing the blood pressure measurement cuff according to the third embodiment.

Next, in step S302, the airtight sheet member 102 of the outer members 103A and 103B and the airtight sheet member 104 of the inner member 106 are welded together (peripheral edge welded portion 100w (FIG. 17B)) so as to form a bag-shaped portion (air bladder) having an opening (FIG. 17B).

Figure 17C:
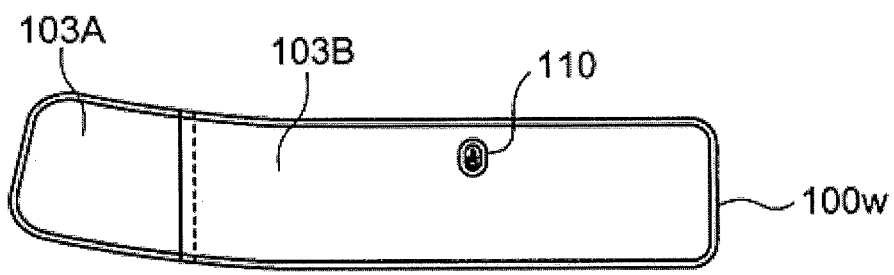
FIG. 17C is a schematic diagram illustrating a step for manufacturing the blood pressure measurement cuff according to the third embodiment.

Next, in step S303, extraneous members are cut with a die, thus forming a cuff (FIG. 17C).

Figure 17D:
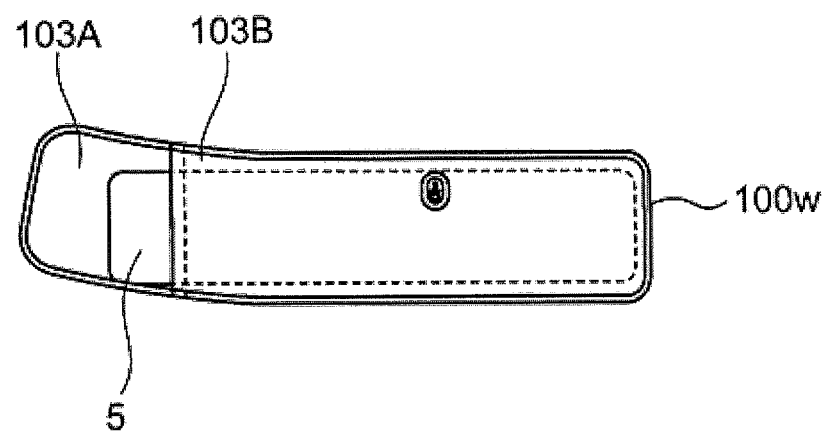
FIG. 17D is a schematic diagram illustrating a step for manufacturing the blood pressure measurement cuff according to the third embodiment.

Next, in step S304, a plate-shaped curler insertion auxiliary plate 5 is inserted into the air bladder 111 through the unwelded portion (opening 300x (FIG. 17F)) (FIG. 17D).

Figure 17E:
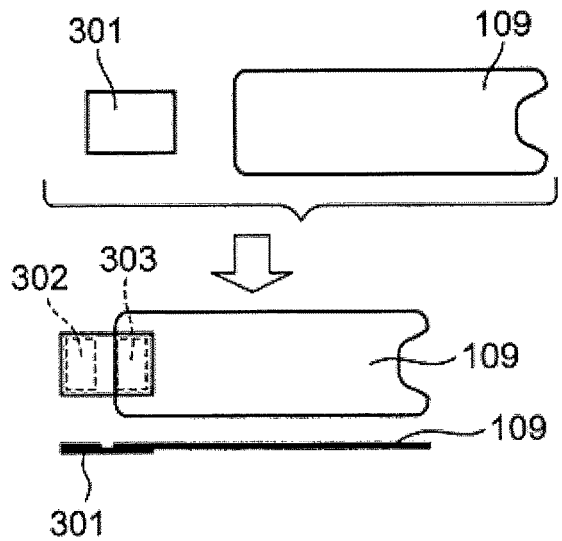
FIG. 17E is a schematic diagram illustrating a step for manufacturing the blood pressure measurement cuff according to the third embodiment.

Next, in step S305, the double-sided adhesive tape 303 is used to attach the curler fixing sheet member 301 to the curler 109 (FIG. 17E).

Figure 17F:
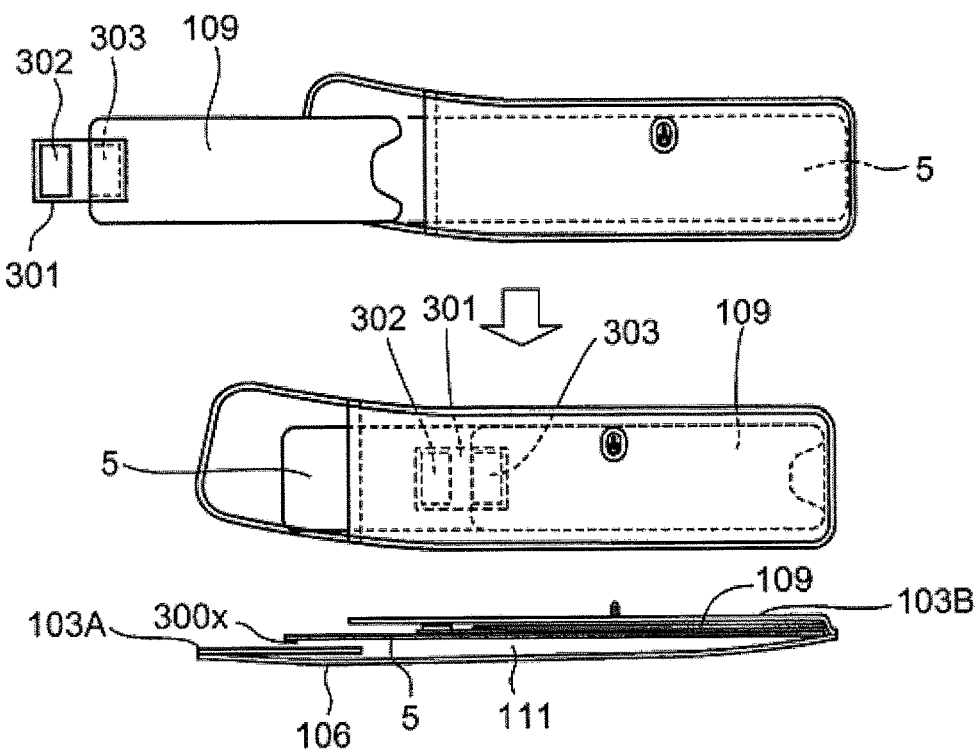
FIG. 17F is a schematic diagram illustrating a step for manufacturing the blood pressure measurement cuff according to the third embodiment.

Next, in step S306, the curler 109, to which the curler fixing sheet member 301 is attached, is pressed to the curler insertion auxiliary plate 5 so as to be elastically deformed into an approximate plate shape, and is slid over the plate 5 so as to be inserted into the air bladder 111 through the opening 300x (FIG. 17F).

Figure 17G:
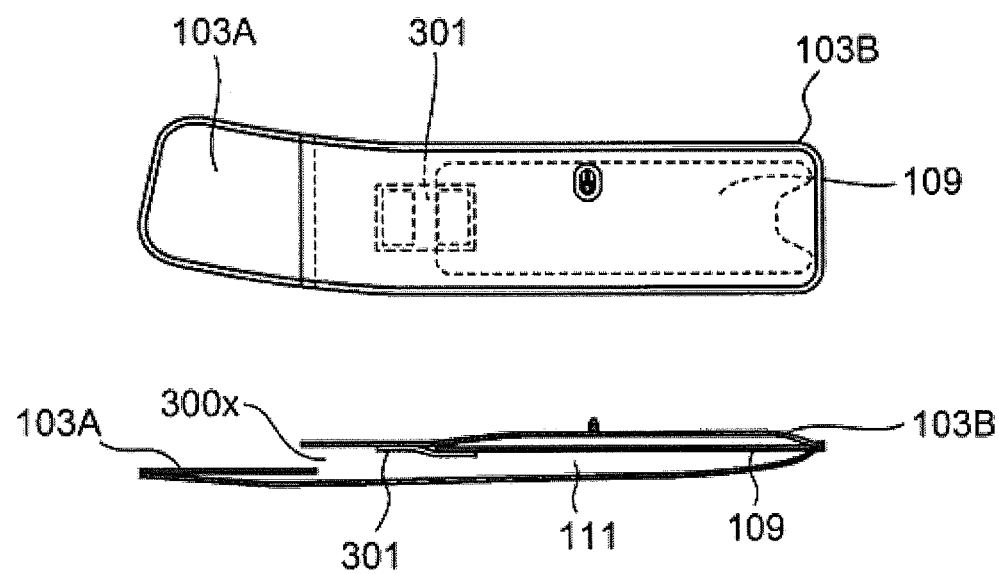
FIG. 17G is a schematic diagram illustrating a step for manufacturing the blood pressure measurement cuff according to the third embodiment.

Next, in step S307, the curler insertion auxiliary plate 5 is taken out of the air bladder 111 (FIG. 17G).

Note that instead of performing steps S304, S306, and S307, it is possible to prepare two curler insertion auxiliary plates, elastically deform the curler 109 into an approximate plate shape and sandwich it between the two plates, and in that state, insert them into the air bladder 111 through the opening 300x, thereafter removing only the two plates from the air bladder 111.

Next, in step S308, the double-sided adhesive tape 302 is used to attach the curler fixing sheet member 301 to the inner surface of the air bladder 111 (FIG. 17G).

Figure 17H:
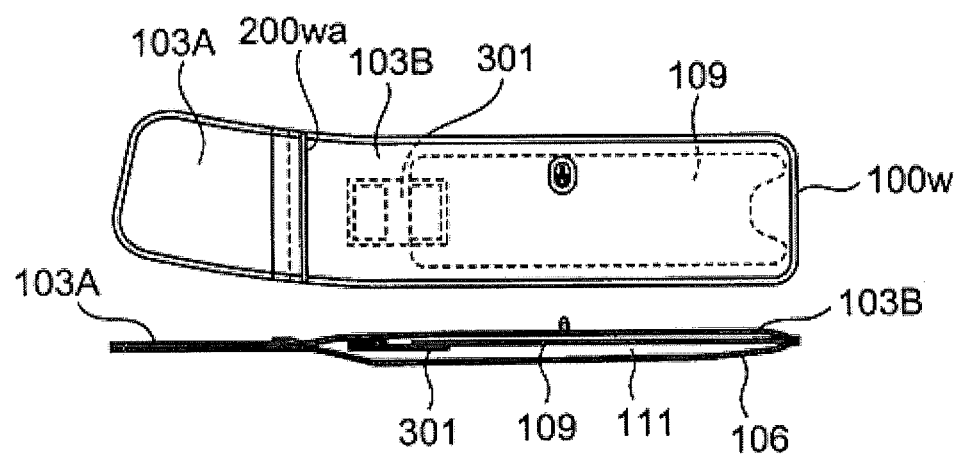
FIG. 17H is a schematic diagram illustrating a step for manufacturing the blood pressure measurement cuff according to the third embodiment.

Next, in step S309, at the portion that was not welded in step S302 (opening 300x), the airtight sheet member 102 of the outer members 103A and 103B and the airtight sheet member 104 of the inner member 106 are welded together (intermediate welded portion 200wa (FIG. 17H)) so as to close the opening 300x and form the complete air bladder 111 (FIG. 17H).

Figure 17I:
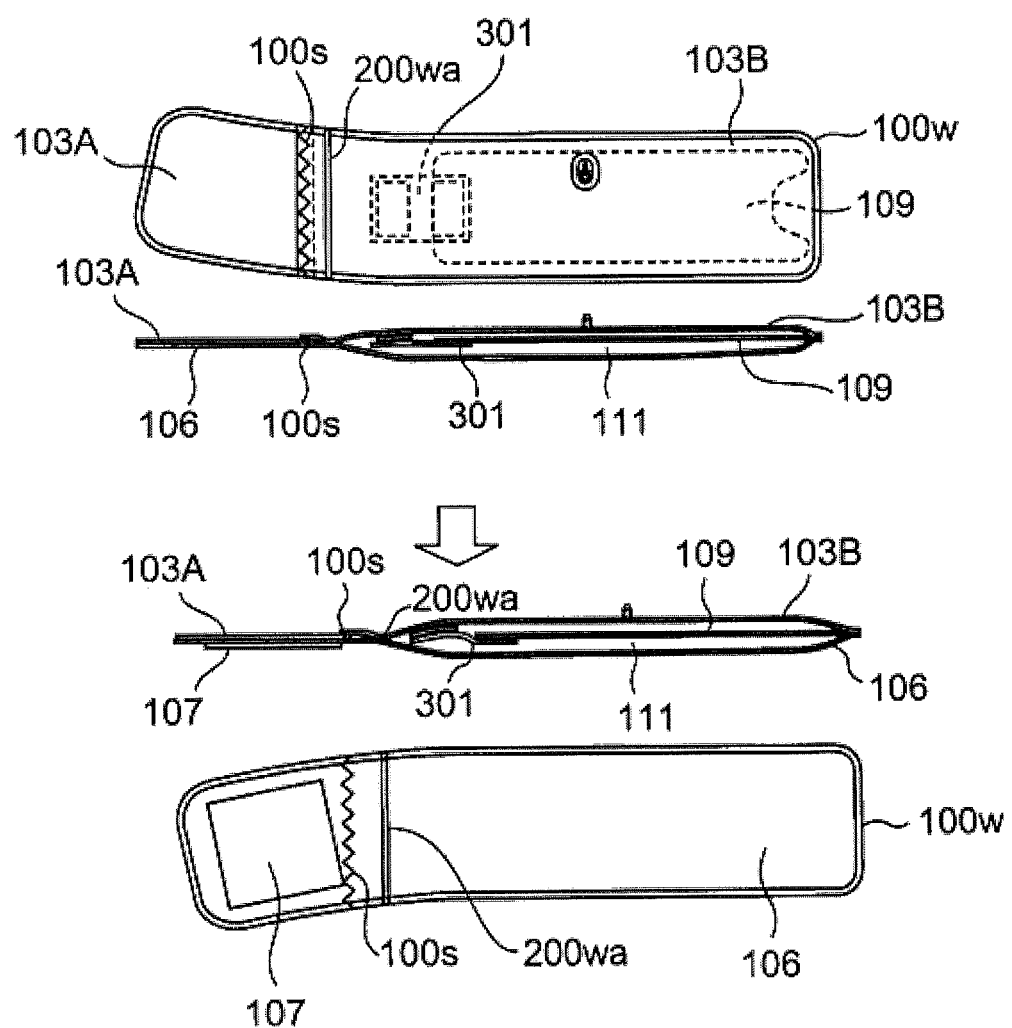
FIG. 17I is a schematic diagram illustrating a step for manufacturing the blood pressure measurement cuff according to the third embodiment.

Finally, in step S310, a sewing process for attaching the hook-and-loop fastener 107 or the like is performed (FIG. 17I).

As described above, according to the present method for manufacturing, it is possible to manufacture the cuff 300 in an extremely simple manner. In the present method, since the outer cloths 101A and 101B and the inner cloth 105 do not need to be sewn together at the outer perimeter portion of the cuff 300 to form the bag-shaped outer cover, the manufacturing cost can be reduced.

Next, a cuff 400 according to a fourth embodiment of the present invention will be described. FIG. 18(a) is a plan view of an expanded state of the cuff 400 according to the fourth embodiment of the present invention, and FIG. 18(b) is a cross-section taken along line A-A' in FIG. 18(a). In the description below, description of configurations that are the same as in the preceding embodiment are omitted as appropriate.

In the cuff 400 according to the present embodiment, similarly to the cuff according to the preceding embodiment, the airtight sheet member 102 and the airtight sheet member 104 are welded together at the intermediate welded portion 200wa and the peripheral edge welded portion 100w to form the air bladder 111. With the cuff 400, similarly to the cuffs 200 and 300, the length in the circumferential direction H of the air bladder 111 can be designed independently of the length in the circumferential direction H of the curler 109. Accompanying this, the cuff 400 according to the present embodiment includes, as a positioning portion, a curler fixing sheet member 401. The curler fixing sheet member 401 is attached to the air bladder 111 welded to the peripheral edge portion in the circumferential direction H of the air bladder 111 (peripheral edge welded portion 100wb) while being sandwiched between the airtight sheet member 102 and the airtight sheet member 104 and, and the curler 109 is positioned with respect to the air bladder 111 by attaching the curler fixing sheet member 401 to the curler 109 with the double-sided adhesive tape 402. Note that with the cuff 400, similarly to the cuff 300, a protrusion does not need to be included on the outer surface of the curler 109 as with the curler 209 in the second embodiment.

Figure 19:
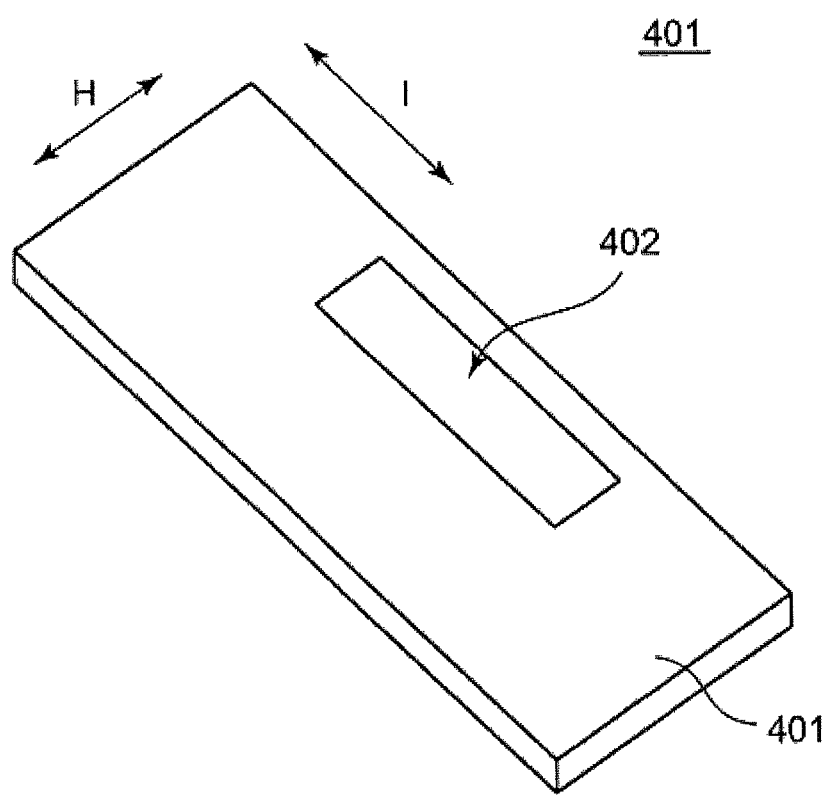
FIG. 19 is a perspective view of a positioning portion according to the fourth embodiment.

FIG. 19 is a perspective view of the curler fixing sheet member 401. The curler fixing sheet member 401 is a PVC sheet, for example. Double-sided adhesive tape 402 is adhered to the upper surface of the curler fixing sheet member 401.

Thus, in the cuff 400 according to the fourth embodiment, a means for positioning the curler 109 in the air bladder 111 is provided. Accordingly, the length in the circumferential direction H of the air bladder 111 can be designed freely, regardless of the length in the circumferential direction H of the curler 109, and the curler 109 is prevented from moving around needlessly in the air bladder 111.

Figure 20:
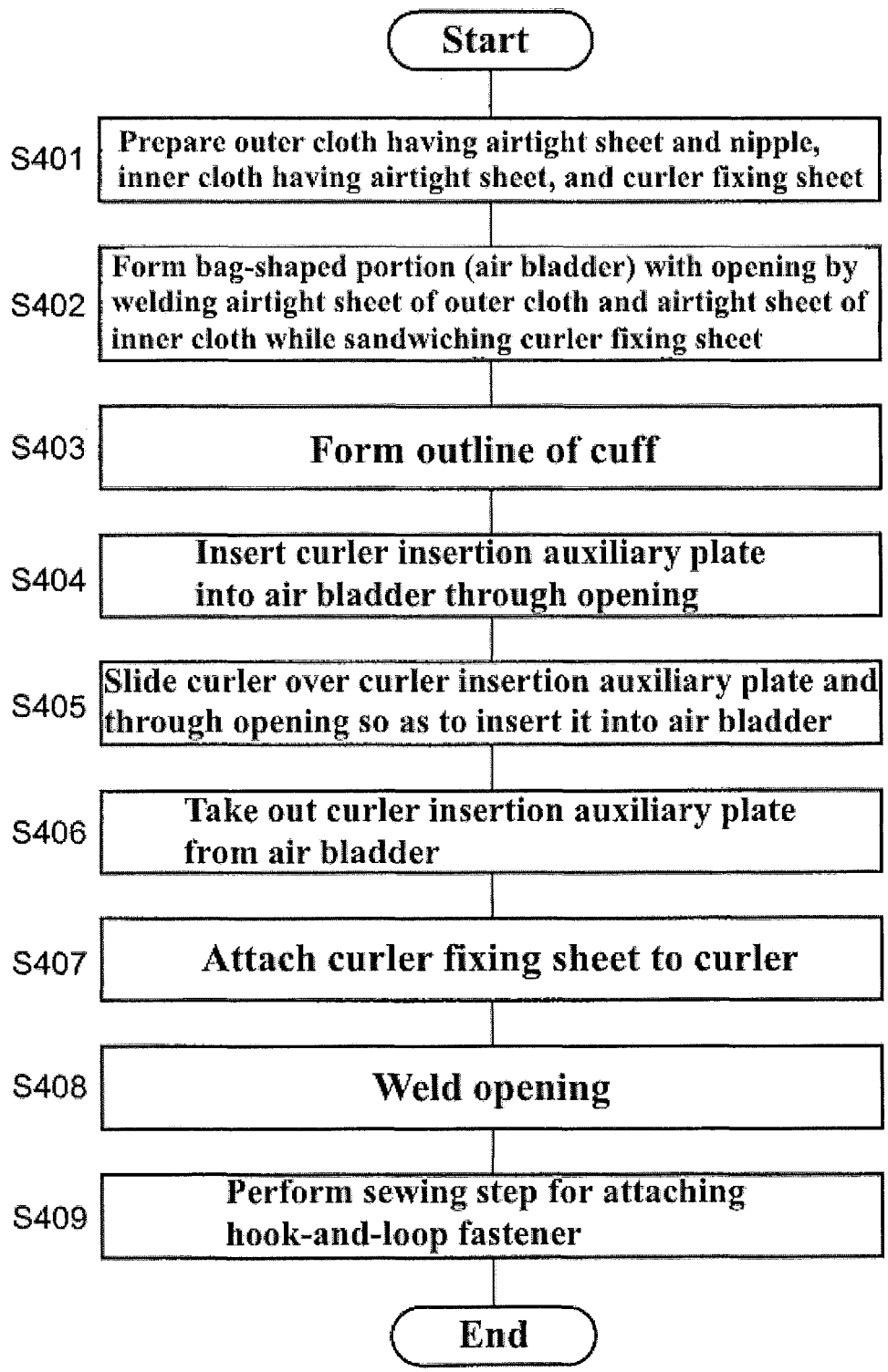
FIG. 20 is a flowchart showing steps for manufacturing the blood pressure measurement cuff according to the fourth embodiment.

Next, with reference to FIG. 20 and FIGS. 21A to 21G a method for manufacturing the cuff 400 will be described. FIG. 20 is a flowchart showing steps for manufacturing the cuff 400, and FIGS. 21A to 21G are schematic diagrams showing states of members in the steps of the manufacturing process.

Figure 21A:
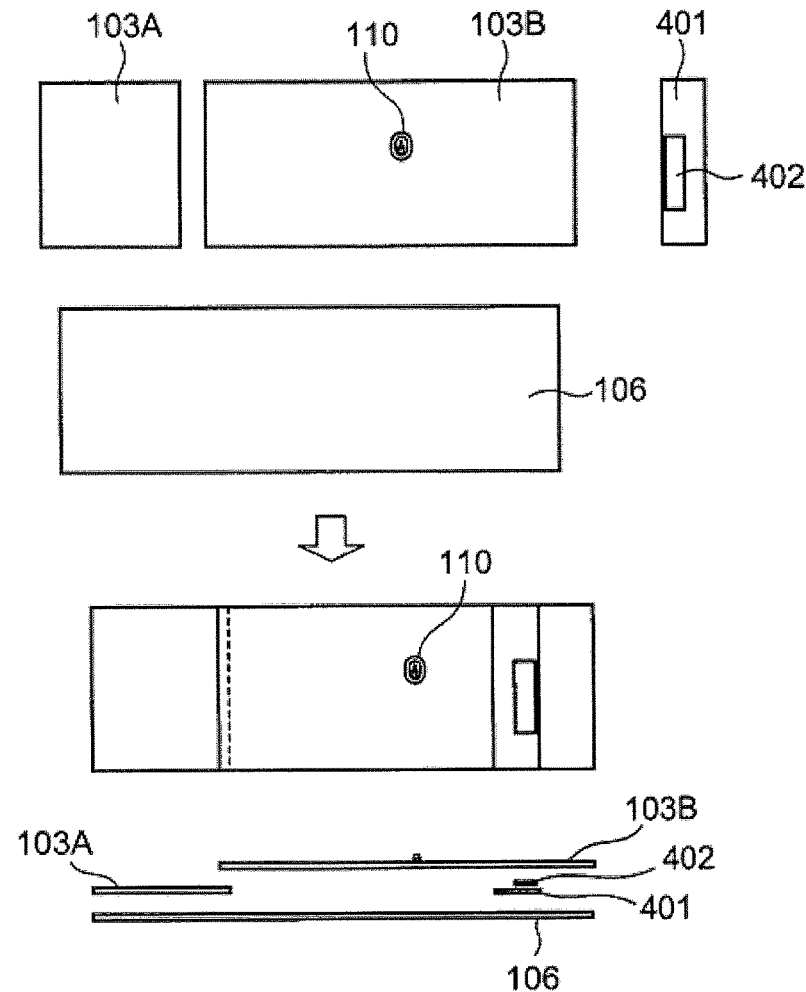
FIG. 21A is a schematic diagram illustrating a step for manufacturing the blood pressure measurement cuff according to the fourth embodiment.

First, in step S401, the outer cloth 101A to which the airtight sheet member 102 is attached, or in other words, the outer member 103A, the outer member 103B to which the airtight sheet member 102 and the nipple 110 are attached, the inner cloth 105 to which the airtight sheet member 104 is attached, or in other words, the inner member 106, and the curler fixing sheet member 401 to which the double-sided adhesive tape 402 is attached, are prepared (FIG. 21A).

Figure 21B:
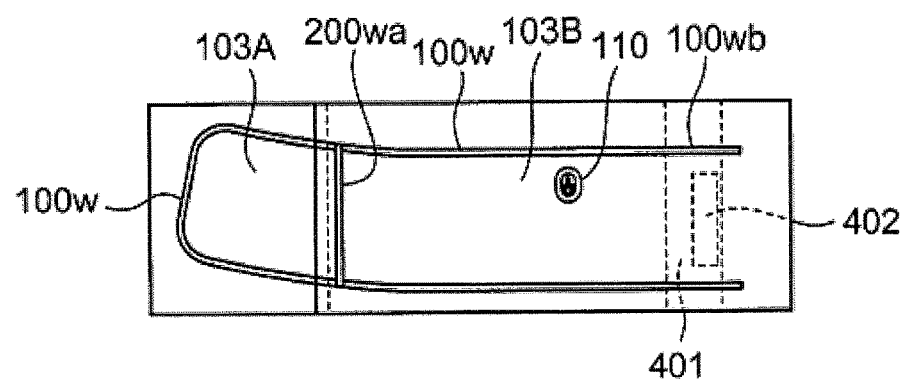
FIG. 21B is a schematic diagram illustrating a step for manufacturing the blood pressure measurement cuff according to the fourth embodiment.

Next, in step S402, the airtight sheet member 102 of the outer members 103A and 103B and the airtight sheet member 104 of the inner member 106 are welded together while sandwiching the curler fixing sheet member 401 at the edge portion in the circumferential direction of the cuff (air bladder 111) (peripheral edge welded portion 100w, intermediate welded portion 200wa, peripheral edge welded portion 100wb (FIG. 21B)) so as to form a bag-shaped portion (air bladder) having an opening (FIG. 21B). In the present step, the opening (400x (FIG. 21D)) is provided on the circumferential end of the cuff 400 (end on the right side of the cuff in FIG. 21B).

Figure 21C:
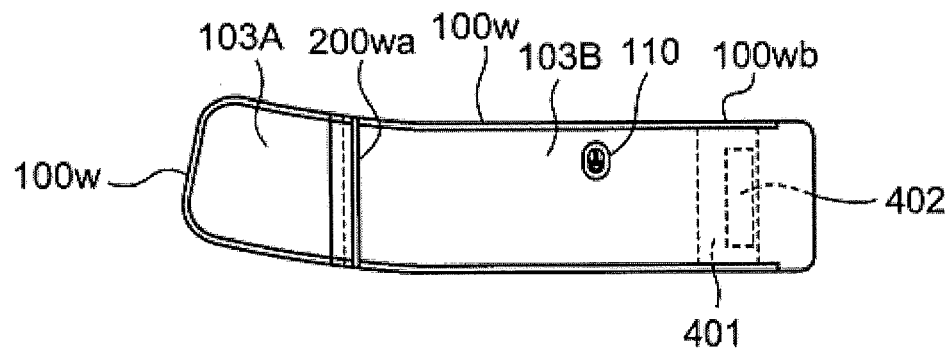
FIG. 21C is a schematic diagram illustrating a step for manufacturing the blood pressure measurement cuff according to the fourth embodiment.

Next, in step S403, extraneous members are cut with a die, thus forming a cuff (FIG. 21C).

Figure 21D:
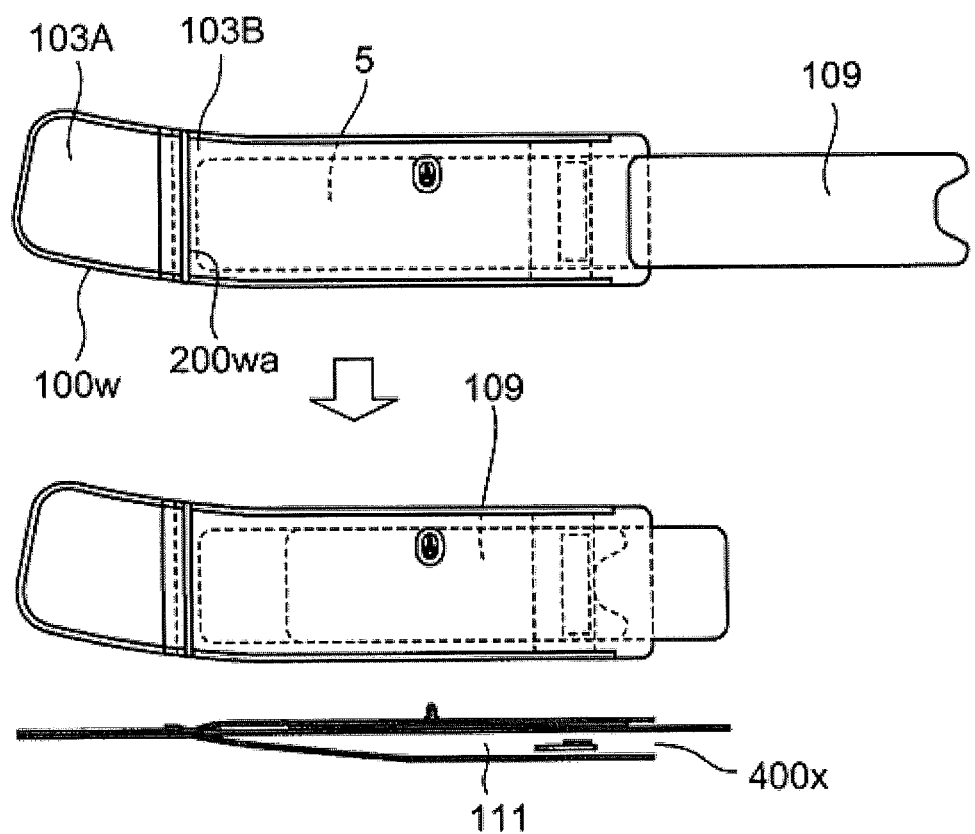
FIG. 21D is a schematic diagram illustrating a step for manufacturing the blood pressure measurement cuff according to the fourth embodiment.

Next, in step S404, a plate-shaped curler insertion auxiliary plate 5 is inserted into the air bladder 111 through the unwelded portion (opening 400x (FIG. 21D)) (FIG. 21D).

Next, in step S405, the curler 109 is pressed to the curler insertion auxiliary plate 5 so as to be elastically deformed into an approximate plate shape, and is slid over the plate 5 so as to be inserted into the air bladder 111 through the opening 400x (FIG. 21D).

Figure 21E:
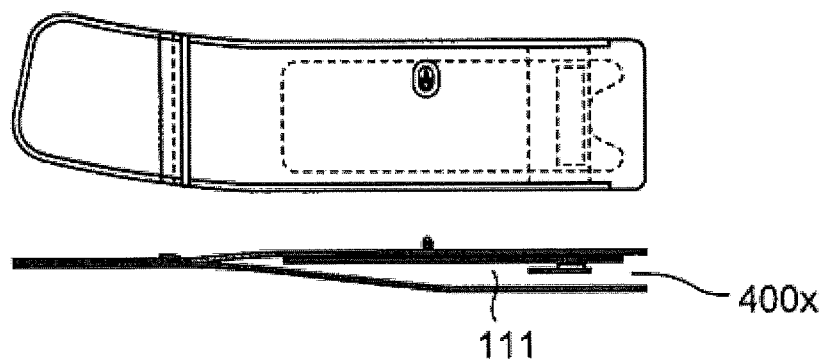
FIG. 21E is a schematic diagram illustrating a step for manufacturing the blood pressure measurement cuff according to the fourth embodiment.

Next, in step S406, the curler insertion auxiliary plate 5 is taken out of the air bladder 111 (FIG. 21E).

Note that instead of performing steps S404, S405, and S406, it is possible to prepare two curler insertion auxiliary plates, elastically deform the curler 109 into an approximate plate shape and sandwich it between the two plates, and in that state, insert them into the air bladder 111 through the opening 400x, thereafter removing only the two plates from the air bladder 111.

Next, in step S407, the double-sided adhesive tape 402 is used to attach the curler 109 to the curler fixing sheet member 401 (FIG. 21E).

Figure 21F:
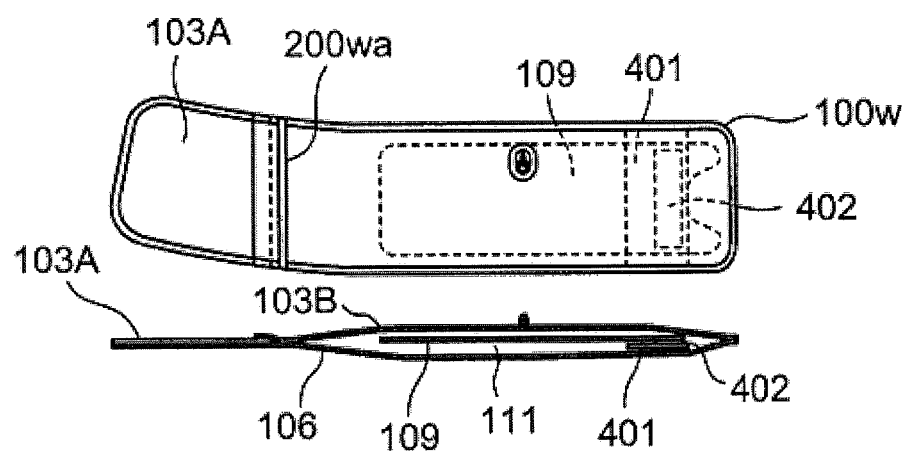
FIG. 21F is a schematic diagram illustrating a step for manufacturing the blood pressure measurement cuff according to the fourth embodiment.

Next, in step S408, at the portion that was not welded in step S402 (opening 400x (FIG. 21D)), the airtight sheet member 102 of the outer member 103B and the airtight sheet member 104 of the inner member 106 are welded together so as to close the opening 400x and form the complete air bladder 111 (FIG. 21F).

Figure 21G:
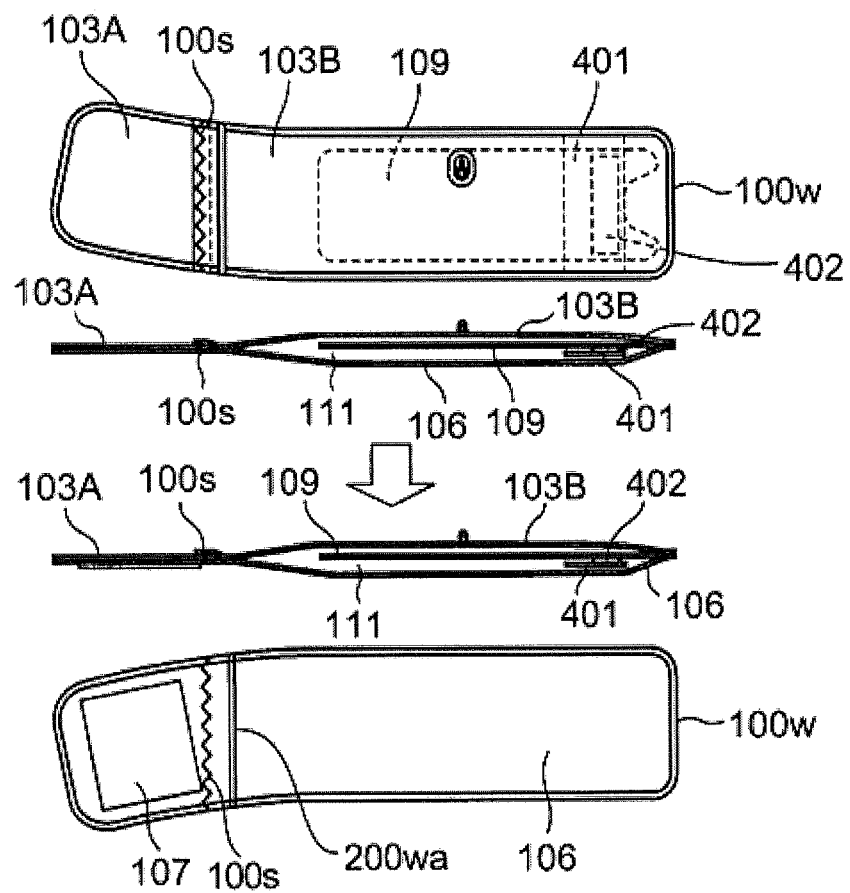
FIG. 21G is a schematic diagram illustrating a step for manufacturing the blood pressure measurement cuff according to the fourth embodiment.

Finally, in step S409, a sewing process for attaching the hook-and-loop fastener 107 or the like is performed (FIG. 21G).

As described above, according to the present method for manufacturing, it is possible to manufacture the cuff 400 in an extremely simple manner. In the present method, since the outer cloths 101A and 101B and the inner cloth 105 do not need to be sewn together at the outer perimeter portion of the cuff 400 to form the bag-shaped outer cover, the manufacturing cost can be reduced.

Figures 22A, 22B:
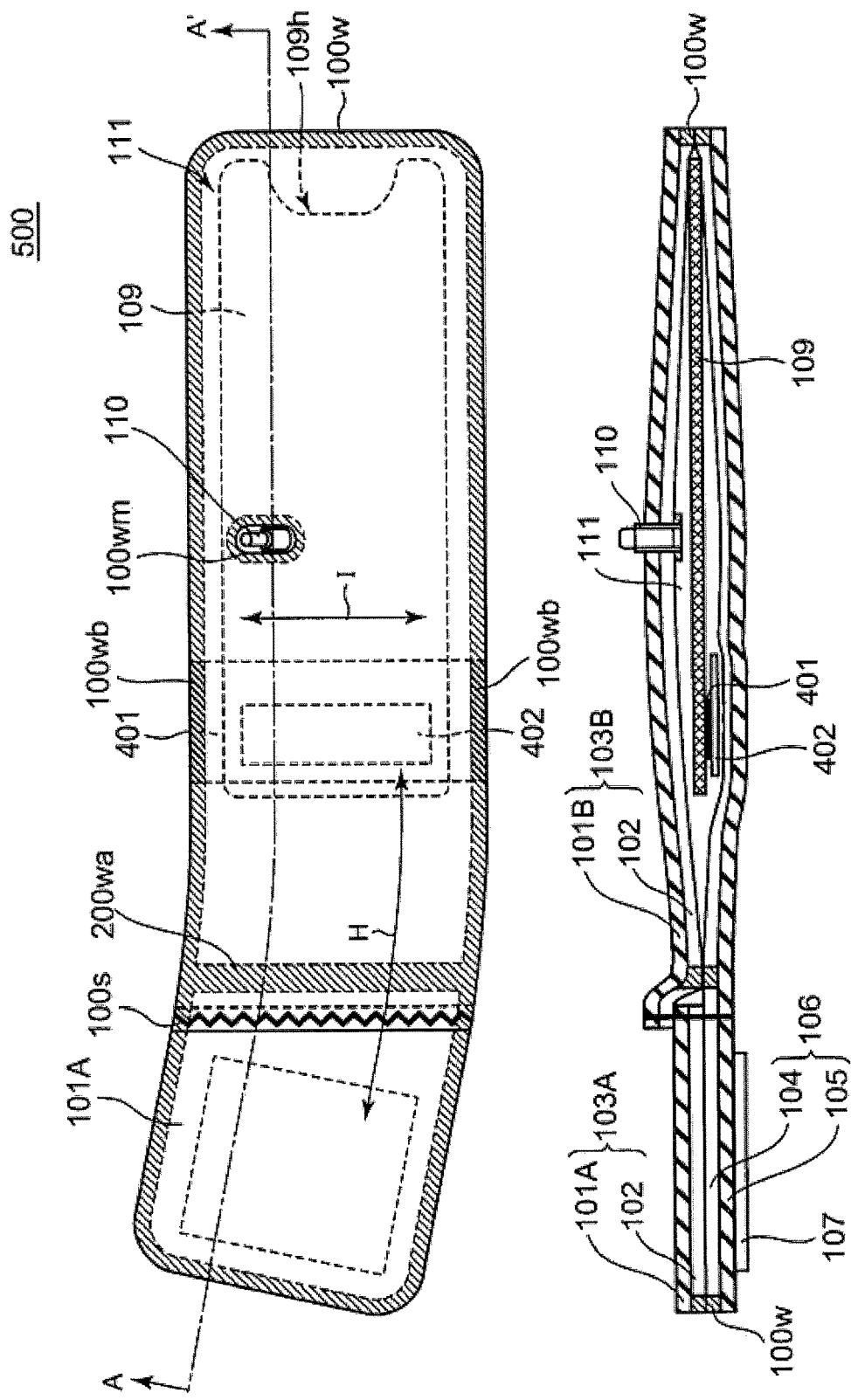
FIG. 22(a) is a plan view of an expanded state of a blood pressure measurement cuff according to a fifth embodiment.
FIG. 22(b) is a cross-sectional view taken along line A-A' in FIG. 22(a).

Next, a cuff 500 according to a fifth embodiment of the present invention will be described. FIG. 22(a) is a plan view of an expanded state of the cuff 500 according to the fifth embodiment of the present invention, and FIG. 22(b) is a cross-section taken along line A-A' in FIG. 22(a). In the description below, description of configurations that are the same as in the preceding embodiment are omitted as appropriate.

In the cuff 500 according to the present embodiment, similarly to the cuff according to the preceding embodiment, the airtight sheet member 102 and the airtight sheet member 104 are welded together at the intermediate welded portion 200wa and the peripheral edge welded portion 100w to form the air bladder 111. With the cuff 500, similarly to the cuff 400, the length in the circumferential direction H of the air bladder 111 can be designed independently of the length in the circumferential direction H of the curler 109. For this reason, the cuff 500 according to the present embodiment includes, as a positioning portion, a curler fixing sheet member 401. Unlike the cuff 400 according to the fourth embodiment, the curler fixing sheet member 401 is attached to the air bladder 111 by being welded at the peripheral edge portion of the air bladder 111 near the central welded portion 200wa (peripheral edge welded portion 100wb) while being sandwiched between the airtight sheet member 102 and the airtight sheet member 104, and the curler 109 is positioned with respect to the air bladder 111 by attaching the curler fixing sheet member 401 to the curler 109 using the double-sided adhesive tape 402. Note that with the cuff 500, similarly to the cuff 400, a protrusion does not need to be included on the outer surface of the curler 109 as with the curler 209 in the second embodiment.

Thus, in the cuff 500 according to the fifth embodiment, a means for positioning the curler 109 in the air bladder 111 is provided. Accordingly, the length in the circumferential direction H of the air bladder 111 can be designed freely, regardless of the length in the circumferential direction H of the curler 109, and the curler 109 is prevented from moving around needlessly in the air bladder 111.

Figure 23:
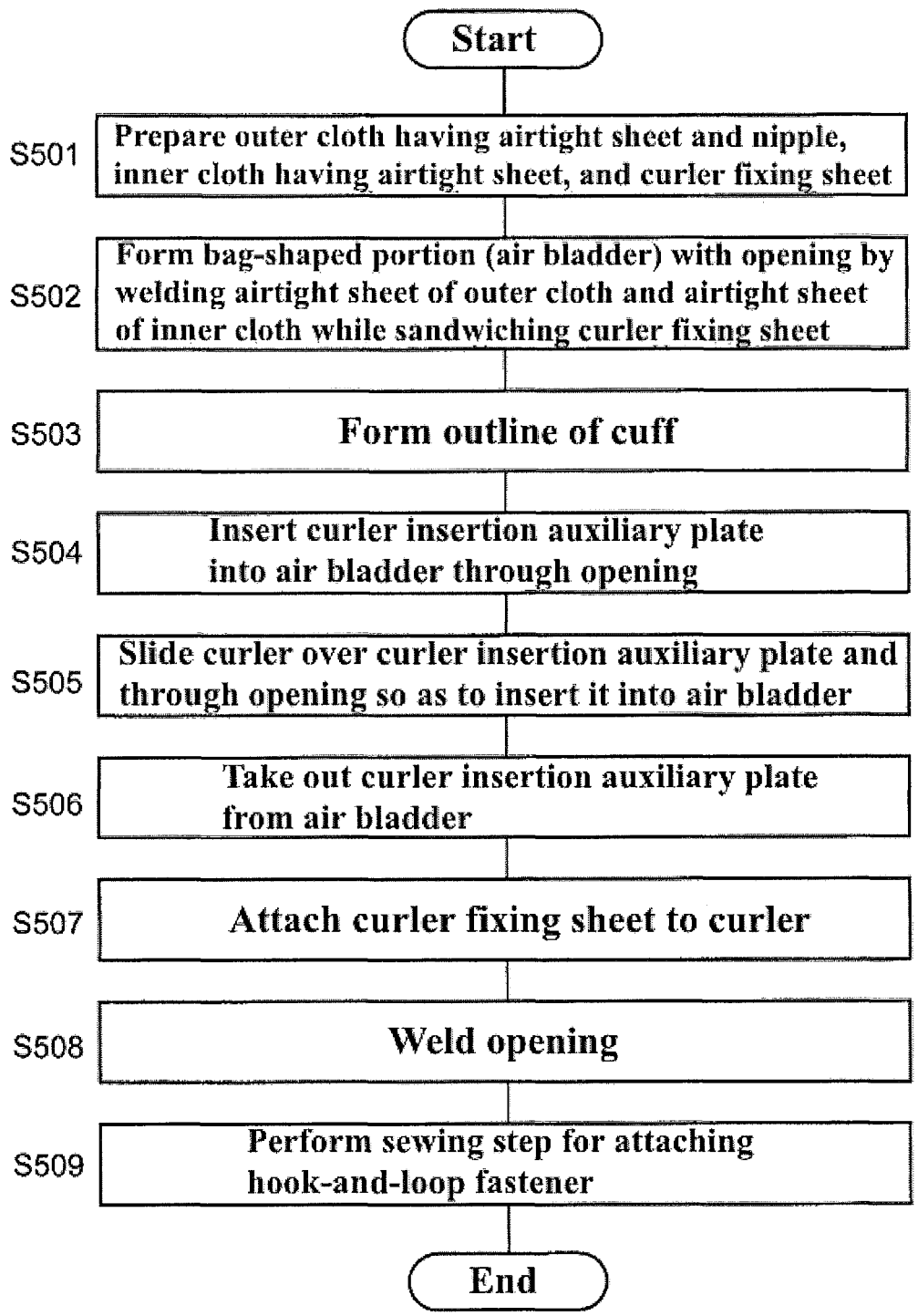
FIG. 23 is a flowchart showing steps for manufacturing the blood pressure measurement cuff according to the fifth embodiment.

Next, with reference to FIG. 23 and FIGS. 24A to 24H, a method for manufacturing the cuff 500 will be described. FIG. 23 is a flowchart showing steps for manufacturing the cuff 500, and FIGS. 24A to 24H are schematic diagrams showing states of members in the steps of the manufacturing process.

Figure 24A:
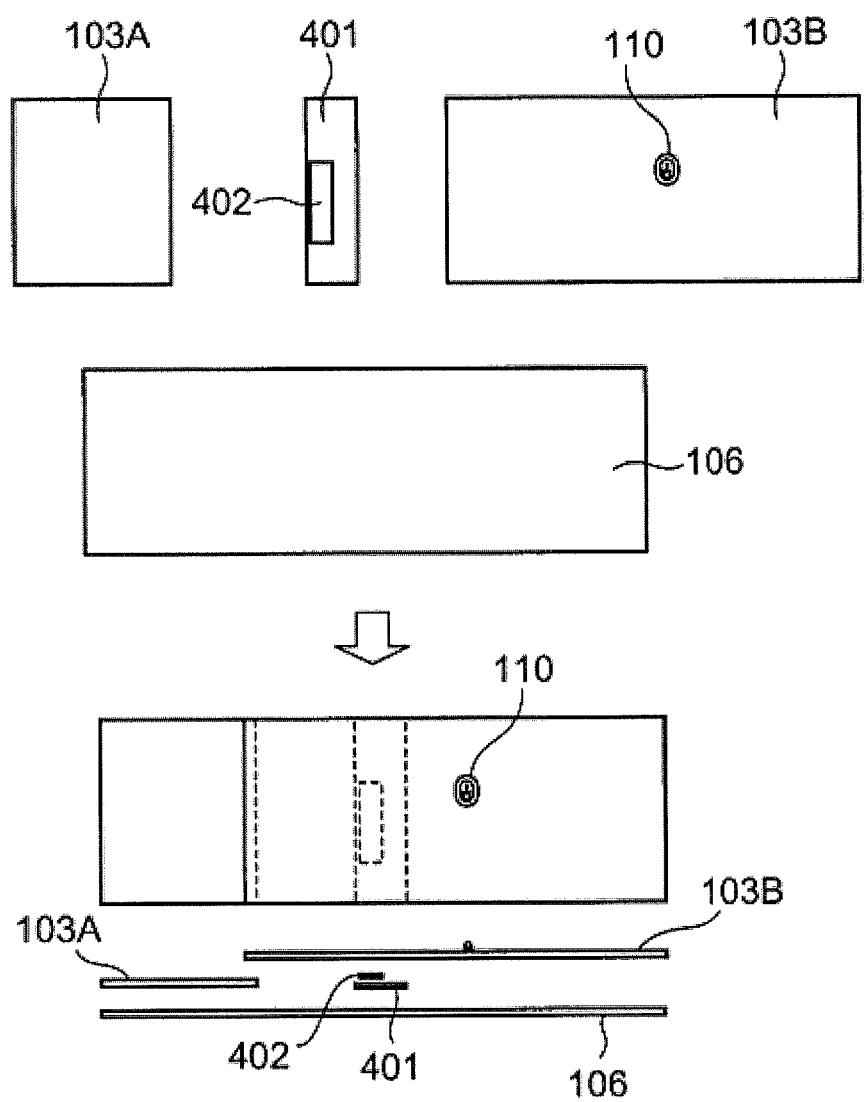
FIG. 24A is a schematic diagram illustrating a step for manufacturing the blood pressure measurement cuff according to the fifth embodiment.

First, in step S501, the outer cloth 101A to which the airtight sheet member 102 is attached, or in other words, the outer member 103A, the outer member 103B to which the airtight sheet member 102 and the nipple 110 are attached, the inner cloth 105 to which the airtight sheet member 104 is attached, or in other words, the inner member 106, and the curler fixing sheet member 401 to which the double-sided adhesive tape 402 is attached, are prepared (FIG. 24A).

Figure 24B:
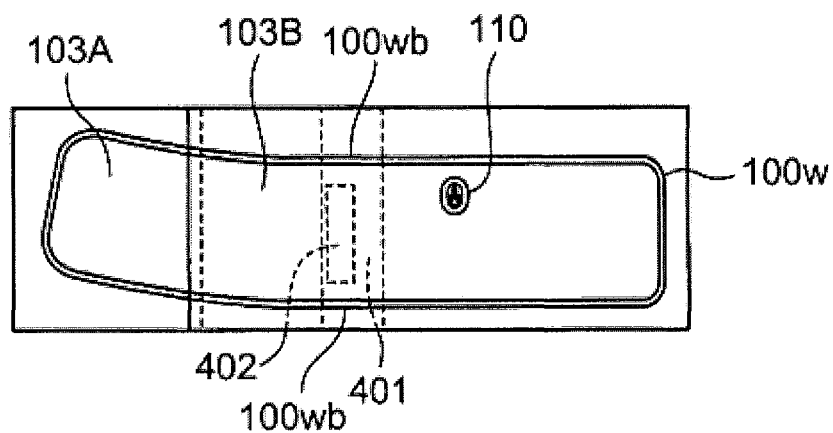
FIG. 24B is a schematic diagram illustrating a step for manufacturing the blood pressure measurement cuff according to the fifth embodiment.

Next, in step S502, the airtight sheet member 102 of the outer members 103A and 103B and the airtight sheet member 104 of the inner member 106 are welded together while sandwiching the curler fixing sheet member 401 at the center in the circumferential direction of the peripheral edge portion of the cuff (air bladder 111) (peripheral edge welded portion 100wb (FIG. 24B)) so as to form a bag-shaped portion (air bladder) having an opening (FIG. 24B). In the present step, the opening (500x (FIG. 24D)) is provided at a central portion of the cuff 500 (portion at which the outer member 103A and the outer member 103B are connected).

Figure 24C:
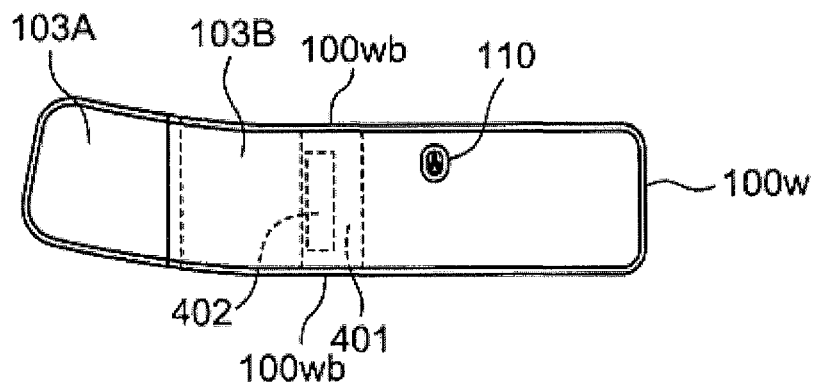
FIG. 24C is a schematic diagram illustrating a step for manufacturing the blood pressure measurement cuff according to the fifth embodiment.

Next, in step S503, extraneous members are cut with a die, thus forming a cuff (FIG. 24C).

Figure 24D:
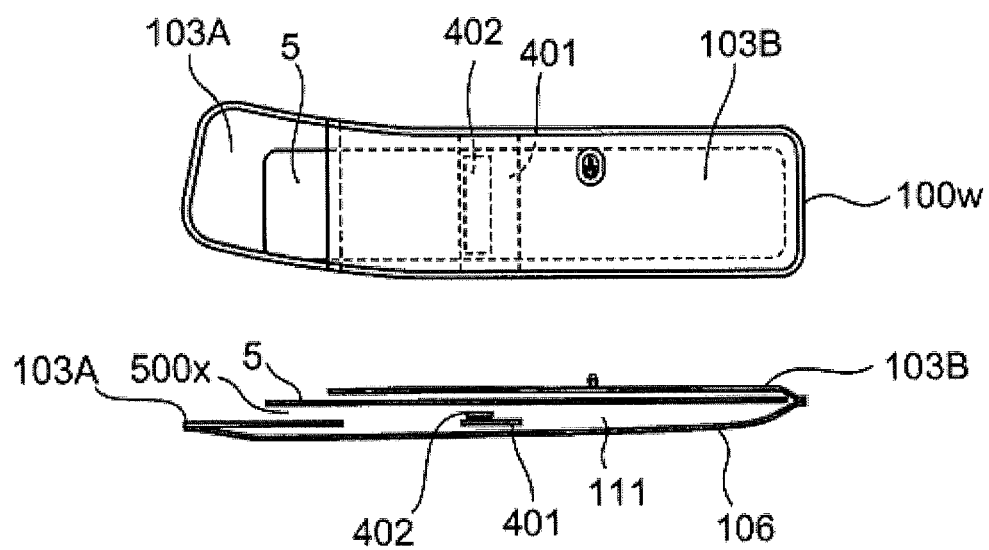
FIG. 24D is a schematic diagram illustrating a step for manufacturing the blood pressure measurement cuff according to the fifth embodiment.

Next, in step S504, a plate-shaped curler insertion auxiliary plate 5 is inserted into the air bladder 111 through the unwelded portion (opening 500x) (FIG. 24D).

Figure 24E:
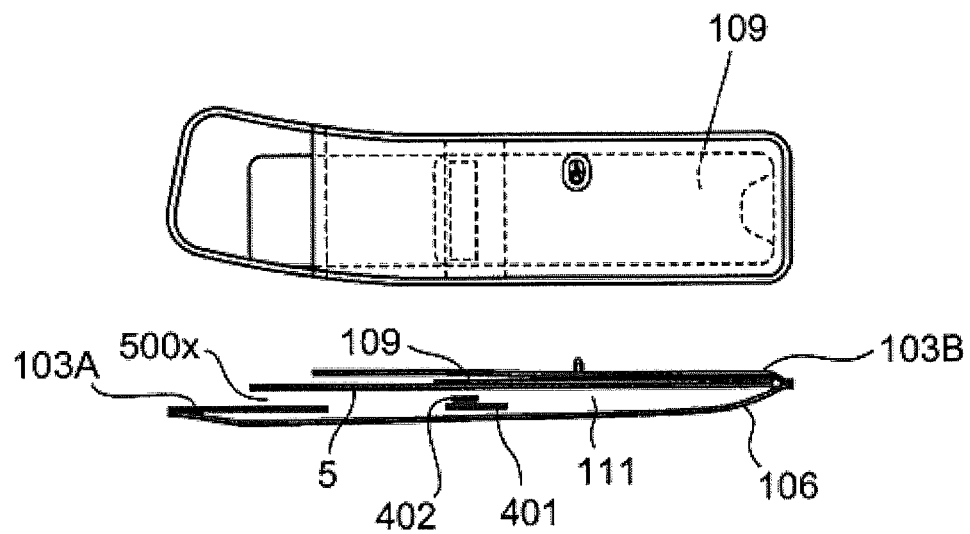
FIG. 24E is a schematic diagram illustrating a step for manufacturing the blood pressure measurement cuff according to the fifth embodiment.

Next, in step S505, the curler 109 is pressed to the curler insertion auxiliary plate 5 so as to be elastically deformed into an approximate plate shape, and is slid over the plate 5 so as to be inserted into the air bladder 111 through the opening 500x (FIG. 24E).

Figure 24F:
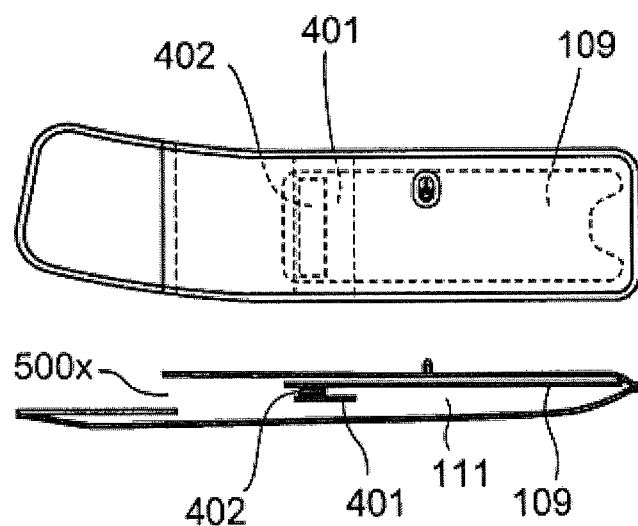
FIG. 24F is a schematic diagram illustrating a step for manufacturing the blood pressure measurement cuff according to the fifth embodiment.
Figure 24G:
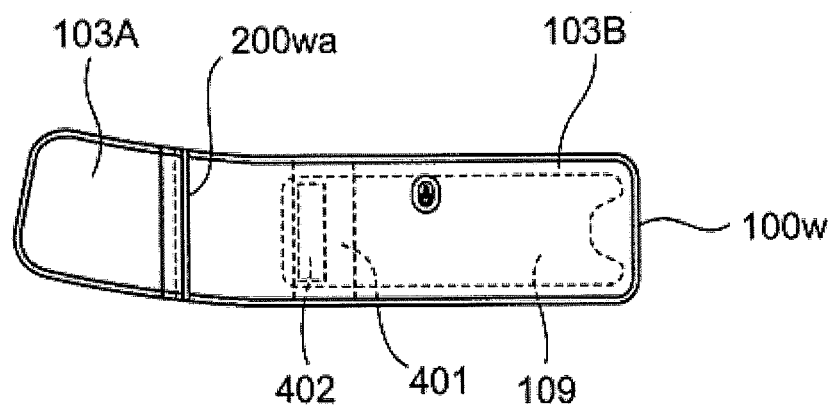
FIG. 24G is a schematic diagram illustrating a step for manufacturing the blood pressure measurement cuff according to the fifth embodiment.

Next, in step S506, the curler insertion auxiliary plate 5 is taken out of the air bladder 111 (FIG. 24F).

Note that instead of performing steps S504, S505, and S506, it is possible to prepare two curler insertion auxiliary plates, elastically deform the curler 109 into an approximate plate shape and sandwich it between the two plates, and in that state, insert them into the air bladder 111 through the opening 500x, thereafter removing only the two plates from the air bladder 111.

Next, in step S507, the double-sided adhesive tape 402 is used to attach the curler 109 to the curler fixing sheet member 401 (FIG. 24F).

Next, in step S508, at the portion that was not welded in step S402 (opening 500x), the airtight sheet member 102 of the outer members 103A and 103B and the airtight sheet member 104 of the inner member 106 are welded together so as to close the opening 500x and form the complete air bladder 111 (FIG. 24F).

Figure 24H:
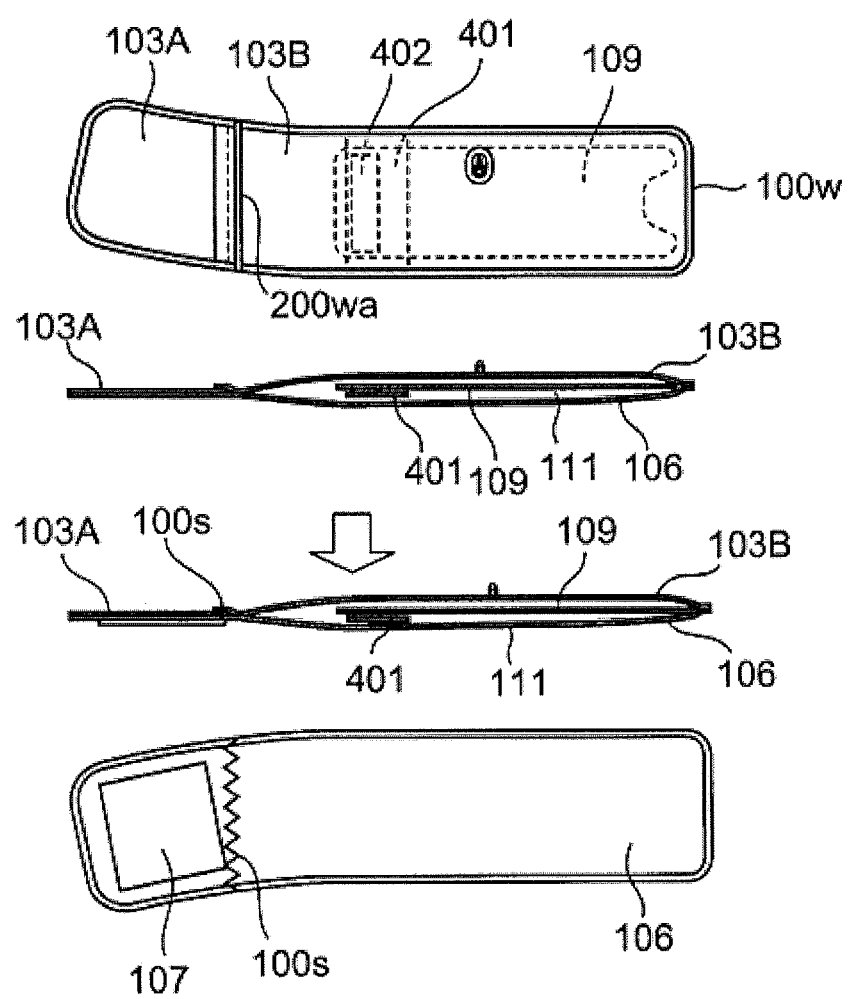
FIG. 24H is a schematic diagram illustrating a step for manufacturing the blood pressure measurement cuff according to the fifth embodiment.

Finally, in step S509, a sewing process for attaching the hook-and-loop fastener 107 or the like is performed (FIG. 24H).

As described above, according to the present method for manufacturing, it is possible to manufacture the cuff 500 in an extremely simple manner. In the present method, since the outer cloths 101A and 101B and the inner cloth 105 do not need to be sewn together at the outer perimeter portion of the cuff 500 to form the bag-shaped outer cover, the manufacturing cost can be reduced.

Figure 25A:
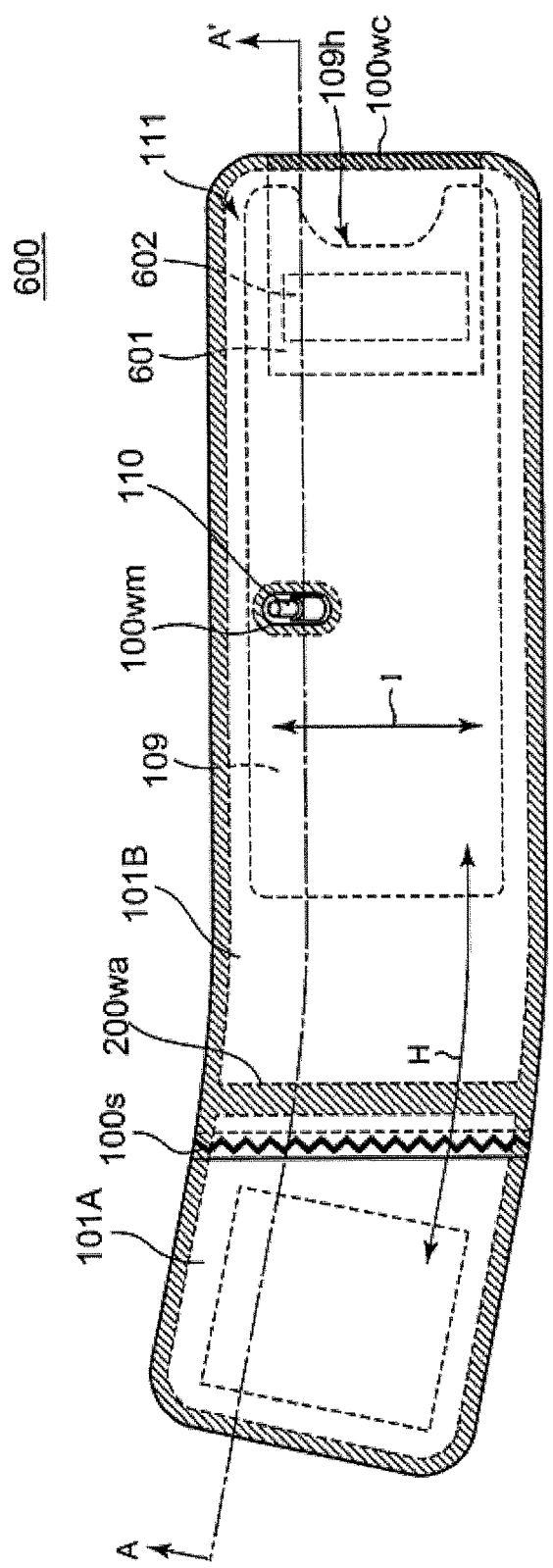
FIG. 25(a) is a plan view of an expanded state of a blood pressure measurement cuff according to a sixth embodiment.
Figure 25B:
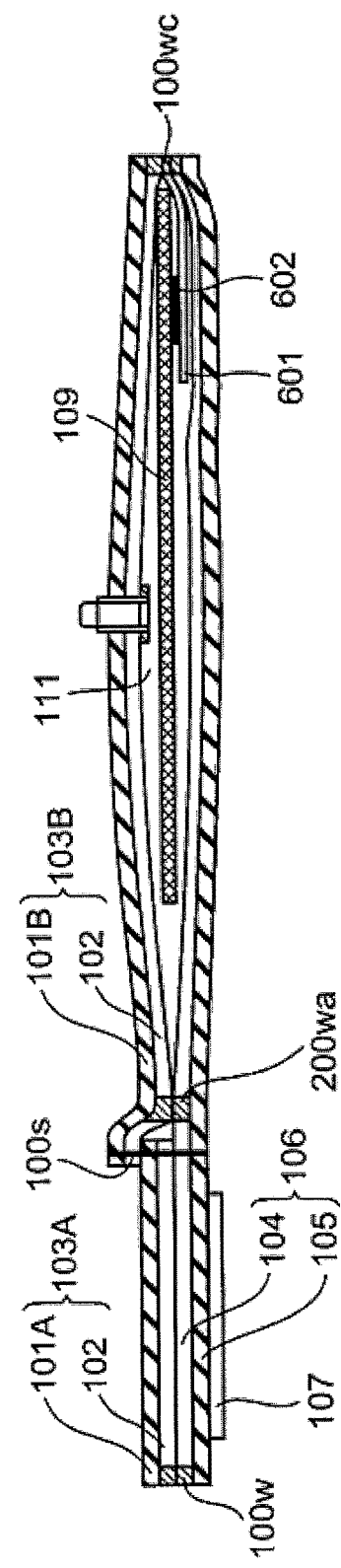
FIG. 25(b) is a cross-sectional view taken along line A-A' in FIG. 25(a).

Next, a cuff 600 according to a sixth embodiment of the present invention will be described. FIG. 25(*a*) is a plan view of an expanded state of the cuff 600 according to the sixth embodiment of the present invention, and FIG. 25(*b*) is a cross-section taken along line A-A' in FIG. 25(*a*). In the description below, description of configurations that are the same as in the preceding embodiment will be omitted as appropriate.

In the cuff 600 according to the present embodiment, similarly to the cuff according to the preceding embodiment, the airtight sheet member 102 and the airtight sheet member 104 are welded together at the intermediate welded portion 200wa and the peripheral edge welded portion 100w to form the air bladder 111. With the cuff 600, similarly to the cuff 500, the length in the circumferential direction H of the air bladder 111 can be designed independently of the length in the circumferential direction H of the curler 109. Accompanying this, the cuff 600 according to the present embodiment includes, as a positioning portion, a curler fixing sheet member 601. The curler fixing sheet member 601 is attached to the air bladder 111 by being welded at the peripheral edge portion in the width direction I of the air bladder 111 (peripheral edge welded portion 100wc), which is approximately perpendicular to the circumferential direction H of the air bladder 111, while being sandwiched between the airtight sheet member 102 and the airtight sheet member 104, and the curler 109 is positioned with respect to the air bladder 111 by the curler fixing sheet member 601 being attached to the curler 109 with double-sided adhesive tape 602. Note that in the cuff 600, similarly to the cuff 500 and the like, there is no need to include a protrusion on the outer surface of the curler 109 as with the curler 209 in the second embodiment.

Figure 26:
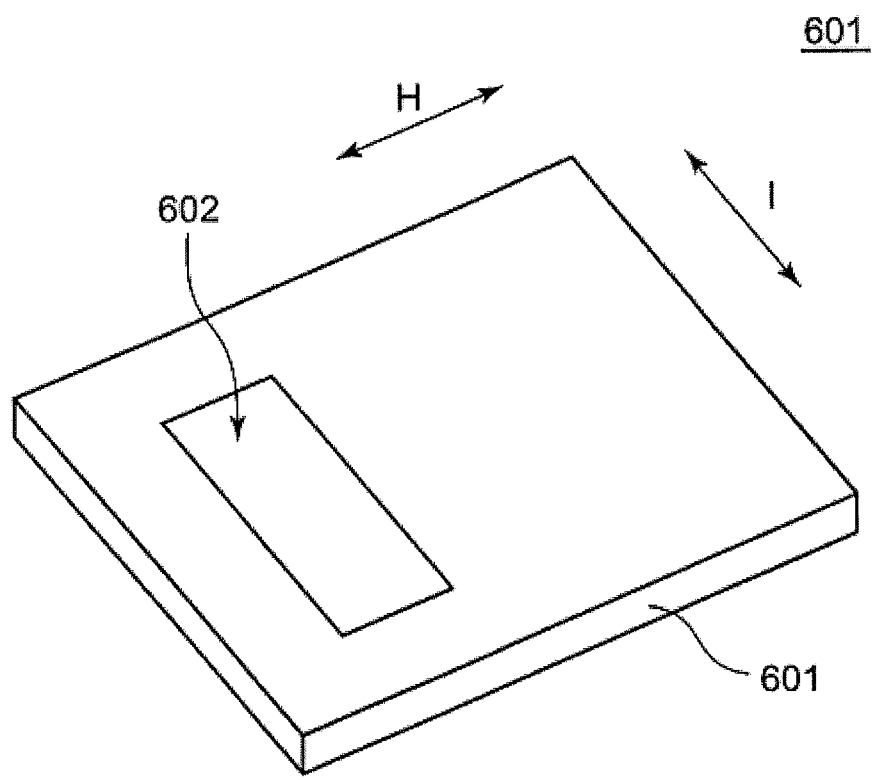
FIG. 26 is a perspective view of a positioning portion according to the sixth embodiment.

FIG. 26 is a perspective view of the curler fixing sheet member 601. The curler fixing sheet member 601 is a PVC sheet, for example. The double-sided adhesive tape 602 is adhered to the upper surface of the curler fixing sheet member 601.

Thus, in the cuff 600 according to the sixth embodiment, a means for positioning the curler 109 in the air bladder 111 is provided. Accordingly, the length in the circumferential direction H of the air bladder 111 can be designed freely, regardless of the length in the circumferential direction H of the curler 109, and the curler 109 is prevented from moving around needlessly in the air bladder 111.

Figure 27:
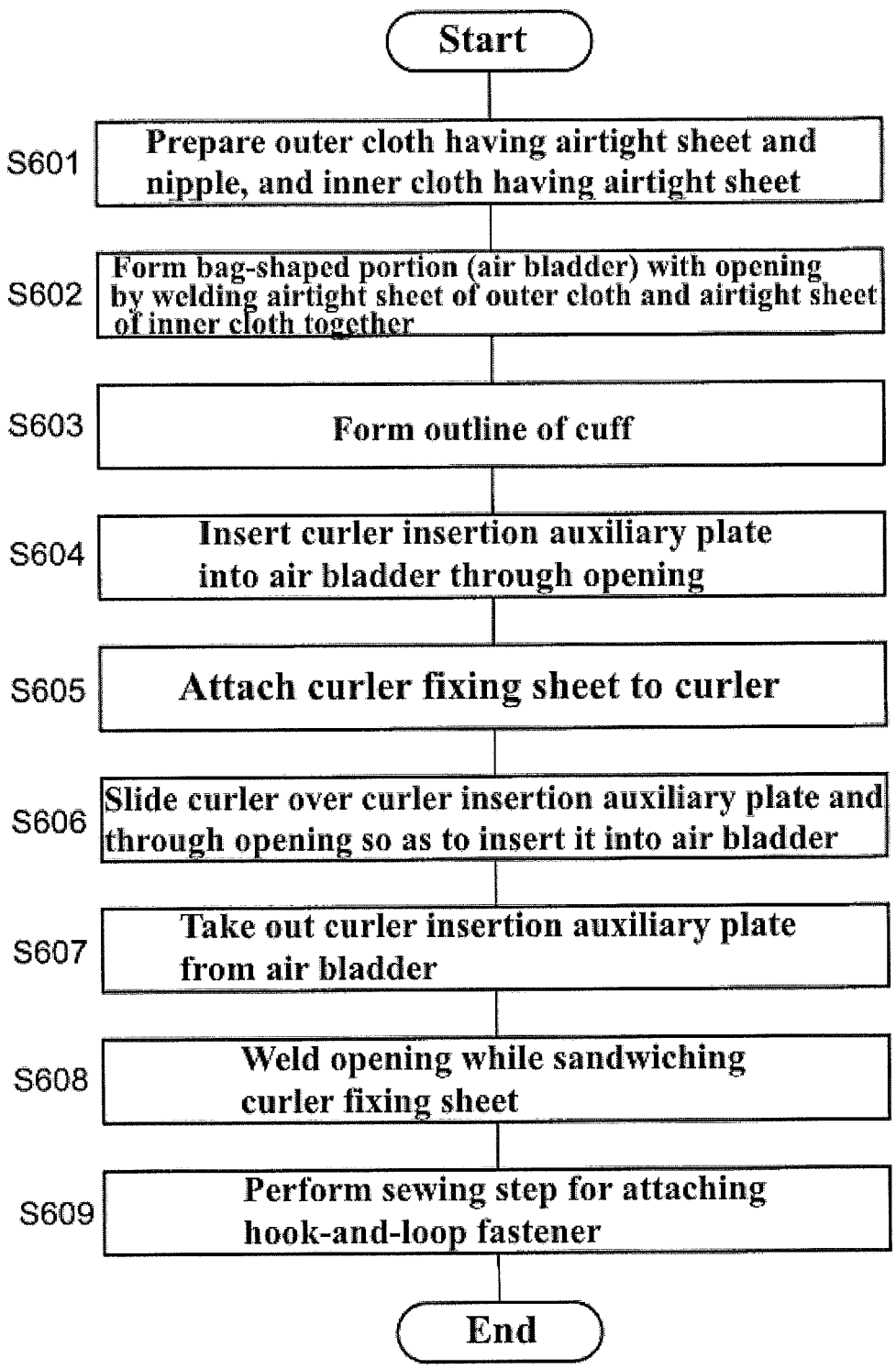
FIG. 27 is a flowchart showing steps for manufacturing the blood pressure measurement cuff according to the sixth embodiment.

Next, with reference to FIG. 27 and FIGS. 28A to 28J, a method for manufacturing the cuff 600 will be described. FIG. 27 is a flowchart showing steps for manufacturing the cuff 600, and FIGS. 28A to 28J are schematic diagrams showing states of members in the steps of the manufacturing process.

Figure 28A:
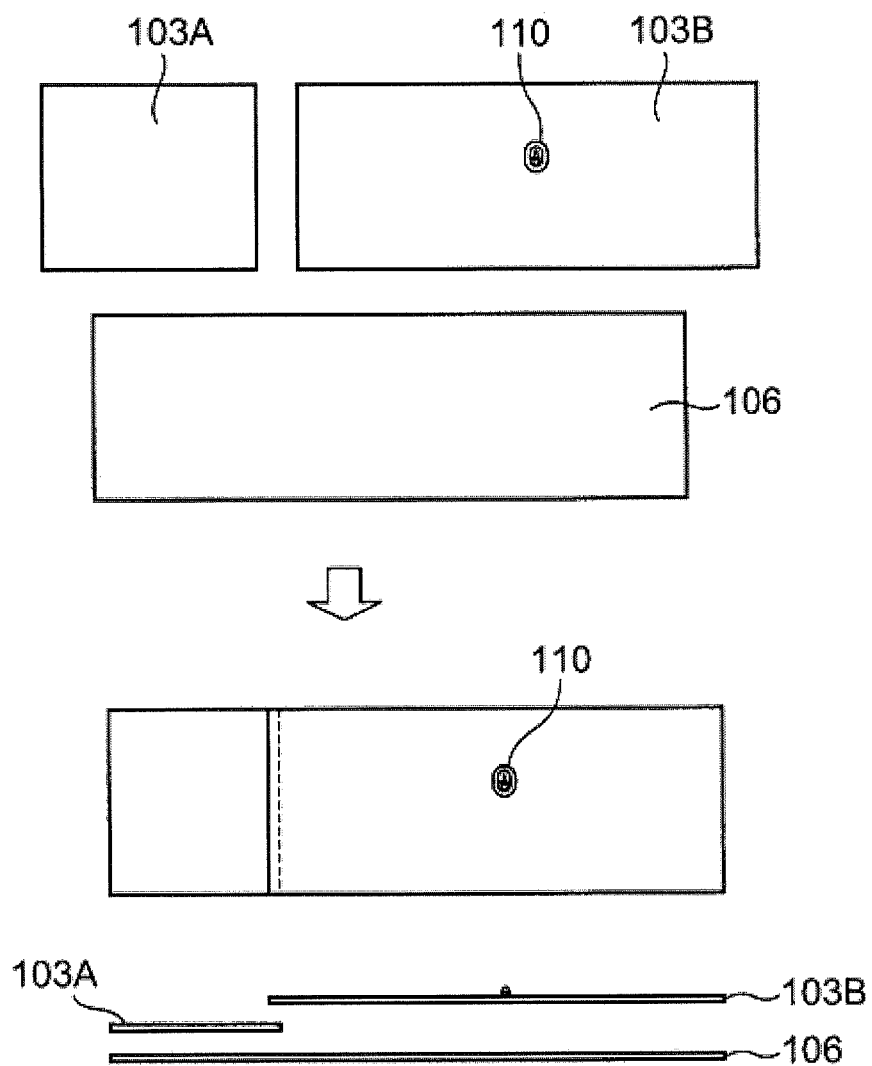
FIG. 28A is a schematic diagram illustrating a step for manufacturing the blood pressure measurement cuff according to the sixth embodiment.

First, in step S601, the outer cloth 101A to which the airtight sheet member 102 is attached, or in other words, the outer member 103A, the outer member 103B to which the airtight sheet member 102 and the nipple 110 are attached, and the inner cloth 105 to which the airtight sheet member 104 is attached, or in other words, the inner member 106, are prepared (FIG. 28A).

Figure 28B:
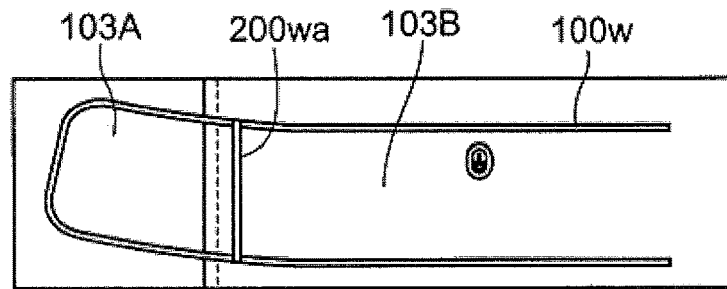
FIG. 28B is a schematic diagram illustrating a step for manufacturing the blood pressure measurement cuff according to the sixth embodiment.

Next, in step S602, the airtight sheet member 102 of the outer members 103A and 103B and the airtight sheet member 104 of the inner member 106 are welded together (peripheral edge welded portion 100w) so as to form a bag-shaped portion (air bladder) having an opening (FIG. 28B). In the present step, the opening (600x (FIG. 28F)) is provided on the circumferential end of the cuff 600 (end on the right side of the cuff in FIG. 28B).

Figure 28C:
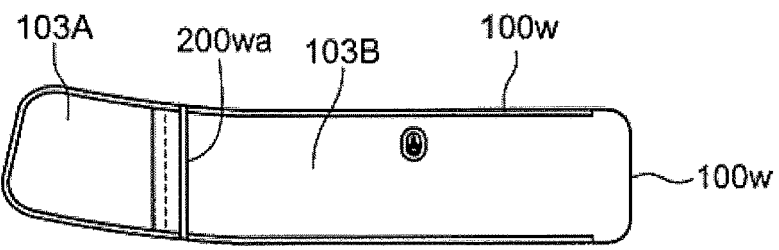
FIG. 28C is a schematic diagram illustrating a step for manufacturing the blood pressure measurement cuff according to the sixth embodiment.

Next, in step S603, extraneous members are cut with a die, thus forming a cuff (FIG. 28C).

Figure 28D:
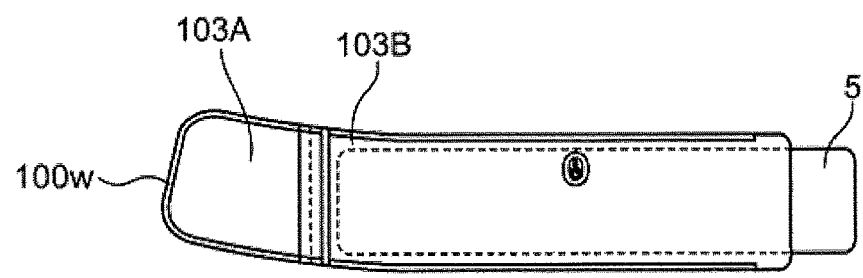
FIG. 28D is a schematic diagram illustrating a step for manufacturing the blood pressure measurement cuff according to the sixth embodiment.

Next, in step S604, a plate-shaped curler insertion auxiliary plate 5 is inserted into the air bladder 111 through the unwelded portion (opening 600x) (FIG. 28D).

Figure 28E:
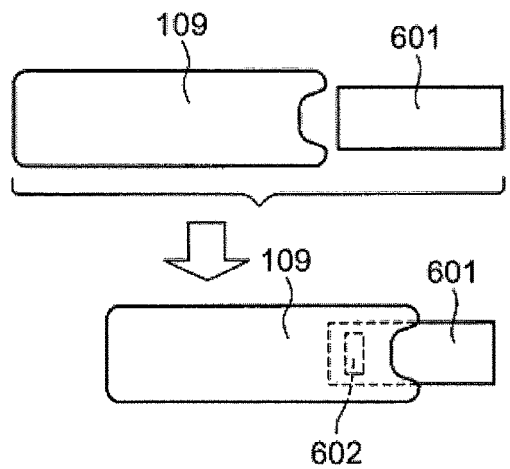
FIG. 28E is a schematic diagram illustrating a step for manufacturing the blood pressure measurement cuff according to the sixth embodiment.

Next, in step S605, the double-sided adhesive tape 602 is used to attach the curler fixing sheet member 601 to the curler 109 (FIG. 28E).

Figure 28F:
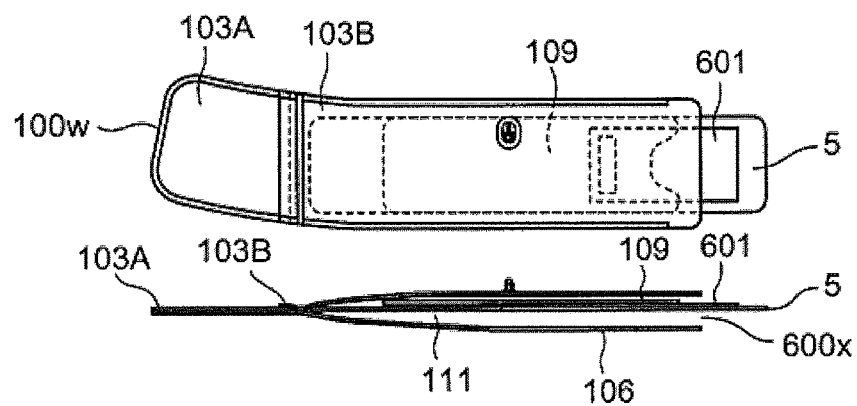
FIG. 28F is a schematic diagram illustrating a step for manufacturing the blood pressure measurement cuff according to the sixth embodiment.

Next, in step S606, the curler 109, to which the curler fixing sheet member 601 is attached, is pressed to the curler insertion auxiliary plate 5 so as to be elastically deformed into an approximate plate shape, and is slid over the plate 5 so as to be inserted into the air bladder 111 through the opening 600x (FIG. 28F).

Figure 28G:
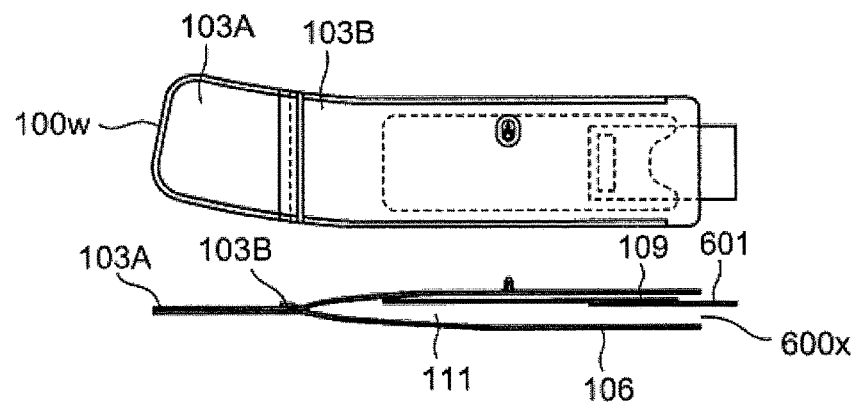
FIG. 28G is a schematic diagram illustrating a step for manufacturing the blood pressure measurement cuff according to the sixth embodiment.

Next, in step S607, the curler insertion auxiliary plate 5 is taken out of the air bladder 111 (FIG. 28G).

Note that instead of performing steps S604, S606, and S607, it is possible to prepare two curler insertion auxiliary plates, elastically deform the curler 109 into an approximate plate shape and sandwich it between the two plates, and in that state, insert them into the air bladder 111 through the opening 600x, thereafter removing only the two plates from the air bladder 111.

Figure 28H:
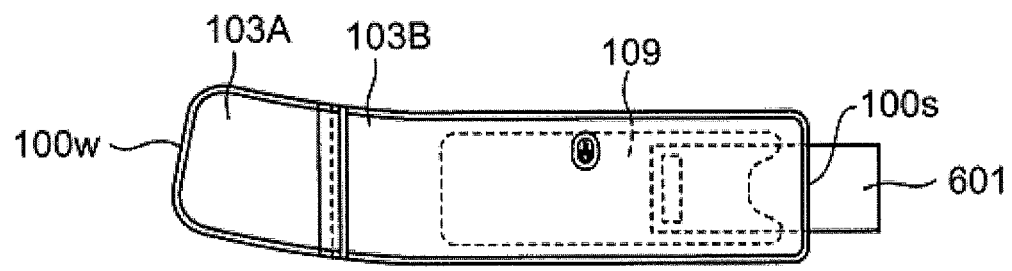
FIG. 28H is a schematic diagram illustrating a step for manufacturing the blood pressure measurement cuff according to the sixth embodiment.
Figure 28I:
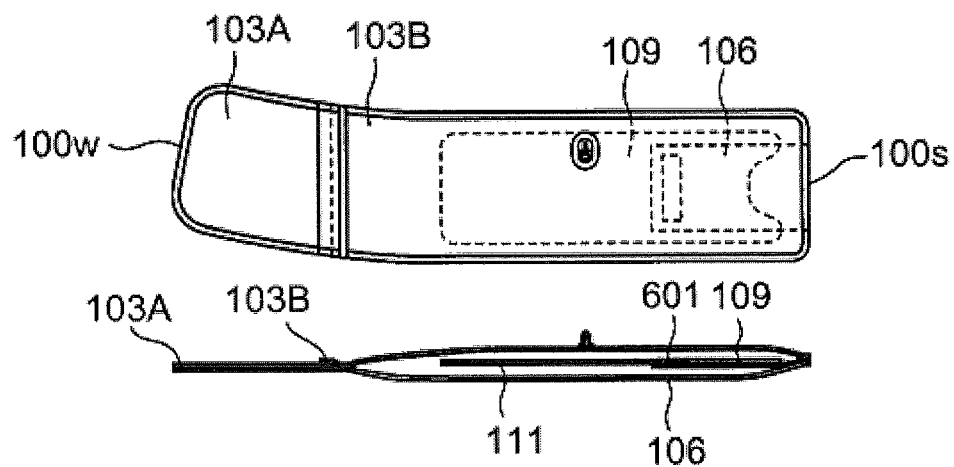
FIG. 28I is a schematic diagram illustrating a step for manufacturing the blood pressure measurement cuff according to the sixth embodiment.

Next, in step S608, the airtight sheet member 102 of the outer member 103B and the airtight sheet member 104 of the inner member 106 are welded together while sandwiching the curler fixing sheet member 601 (peripheral edge welded portion 100wc (FIG. 25)) at the portion that was not welded in step S602 (opening 600x) so as to close the opening 600x and form the complete air bladder 111 (FIG. 28H). Next, extraneous members (the portion of the curler fixing sheet member 601 that exceeds the peripheral edge welded portion 100wc and protrudes outward from the air bladder 111) are cut so as to form the cuff (FIG. 28I).

Figure 28J:
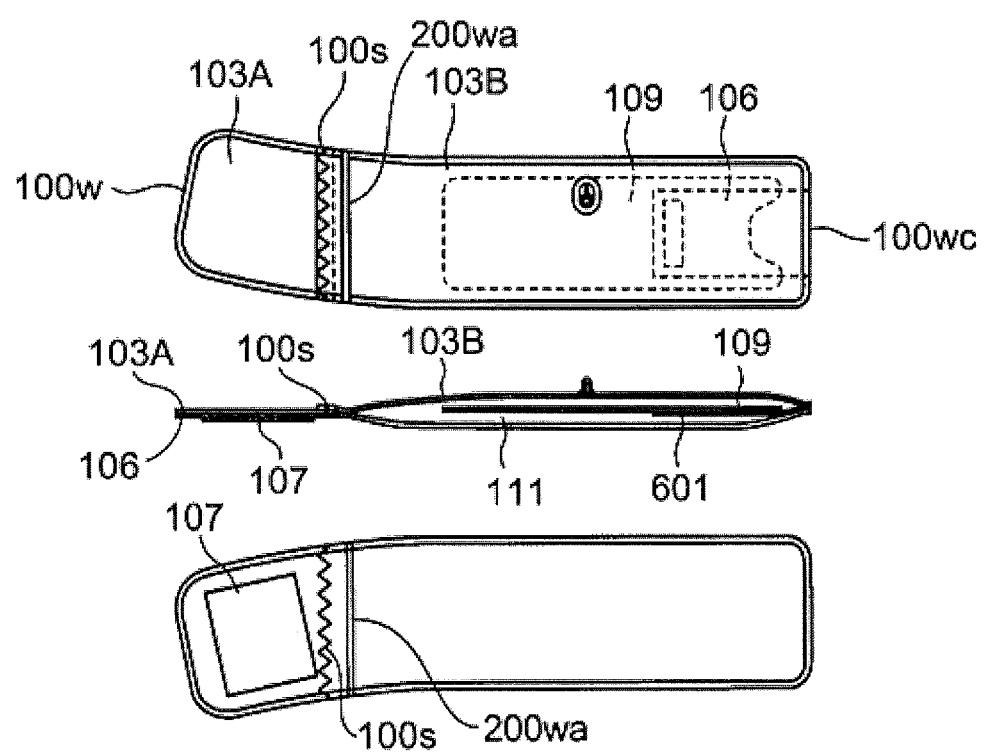
FIG. 28J is a schematic diagram illustrating a step for manufacturing the blood pressure measurement cuff according to the sixth embodiment.

Finally, in step S609, a sewing process for attaching the hook-and-loop fastener 107 or the like is performed (FIG. 28J).

As described above, according to the present method for manufacturing, it is possible to manufacture the cuff 600 in an extremely simple manner. In the present method, since the outer cloths 101A and 101B and the inner cloth 105 do not need to be sewn together at the outer perimeter portion of the cuff 600 to form the bag-shaped outer cover, the manufacturing cost can be reduced.

REFERENCE SIGNS LIST

5: Curler insertion auxiliary plate
100: Blood pressure measurement cuff
100s: Suture
100w: Peripheral edge welded portion
100wa: Intermediate welded portion
100wb: Peripheral edge welded portion
100wc: Peripheral edge welded portion
100x: Opening
101A, 101B: Outer cloth
102: Airtight sheet
103A, 103B: Outer member
104: Airtight sheet
105: Inner cloth
106: Inner member
107: Hook-and-loop fastener
109: Curler
109h: Recess
110: Nipple
111: Air bladder
200: Blood pressure measurement cuff
200wa: Intermediate welded portion
200x: Opening
209: Curler
209p: Protrusion
300: Blood pressure measurement cuff
301: Curler fixing sheet member
302, 303: Double-sided adhesive tape
300x: Opening
400: Blood pressure measurement cuff
401: Curler fixing sheet member
402: Double-sided adhesive tape
400x: Opening
500: Blood pressure measurement cuff
500x: Opening
600: Blood pressure measurement cuff
601: Curler fixing sheet member
602: Double-sided adhesive tape
600x: Opening

The invention claimed is:

1. A method for manufacturing a blood pressure measurement cuff configured to be wrapped around a measurement site,
the method comprising:
preparing an outer cloth attached to a first airtight sheet member;
preparing an inner cloth attached to a second airtight sheet member;
forming a bag-shaped portion by welding the first airtight sheet member to the second airtight sheet member, the bag-shaped portion having an opening on a peripheral edge of the bag-shaped portion;
inserting a curler into the bag-shaped portion through the opening, the curler being flexible and configured to curve and conform to the measurement site, the insertion of the curler further including:
inserting a plate-shaped curler insertion auxiliary plate into the bag-shaped portion through the opening;
pressing the curler onto the curler insertion auxiliary plate while sliding the curler over the curler insertion auxiliary plate and through the opening so as to insert the curler into the bag-shaped portion; and
removing the curler insertion auxiliary plate from the bag-shaped portion through the opening; and
forming an air bladder by welding the opening of the bag-shaped portion such that the air bladder surrounds an inner side and an outer side of the curler thereby containing the curler, the outer cloth being attached to an outer surface on a first side of the air bladder configured to be opposite to the measurement site, and the inner cloth being attached to an outer surface on a second side of the air bladder configured to be towards the measurement site.

2. The method for manufacturing the blood pressure measurement cuff according to claim 1, the method further comprising fitting a protrusion formed on an outer surface of the curler into an interior of a nipple arranged on the outer cloth, upon inserting the curler into the bag-shaped portion, and prior to forming the air bladder.

3. A method for manufacturing a blood pressure measurement cuff configured to be wrapped around a measurement site,
the method comprising:
preparing an outer cloth attached to a first airtight sheet member;

preparing an inner cloth attached to a second airtight sheet member;

forming a bag-shaped portion by welding the first airtight sheet member to the second airtight sheet member, the bag-shaped portion having an opening on a peripheral edge of the bag-shaped portion;

inserting a curler into the bag-shaped portion through the opening, the curler being flexible and configured to curve and conform to the measurement site, the insertion of the curler further including:

inserting two plate-shaped curler insertion auxiliary plates and the curler into the bag-shaped portion through the opening while elastically deforming the curler into a plate shape and sandwiching the curler between the two curler insertion auxiliary plates; and removing the two curler insertion auxiliary plates from the bag-shaped portion through the opening.

\* \* \* \* \*